(12) United States Patent
Rosenblatt et al.

(10) Patent No.: US 6,981,983 B1
(45) Date of Patent: Jan. 3, 2006

(54) SYSTEM AND METHODS FOR SOFT TISSUE RECONSTRUCTION

(76) Inventors: Peter L. Rosenblatt, 5 Wykeham Rd., Newton, MA (US) 02465-2419; Dale E. Whipple, 91 Tania Dr., E. Taunton, MA (US) 02718

( * ) Notice: Subject to any disclaimer, the term of this patent is extended or adjusted under 35 U.S.C. 154(b) by 0 days.

(21) Appl. No.: 09/539,748

(22) Filed: Mar. 31, 2000

Related U.S. Application Data

(60) Provisional application No. 60/127,104, filed on Mar. 31, 1999, provisional application No. 60/154,763, filed on Sep. 20, 1999, provisional application No. 60/163,305, filed on Nov. 3, 1999.

(51) Int. Cl.
*A61B 17/08* (2006.01)
*A61D 1/00* (2006.01)

(52) U.S. Cl. .................... 606/216; 606/213; 128/898

(58) Field of Classification Search ............... 606/1, 606/139, 142, 144, 148, 213, 215, 216, 217, 606/218, 219, 220; 128/898
See application file for complete search history.

(56) References Cited

U.S. PATENT DOCUMENTS

| | | | |
|---|---|---|---|
| 3,527,223 A | 9/1970 | Shein | 128/129 |
| 3,744,495 A | 7/1973 | Johnson | 128/337 |
| 4,196,836 A | 4/1980 | Becht | 227/110 |
| 4,261,244 A | 4/1981 | Becht et al. | 411/472 |
| 4,278,091 A | 7/1981 | Borzone | 128/334 |
| 4,424,810 A | 1/1984 | Jewusiak | 128/326 |
| 4,454,875 A | 6/1984 | Pratt et al. | 128/92 B |
| 4,485,816 A | 12/1984 | Krumme | 128/334 R |
| 4,505,767 A | 3/1985 | Quin | 148/402 |
| 4,531,522 A | 7/1985 | Bedi et al. | 128/335 |
| 4,532,926 A | 8/1985 | O'Holla | 128/334 |
| 4,532,927 A | 8/1985 | Miksza, Jr. | 128/334 |
| 4,534,350 A | 8/1985 | Golden et al. | 128/334 |
| 4,548,202 A | 10/1985 | Duncan | 128/334 |
| 4,550,870 A | 11/1985 | Krumme et al. | 227/19 |
| 4,573,469 A | 3/1986 | Golden et al. | 128/334 |
| 4,627,437 A | 12/1986 | Bedi et al. | 128/334 |
| 4,635,637 A | 1/1987 | Schreiber | 128/337 |
| 4,665,906 A | 5/1987 | Jervis | 128/92 YN |
| 4,736,746 A | 4/1988 | Anderson | 128/334 R |
| 4,873,976 A | 10/1989 | Schreiber | 128/334 R |
| 4,887,601 A | 12/1989 | Richards | 606/219 |
| 4,934,364 A | 6/1990 | Green | 606/143 |
| 4,994,073 A | 2/1991 | Green | 606/220 |
| 5,002,562 A | 3/1991 | Oberlander | 606/221 |

(Continued)

FOREIGN PATENT DOCUMENTS

DE         44 12 311 A1    10/1995

(Continued)

OTHER PUBLICATIONS

Berman R. Irwin; " Sutureless Laparoscopic Rectopexy for Procidentia : Technique and Implications", Diseases of the Colon and Rectum 35(7): 689-693 (Jul. 1992).

(Continued)

*Primary Examiner*—Henry Bennett
*Assistant Examiner*—Andrea M. Ragonese
(74) *Attorney, Agent, or Firm*—Lowrie, Lando&Anastasi, LLP

(57) ABSTRACT

The systems and methods of the present invention provide for soft tissue reconstruction using a fixation device that coapts two intact anatomic structures to each other. In one embodiment, these systems and methods are used to reconstruct defects or abnormalities in the female pelvic floor by using fixation devices to produce a paravaginal suspension of the affected tissues.

21 Claims, 82 Drawing Sheets

U.S. PATENT DOCUMENTS

| | | | |
|---|---|---|---|
| 5,067,957 A | 11/1991 | Jervis | 606/108 |
| 5,089,009 A | 2/1992 | Green | 606/219 |
| 5,125,553 A | 6/1992 | Oddsen et al. | 227/175 |
| 5,217,472 A | 6/1993 | Green et al. | 606/139 |
| 5,328,077 A | 7/1994 | Lou | 227/175 |
| 5,342,376 A | 8/1994 | Ruff | 606/151 |
| 5,352,229 A | 10/1994 | Goble et al. | 606/72 |
| 5,500,000 A | 3/1996 | Feagin et al. | 606/232 |
| 5,549,619 A | 8/1996 | Peters et al. | 606/151 |
| 5,582,616 A | 12/1996 | Bolduc et al. | 606/143 |
| 5,591,163 A * | 1/1997 | Thompson | 606/29 |
| 5,597,378 A | 1/1997 | Jervis | 606/78 |
| 5,618,311 A | 4/1997 | Gryskiewicz | 606/216 |
| 5,618,314 A | 4/1997 | Harvin et al. | 606/232 |
| 5,730,744 A | 3/1998 | Justin et al. | 606/73 |
| 5,810,851 A | 9/1998 | Yoon | 606/148 |
| 5,954,057 A | 9/1999 | Li | 128/898 |
| 6,039,686 A * | 3/2000 | Kovac | 600/30 |
| 6,044,847 A * | 4/2000 | Carter et al. | 128/898 |
| 6,500,194 B2 * | 12/2002 | Benderev et al. | 606/232 |
| 6,506,190 B1 | 1/2003 | Walshe | |

FOREIGN PATENT DOCUMENTS

| | | |
|---|---|---|
| EP | 0 301 898 A2 | 2/1989 |
| EP | 0 432 320 A1 | 6/1991 |
| EP | 0 585 476 A1 | 3/1994 |

OTHER PUBLICATIONS

Darzi et al.; "Stapled Laparoscopic Rectopexy for Rectal Prolapse", Surg. Endosc. 9:301-303 (1995).

Febbraro, W. et al.; "Faisabilité de la Sacrocoipopexie Vaginale Bilatérale à L'agrafeuse: Etude Prospective des 34 Premiers cas", J. Gynecol. Obstet. Biol. Reprod. 26: 815-821 (1997).

Himpens et al.; "Laparoscopic Rectopexy According to Wells", Surg. Endosc. 13 : 139-141 (1999).

Kessler at al.; "Successful Treatment of Rectal Prolapse by Laparoscopic Suture Rectopexy ", Surg. Endosc. 13: 858-861 (1999).

Munro et al.; " Brief Clinical Report : Laparoscopic Rectopexy ", Journal of Laparoendoscopic Surgery 3(1): 55-58 (1993).

Oster S. and Javert T. C.; " Treatment of the Incompetent Cervix with the Hodge Pessary ", Obstetrics and Gynecology , 28(2): 206-208 (Aug. 1996).

Ostrzensky Adam; " Laparoscopic Paravaginal Repair for Genuine Stress Urinary Incontinence ", The Female Patient 22 31-35 (Jan. 1997 ).

Ostrzensky Adam, " Genuine Stress Urinary Incontinence In Women: New Laparoscopic Paravaginal Reconstruction ", The Journal of Reproductive Medicine , 43 (6): 477-482 (Jun. 1998).

Paraiso et al.; " Laparoscopic Surgery for Enterocele, Vaginal Apex Prolapse and Rectocele"; Int. Urogynecol. J. 10 : 223-229 (1999).

Paraiso et al.; " Laparoscopic Surgery for Genuine Stress Incontinence", International Urogynecology Journal 10: 237-247 (1999).

Paraiso R. F. M. and Falcone T." Laparoscopic Surgery for Genuine Stress Incontinence and Pelvic Organ Prolapse", Chapter 16 pp. 197-209.

Richardson Cullen A. "Paravaginal Repair ", Urogynecology Surgery, pp. 73-80.

Shull et al.; " Transactions of the Twentieth Annual Meeting of the Society of Gynecologic Surgeons"; Am. J. Obstet. Gynecol. 171(6): 1429-1439(Dec. 1994).

White R. G. "Classical Articles Urogynecology", Int. Urogynecol. 8:288-292 (1997).

International Search Report.

VIDEOTAPE Paravaginal Repair and Modified Burch Colposuspension : A Laparoscopic Approach.

* cited by examiner

SYSTEM AND METHODS FOR SOFT TISSUE RECONSTRUCTION

RELATED APPLICATIONS

This application claims priority to Provisional Patent Application 60/127,104, filed Mar. 31, 1999, and also claims priority to Provisional Patent Application 60/154,763, filed Sep. 20, 1999, and Provisional Patent Application 60/163,305, filed Nov. 3, 1999, each naming Peter Rosenblatt as inventor. The contents of these applications are hereby incorporated by reference.

TECHNICAL FIELD

The invention relates generally to the use of soft tissue fixation devices and application instruments and accessories used in reconstructive soft tissue surgery.

BACKGROUND OF THE INVENTION

A number of surgical procedures are well-known in the arts for affixing tissues to each other, thereby repairing their abnormal pathophysiologies. As an example, tissues that have become inordinately lax or stretched or torn can allow structures or organs to become malpositioned, so that their physiologic functions are altered. In certain body areas, the malposition of a structure due to loss of regional support is referred to as "ptosis," although this term may not be generally used to refer to malposition in certain other body areas, such as the female pelvis. A situation of tissue or organ malposition due to loss of regional support is seen in pelvic conditions such as cystoceles and rectoceles, as well as in frank uterine prolapse or vaginal vault prolapse. Repairing lax, torn or stretched tissues in general may be termed a "pexy." As another example wherein tissues are affixed to each other to repair their abnormal physiologies, a surgeon may attach two tissues to each other in a non-anatomic relationship to repair an organ's abnormal physiology, as is seen in a Nissen fundoplication for esophageal reflux.

There are many devices found in the patent literature which describe a variety of surgical instruments and fasteners used in the fixation of tissue. The following U.S. patents are examples of the art of vaginal reconstructive surgery: U.S. Pat. No. 4,196,836 to Becht, U.S. Pat. No. 4,261,244 to Becht and Rothfuss, U.S. Pat. No. 4,424,810 to Jewusiak, U.S. Pat. No. 4,934,364 to Green, U.S. Pat. No. 5,125,553 to Oddsen and Ger, and U.S. Pat. No. 5,217,472 to Green, et al. All patents, patent applications and publications referenced herein are hereby incorporated by reference.

Procedures to manipulate soft tissues, thereby to repair laxities or correct other physiological abnormalities, may be performed using either open techniques, wherein a skin incision is made and dissection is carried into the deeper layers of the body until the relevant organs are reached, or using laparoscopy or other minimally invasive techniques, wherein small skin incisions are used for the insertion of various visualizing, manipulating, cutting and suturing tools to reach the involved organs. In all these cases, extensive dissection and manipulation may be required to identify, free up and suture together the tissues, with the accompanying scarring, devascularization, denervation and risk of prolonged anesthesia and possible blood loss.

Laxities in the female pelvic floor provide an example of an anatomic situation where tissue stretch, tearing or relaxation can lead to physiological abnormalities. Defects in this area may be related to past pregnancies and childbearing, or may be related to loss of soft tissue tone after menopause or with aging. Whatever their etiologies, these defects may result in a variety of urogenital abnormalities, such as cystoceles, rectoceles, vaginal prolapse and genuine stress urinary incontinence. Surgical treatment of this condition may be necessary in up to 11% of the female population; there is presently about a 30% failure rate to such surgery, leading either to further surgery or to alternative treatment with appliances such as vaginal pessaries. Either a vaginal, an open or a laparoscopic approach can be used to perform soft tissue reconstruction in this area. When traditional surgical techniques are used to treat laxities in the female pelvic area, incisions may need to be made in the vaginal mucosa and dissection may need to be carried into the spaces between adjacent organs such as the bladder and rectum, which may lead to blood loss, scarring, denervation, and an unacceptably high failure rate. Laparoscopic procedures directed to this anatomic region have both advantages and disadvantages: advantages include improved visualization of particular areas of the pelvic anatomy, shortened hospitalization, decreased postoperative pain and more rapid recovery; disadvantages include the technical difficulties of the dissection, increased operating time and increased hospital cost due to the length of surgery. (MF Paraiso, T Falcone and MD Walters, "Laparoscopic surgery for genuine stress incontinence," Int. Urogynecol J. 10:237–247, 1999).

Whether surgery is performed using a vaginal, an open or a laparoscopic approach, identification of the anatomic defects to be repaired is crucial. As an example, those laxities of female pelvic area leading to genuine stress urinary incontinence may involve the various suspensory and supporting elements of the vagina, bladder, urethra and neighboring structures. (A Ostrzenski, "Laparoscopic paravaginal repair for genuine stress urinary incontinence," The Female Patient 22: 31–35, 1997) One of these structures, the pubocervical fascia, can have four types of damage: lateral superior paravaginal, transverse, distal and central. (A C Richardson, J B Lyon, N L Williams, "A new look at pelvic relaxation," A . J. Obstet. Gynecol. 126:568, 1976).

Vaginal repair of laxity of the anterior vaginal wall (or cystocele) has traditionally involved a procedure called an anterior colporrhaphy (or anterior repair). This technique involves opening the space between the vaginal mucosa and bladder, plicating the tissue under the bladder to create support, trimming off the excess vaginal mucosa, and the reapproximating the mucosal edges. This technique, however, assumes that the anatomic defect is an attenuation of the tissues under the bladder, the endopelvic fascia. Anatomic studies have demonstrated, however, that in most cases, the true anatomic defect is actually a paravaginal defect, that is, a loss of attachment of the superior lateral sulci of the vagina to the pelvic sidewall, at the level of the arcus tendineous fascia pelvis, or "white line". (A C Richardson, "Paravaginal repair," pp. 73–80 in *Urogynecological Surgery*, ed. W G Hurt, Aspen Medical Publishers, Gaithersburg, Md., 1992) It is estimated that over 80% of cystoceles are caused by this defect.

A suitable operation for such a defect is a paravaginal repair. This technique was originally described via a vaginal route by George White, in 1909, but today is more commonly performed abdominally, through a laparotomy incision. The procedure, whether performed via an abdominal, laparoscopic or transvaginal route is technically demanding and has therefore not gained widespread acceptance in the gynecologic community. There remains a need in the art, therefore, for tools and methods that would facilitate this type of soft tissue repair within the female pelvis.

There exists further in the art a need for systems and methods to facilitate soft tissue repair by the affixation of adjacent or related structures, thereby to treat the variety of physiological disorders related to soft tissue laxity and the variety of physiological disorders treatable by buttressing an abnormal structure with adjacent soft tissues. There remains a further need in the art for devices that may be used to coapt soft tissues tightly enough to hold them in place but not so tightly as to cause damage thereto. It is particularly desirable that a device applied to affix soft tissues be removable without causing significant local trauma, in case the device is initially malpositioned or in case the device needs to be removed during a later surgical revision.

A number of tools and methods are known in the art that relate to the repair of soft tissues that have been disrupted by surgery or trauma, for example for the repair of incisions or lacerations. These tools and methods may not be well adapted for addressing the abovementioned clinical problems, where intact soft tissue structures are to be affixed to each other. There remains a need in the art for a system of soft tissue coaptation suitable for holding intact structures to each other, where significant wound healing processes would not be triggered by the specific defect being repaired. Where the anatomic defect being repaired does not trigger wound healing processes, the physician cannot rely upon those natural processes to add strength to tissue coaptation. Therefore, a system to hold intact soft tissue structures together would advantageously provide sufficient force to hold the intact structures together and thereby to overcome the regional laxity, and would furthermore provide a repair of sufficient duration that the previously lax tissues would remain in their repaired positions.

SUMMARY OF THE INVENTION

The present invention consists of various designs of tissue holding devices (fixation devices), application instruments and positioning accessories wherein the device fixes tissues in a position that approximates their original position prior to damage caused by local trauma, stress or by the loss of strength with aging.

In addition to the fixation device and applicator, the invention also includes a series of templates used to guide the accurate positioning of the applicator therein ensuring the desired delivery and placement of fixation devices. In one embodiment, a template formed according to the present invention may be used for diagnosis of certain defects of the pelvic floor, by replicating forces that would be applied to the pelvic floor defect through a paravaginal repair.

The present invention further includes methods for soft tissue reconstructive surgery whereby intact soft tissues are coapted and affixed in the coapted position by a soft tissue fixation device. In one embodiment, these methods are directed to the reconstruction of female pelvic floor defects, wherein the lax tissues of the pelvic floor are suspended by coapting tissues adjacent to the lateral vaginal sulcus to the arcus tendineus fascia pelvis.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The following figures depict certain illustrative embodiments of the invention in which like reference numerals refer to like elements. These depicted embodiments are to be understood as illustrative of the invention and not as limiting in any way.

DETAILED DESCRIPTION OF THE INVENTION

Figure 1A:
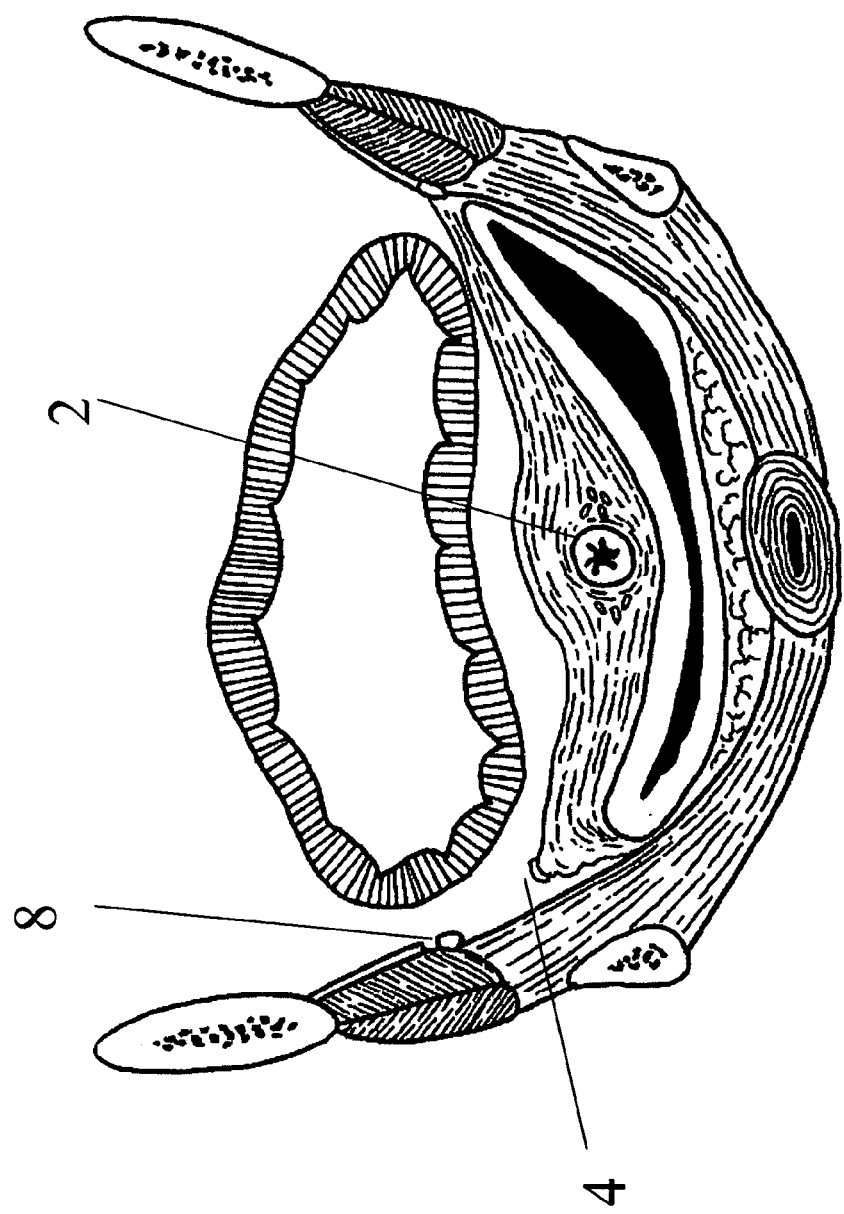
FIGS. 1A and B depict generically a soft tissue structure undergoing soft tissue reconstruction.

The invention will now be described with reference to certain illustrated embodiments and certain exemplary practices. Specifically, the invention will be described hereinafter in connection with soft tissue reconstructive medical procedures, described in more detail below, and with urogynecological reconstruction. However, it should be understood that the following description is only meant to be illustrative of the invention and is not meant to limit the scope of the invention which is applicable to other forms of soft tissue reconstruction, as will be evident to practitioners in the art. The systems and methods of the present invention provide generally for soft tissue reconstruction. As used herein, the term soft tissue reconstructive surgery relates to those conditions characterized by abnormal positioning of normal tissues or characterized by tissue or anatomic abnormalities that result in malposition of anatomic organs or structures, or to those conditions wherein it is desirable for the patient's well-being to reposition or recontour a normally positioned soft tissue structure or organ. As examples, soft tissue reconstructive surgery or soft tissue reconstruction may include the variety of suspensions, pexies and lifts performed in different anatomic regions. Soft tissue reconstruction may also include a procedure like gastric stapling where the shape of the stomach is altered to treat morbid obesity. Further, soft tissue reconstruction may be applied to procedures like Nissen fundoplications where the normal anatomy of a soft tissue structure or an organ is altered in order to treat a functional or physiological abnormality. As understood herein, the term soft tissue structure may refer to any identifiable tissue area, organ or organ component that is made of soft tissues. For example, an identifiable area of thickened fascia, such as the conjoint tendon, may be called a soft tissue structure; similarly, a viscus, a body lumen, a muscle or other tissue areas, organs or organ components may be termed soft tissue structures. As used herein, the abbreviation ATFP will be used to refer to the arcus tendineus fascia of the pelvis.

The systems and methods of the present invention relate to the coaptation of intact soft tissue structures. These are structures which have not been traumatized, incised or divided surgically. In some cases, the present invention may be used to hold together two soft tissue structures by approximating their serosal surfaces. In other cases, the present invention may be used to fix a soft tissue structure with an epidermal or mucosal external surface to a deeper soft tissue structure, so that the distal end of the fixation device is buried in the deeper soft tissue. These features make it desirable that the fixation devices according to the present invention are adapted for approximating tissue without applying undue force that would necrose the points of each tissue that are being brought into proximity.

In addition, the fixation devices according to the present invention are advantageously adapted so that they can secure a superficial tissue to a deeper tissue without requiring that the surgeon access the deeper tissue or access a surface on the distal aspect of the deeper tissue to position the fixation device properly or to affix it in position. In certain embodiments, the entire fixation device may be buried in the soft tissues. In other embodiments, the proximal end of the fixation device may be visible or palpable on an external aspect of a soft tissue. The fixation devices, as exemplified herein, may be adapted for particular anatomic uses, so that their proximity to adjacent structures does not damage the structure, or does not cause the patient pain or discomfort.

While affixation devices according to these systems and methods are not adapted for the repair of traumatic or surgical wounds, they may take advantage of wound healing processes stimulated by their presence. For example, an affixation device may be made of biocompatible, biodegradable materials whose local presence stimulates tissue ingrowth and wound healing processes, thereby forming scar tissue. As another example, an affixation device may be coated with materials that would encourage tissue ingrowth or that would stimulate scarring or epithelialization. Positioning the affixation devices may of itself induce some local tissue trauma that will stimulate reparative processes such as wound healing. This may take place by local irritation or by the presence of a material or a surface treatment on the device that stimulates collagen deposition or inflammation with subsequent scar tissue formation. The tensile strength produced by local reparative processes may, in certain embodiments, complement the tensile strength produced by the adherence of the fixation device in the soft tissue structures. In other embodiments, however, the fixation device itself, multiply or singly applied, will grasp the tissues with sufficient force and durability to hold the soft tissues in their preselected position. General principles of surgical judgment will guide the practitioner in determining the number of fixation devices to use for a particular application, and in determining their optimal insertion sites. In certain embodiments of the systems and methods of the present invention, templates may be provided that will guide the placement of the fixation devices into anatomically correct areas. Examples of templates will be illustrated below. Templates may further be used diagnostically, so that the positioning of a template within the vaginal vault in the office may replicate the tissue positioning that would be performed during a soft tissue reconstructive procedure. In the case of a cystocele or other pelvic floor abnormality, the positioning of the template may serve to reduce the defect to its anatomic position, and may thereby confirm the diagnosis of the underlying anatomic condition, and furthermore may justify operative intervention using the systems and methods disclosed herein. In other embodiments of these systems and methods, various diagnostic modalities may be used to identify the anatomic structures and tissues into which or through which a fixation device is to be inserted. Representative diagnostic modalities include MRI, fluoroscopy, CT scan, conventional radiology, ultrasound, laparoscopy and endoscopy, although other modalities may be or may become apparent to practitioners of ordinary skill in the art. In certain embodiments of these systems and methods, furthermore, various modalities may be used to guide the placement of a fixation device through and into the appropriate anatomic structures. Representative modalities include MRI, fluoroscopy, CT scan, conventional radiology, ultrasound, laparoscopy and endoscopy, direct visualization (for example through a vaginal speculum or through an open laparotomy incision), and intraoperative palpation, through a pre-formed surgical incision or through an incision created specifically to admit the surgeon's palpating finger or hand. Appropriate guiding modalities will be evident to surgical practitioners, based on the anatomic area under consideration.

FIG. 1A depicts generally a generic defect, corresponding to no specific anatomic region, appropriate for repair according to these systems and methods. In this figure, the soft tissue structures being coapted are in contiguity with each other in the native anatomic state. The term contiguity refers to physical proximity, including adjacency. The native anatomic state is understood to be the natural anatomic position. By contrast, tissues that have been moved, either traumatically or iatrogenically to a different position than the natural anatomic one are not considered to be in the native anatomic state. In addition, a congenital anomaly producing a malposition of a soft tissue structure shall be understood to involve tissues not in their native anatomic state.

Figure 1B:
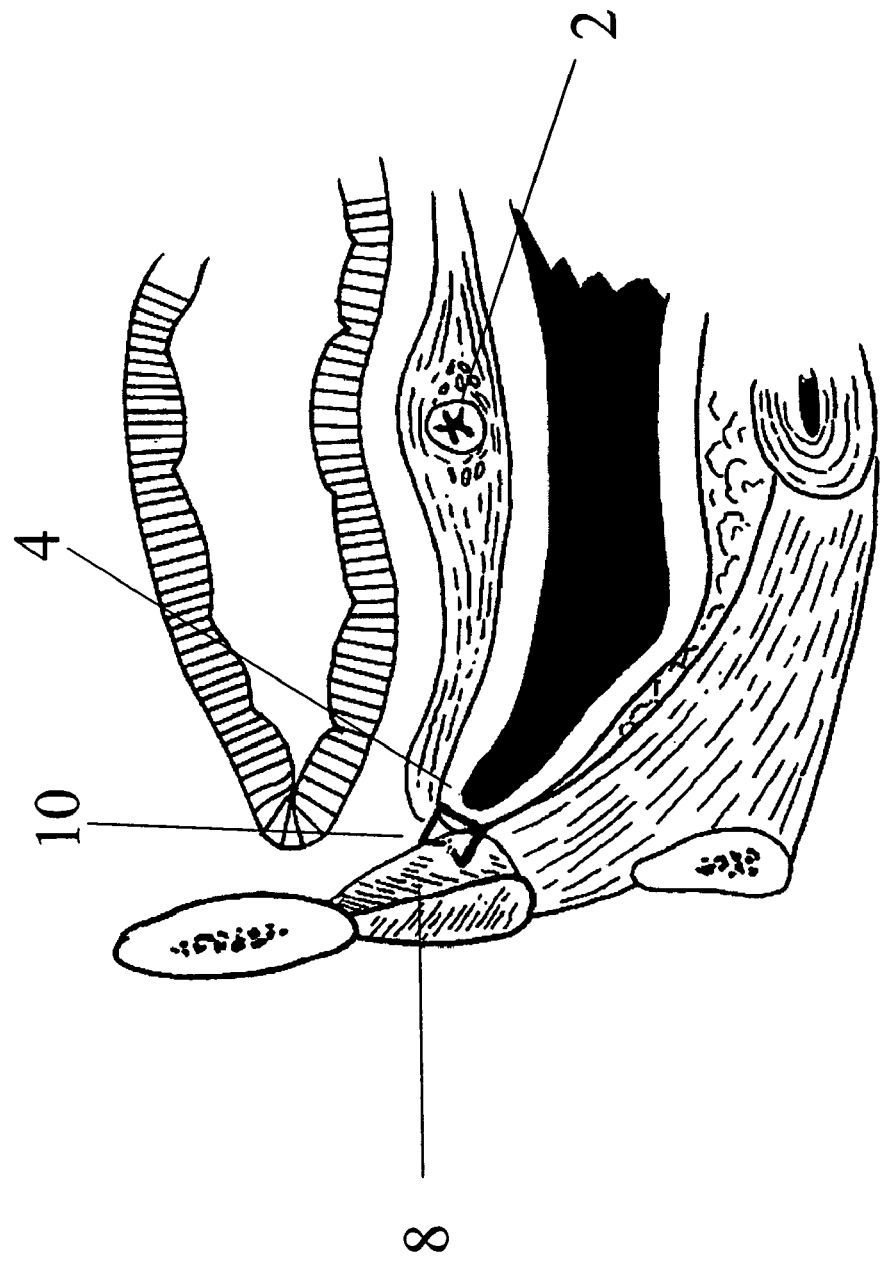

FIG. 1A shows a ptotic structure 2 which has assumed an abnormal position due to the laxity of the lax tissue 4 which is intended to support the structure 2. Because of the attenuation, stretching or damage to the lax tissue 4, the ptotic structure 2 rests in an abnormal position which leads to its physiological dysfunction. As an example, the ptotic structure 2 may be a conduit or body lumen like the urethra or the rectum; in these cases, the physiological function being disrupted may be the normal passage of body fluids or the subject's control over the passage of body fluids. In another example, the ptotic structure 2. may be an anatomic region such as the inguinal canal; the physiological function being disrupted may be the support for the lower abdominal wall structures and the maintenance of anatomic integrity to the lower abdominal wall. FIG. 1A further shows a supportive tissue 8 identified by the surgeon as a stable structure or anatomic region with sufficient strength to permit the lax tissue 4 to be coapted thereto, thereby to support the ptotic structure 2. FIG. 1B shows an embodiment of the present invention wherein the structure 2, formerly ptotic, has now been supported by a pexy or a plication of the previously lax tissue 4 through the placement of a fixation device 10 that is inserted through the lax tissue 4 into the supportive tissue 8.

The embodiment illustrated in FIGS. 1A and B may relate to any body area where a structure 2 has assumed an anatomically abnormal position. The lax tissue 4 may be approached using conventional open surgical methods, or endoscopic methods or transmucosal or transcutaneous methods. The fixation device may assume a plurality of shapes, adapted for insertion in a specific tissue. The present invention relates to those systems and methods used for holding intact soft tissue structures together. In one embodiment, these systems and methods may be used to suspend one tissue from another, thereby to support the first tissue and further to support structures in anatomic and physiologic relation thereto. A structure in anatomic relation to another structure may be one where the first structure is in proximity to or in continuity with the second structure, or where a force applied to the first structure is transmitted to the second structure, to affect its shape or position. A structure in physiologic relation to another structure may be one where the physical relation of the first structure to the second is important for the normal physiological functioning of said second structure.

The soft tissue structures that are coapted according to these systems and methods may rely upon a fixation device that is inserted from a first anatomic soft tissue structure to a second anatomic soft tissue structure. The fixation device is contained within each soft tissue structure, either wholly or partially residing within both soft tissue structures. A fixation device according to these systems and methods need not reside fully within either soft tissue structure. For example, a part of it may be external to one or the other soft tissue structure, or a part may reside within a third or a fourth soft tissue structure. In certain embodiments, a fixation device may be coated with agents or provided with surfaces intended to promote epithelial overgrowth of the device. As examples, coatings with collagen, growth factors or adhesion ligands may be provided. As further examples, the surface of the fixation device may be textured or roughened to provide a platform for epithelialization.

Figure 2:
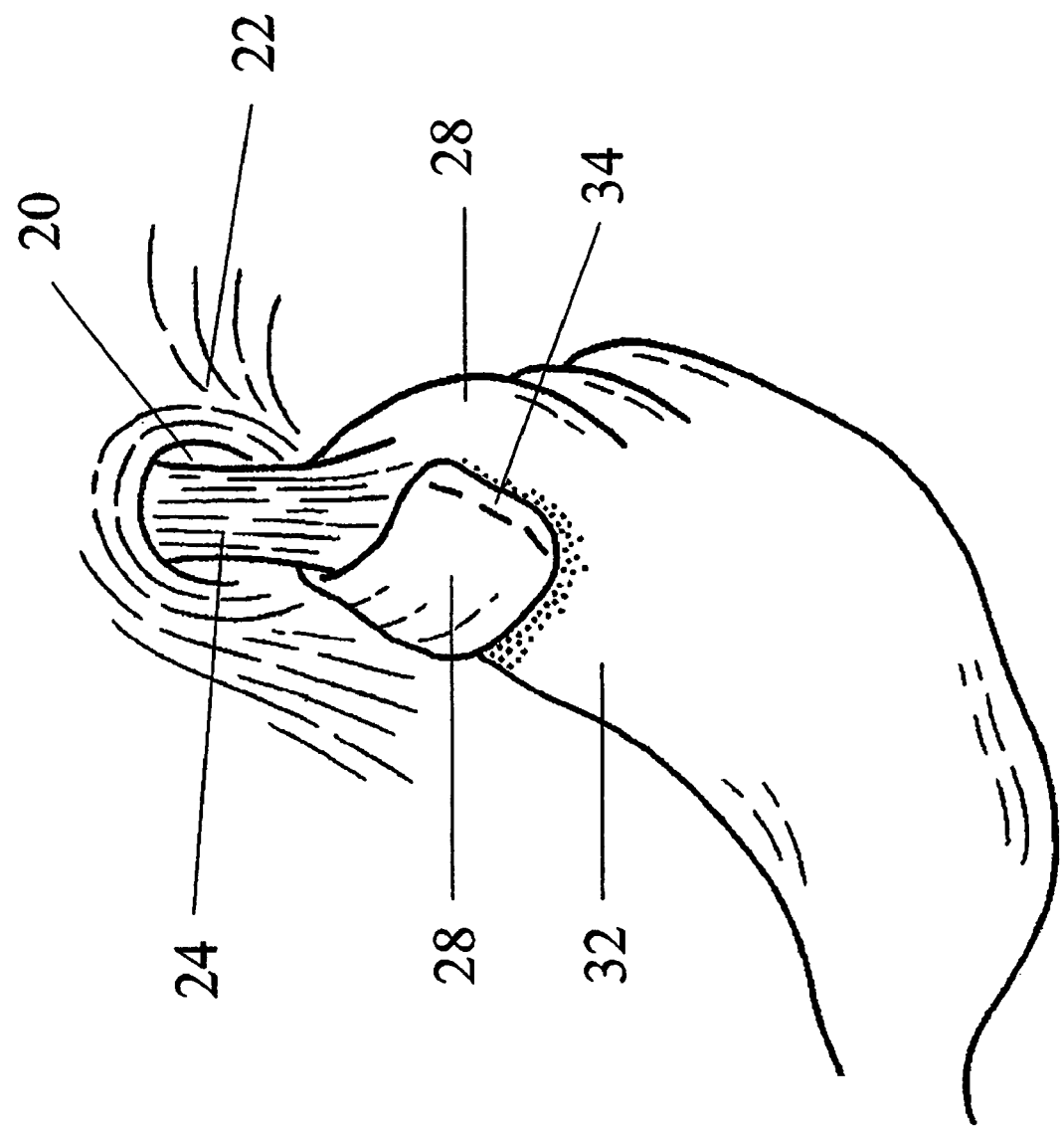
FIG. 2 depicts an embodiment of the present systems and methods used for Nissen fundoplication.

FIG. 2 shows schematically the use of soft tissue fixation devices according to these systems and methods to perform an approximation of intact tissues for a soft tissue reconstruction of an anatomic abnormality leading to esophageal reflux. In this figure, a Nissen fundoplication is schematically represented. The figure shows a defect 20 in the diaphragm 22 representing a hiatal hernia, an anatomic defect responsible for esophageal reflux. As depicted herein, a Nissen fundoplication has been performed, as is familiar to surgical practitioners. The figure shows that the proximal gastric fundus 28 has been wrapped around the stomach 32 and esophagus 24 at the level of the gastroesophageal junction 30, and the fundus 28 has been fixed to itself. A row of fixation devices 34 has been used to accomplish the fixation of the intact gastric fundus 28 to the anterior wall of the stomach 32, thereby resisting the pathophysiological abnormalities accompanying symptomatic hiatal hernia. Fixation devices useful for this procedure may be designed to approximate the intact structures gently, so that their blood supplies are not compromised, and so that their intact edges are not subject to pressure necrosis. Fixation devices useful for this procedure may be made of any biocompatible material, although the use of metallics for abdominal surgical fixation is well-known and well established in the art. Fixation devices useful for this procedure furthermore may be designed not to penetrate the full thickness of the stomach, but rather to reside within the muscle layer, so that the passages within which the fixation devices are located do not provide portals of entry for gastric juices and bacterial contamination. Shapes suitable for this and other procedures may be selected according to these anatomical needs. Embodiments of suitable fixation devices are described below. Other appropriate modifications will be readily envisioned by practitioners of ordinary skill in the relevant arts.

It will be understood by skilled artisans that it is advantageous to provide a way for guiding the fixation devices into the appropriate anatomic location. In one embodiment, a template may be provided to show the operator the preferred placement of the fixation devices. In other embodiments, application of fixation devices for soft tissue reconstruction can be guided by other surgical methods, such as palpation of landmarks through a small incision, or such as laparoscopic or endoscopic visualization. Other modalities, such as fluoroscopy, CT scan, MRI or other radiological methods, may be employed for guiding the surgeon in positioning the fixation devices.

It will be understood by skilled artisans that it is advantageous to provide a fixation device that can be readily extracted from tissues in case it needs to be repositioned or removed entirely. Fixation devices that are malpositioned may need to be repositioned. Fixation devices that are unsuccessful or are causing symptoms by their presence may need to be removed. Since the fixation devices according to the present invention are inserted into intact tissues, it is desirable that their removal will be accomplished without undue trauma to the approximated tissues. As understood herein, the process of implanting and removing fixation devices involves generally a manipulation of the devices, which may take place manually by the operator, or may take place by using a tool. Fixation devices are both implanted and removed by a manipulation. Furthermore, according to the present invention, a variety of fixation devices may be contemplated that are appropriate for various anatomic areas. Certain embodiments are presented below that demonstrate these and other features, although the depicted embodiments are understood to be illustrative only. Other modifications will be readily envisioned by practitioners of ordinary skill in the art, said modifications to fall within the scope of the present invention as disclosed herein.

Figure 3:
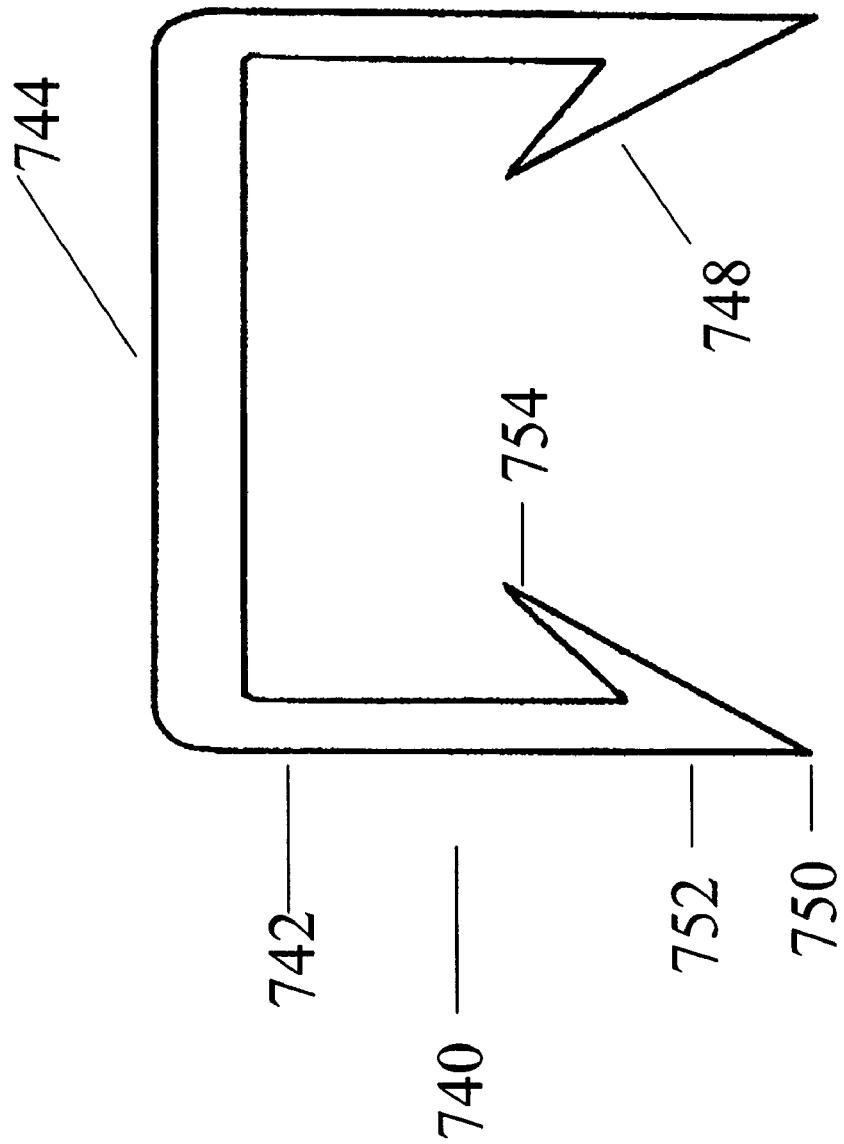
FIG. 3 shows an embodiment of a fixation device according to the present invention.

In an illustrative embodiment, depicted in FIG. 3, a fixation device 740 is shown that may be placed vaginally or laparoscopically using an insertion device to perform a paravaginal repair, reapproximating the superior lateral sulci to the ATFP according to the systems and methods of this invention. Furthermore, the depicted embodiment may be used for fixation of other soft tissues, according to systems and methods disclosed herein. The depicted fixation device 740 is formed with a horizontal bar 744 with a vertical arm 742 at each end forming substantially a right angle to the bar 744. The distal end 752 of each vertical arm 742 bears a barb 748 with a distalmost insertion point 750. In the illustrated embodiment, the barb 748 includes a proximally oriented member 754 that may hook into the tissues and anchor the fixation device 740 in the appropriate anatomic site. While the illustrated embodiment is drawn to show the members of the fixation device 740 in a fixed relationship to each other, a number of modifications may be readily envisioned by practitioners of ordinary skill whereby the barbs 748 may be flexible or may change in their relationship to the vertical arm 742. Other modifications for barbed fixation devices according to these systems and methods have been disclosed in certain preceding figures. As will be apparent to practitioners of ordinary skill in these arts, the modifications introduced for fixation devices as described above can be readily applied to fixation devices adapted for intravaginal use. As examples of advantageous modifications for transvaginal fixation devices, the horizontal bar 744 of the fixation device 740 could be made of an absorbable (such as polyglycolic acid or polydioxone) or nonabsorbable material. The surface of the device could be formed or coated to encourage reepithelialization by the vaginal mucosa as described above. The fixation device 740 can be inserted by an applicator either across intact epithelium or through an insertion incision. If an insertion incision is made, tissue elasticity and wound healing may combine to re-form an intact epithelial covering over the fixation device. Besides the embodiment shown in FIG. 3 other embodiments, illustrated below, may be readily adapted for use in this anatomic area. Modifications of the depicted embodiments may be undertaken by those of ordinary skill in the art, said modifications being encompassed by the scope of the present invention.

Figure 4A:
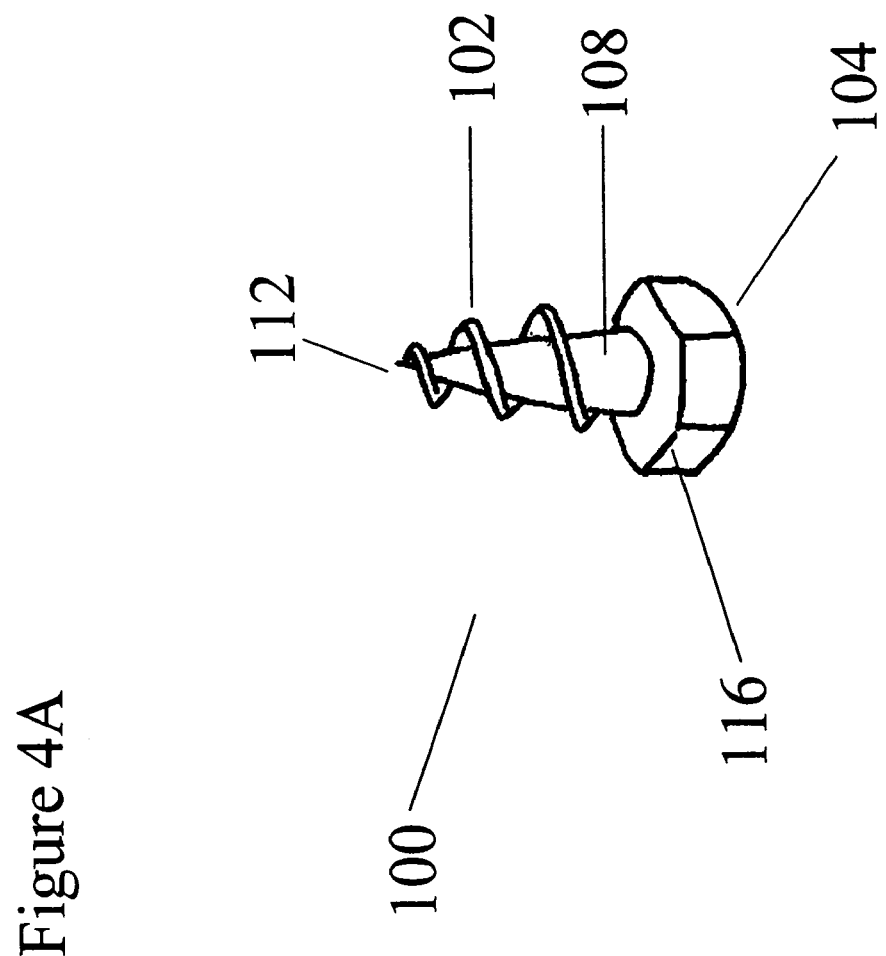
FIGS. 4A–C depict embodiments of fixation devices according to the present invention.
Figure 4B:
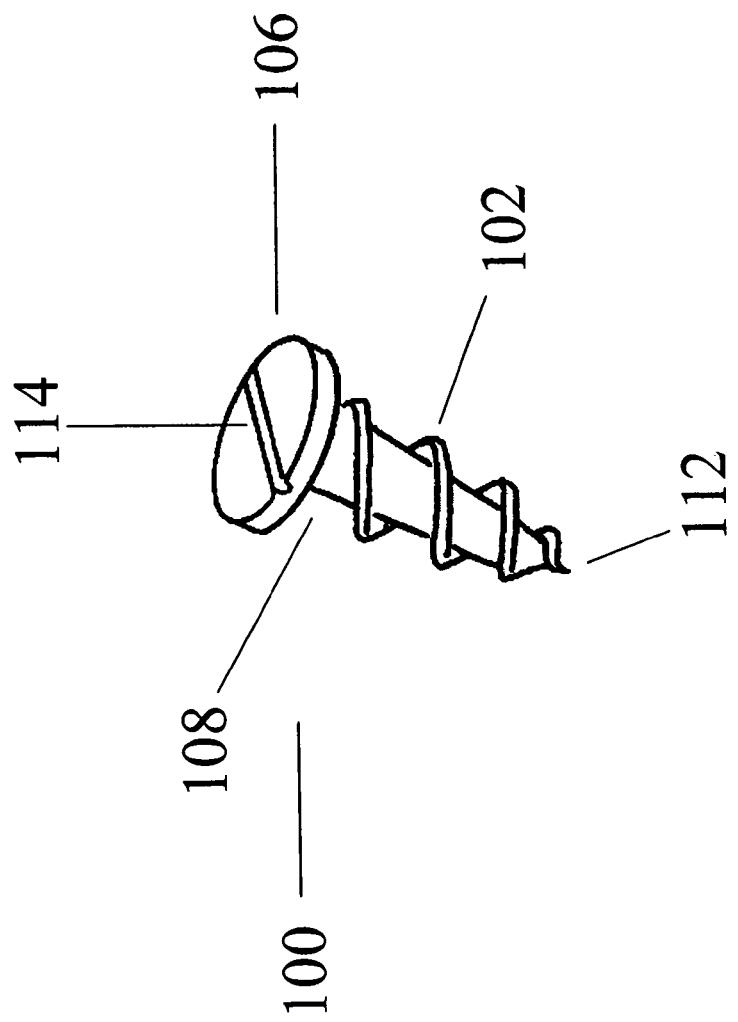
Figure 4C:
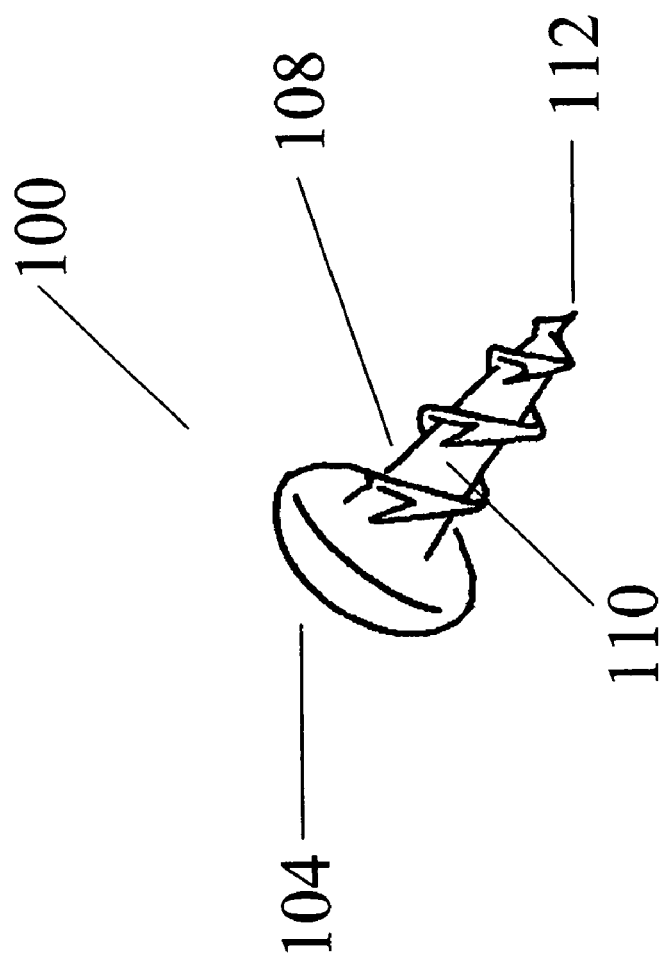

FIGS. 4A–C shows several embodiments of fixation devices configured as screws. FIGS. 4A and B depict a screw 100 sized for a particular anatomic region wherein it will be positioned to grasp an intact tissue. The depicted embodiment comprises a shaft 108 with screw threads 102 disposed thereupon and an insertion point 112, so that the screw 100 can penetrate a first tissue and obtain purchase in a second tissue, thereby to fix the two together. FIG. 4A shows a rounded head 104 on the screw 100. FIG. 4B shows a flat head 106 on the screw. Head shapes and sizes may be selected for particular anatomic areas. A screw 100 may be inserted into the tissue using a tool adapted for this purpose. In FIG. 4A, the screw head 104 has a circumferential row of ridges 116 that can engage an insertion tool. In FIG. 4B, the screw head 106 has a driving slot 114 that can accept a tool configured like a screwdriver. Other insertion arrangements will be readily envisioned by practitioners in the art. FIG. 4C a screw 100 with a set of circumferential barbs 110 intended to engage tissue as they are pushed in. The insertion point 112 permits the screw 100 to penetrate the tissue, and the circumferential barbs hold the tissue as the screw 100 is progressively pushed deeper. Screws 100 may be fabricated of various materials, depending upon the anatomic area in which they are to be used. They may be made of metallics, ceramics, polymers or other materials, for example. Furthermore, they may be composed wholly or in part of absorbable materials. Furthermore, the screw head may be countersunk through an incision that is formed to allow the screw head to sink below the overlying epithelium, so that the screw head is buried and covered with epithelium. This countersinking may similarly be applied to proximal portions of other fixation devices, such as certain embodiments described or depicted below.

Figure 5A:
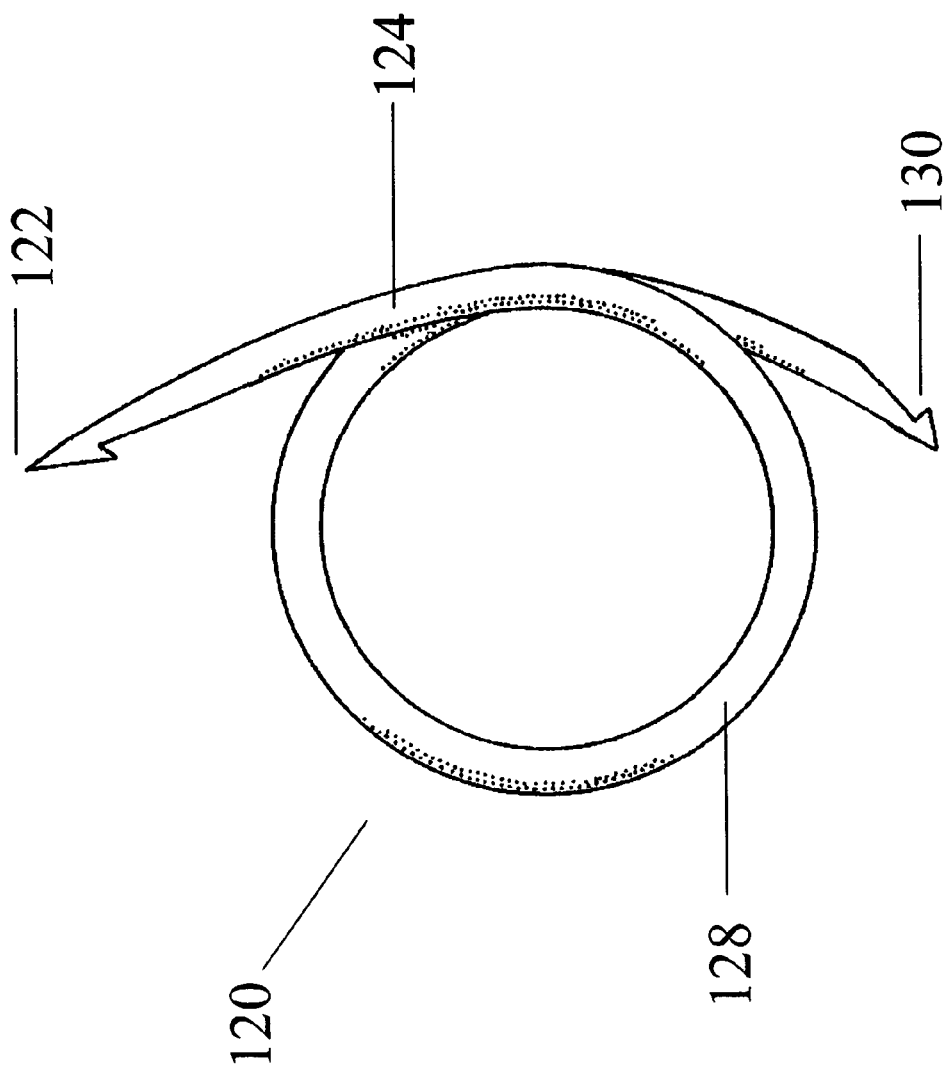
FIGS. 5A and B depict embodiments of fixation devices according to the present invention.
Figure 5B:
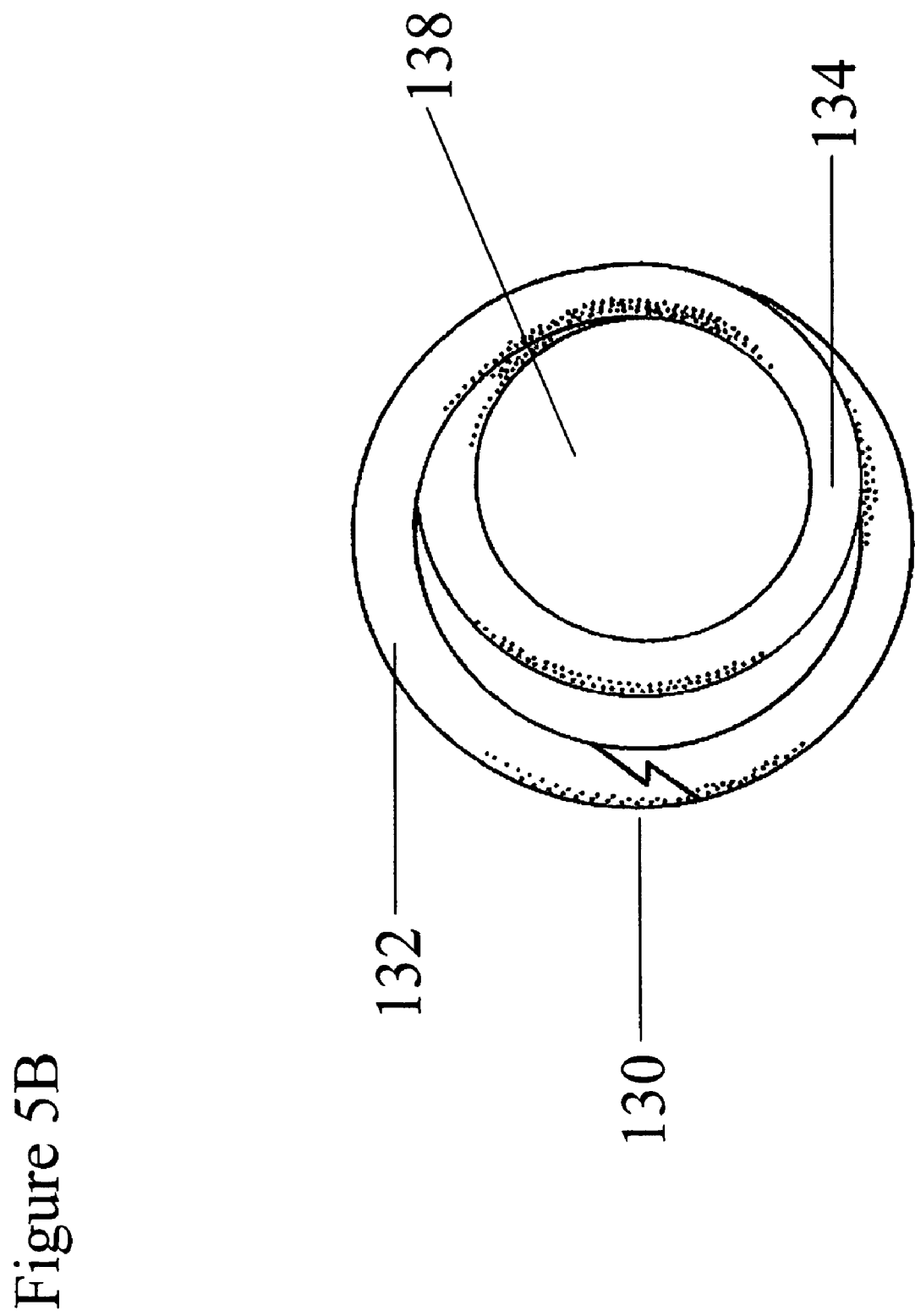

FIG. 5A shows an embodiment of a screw shaped as a coil 120 that can be used for tissue fixation according to these systems and methods. In FIG. 5A, an insertion point 122 is adapted for penetrating the tissues to allow the flexible member 124 to be inserted therein. A screwing motion may be used to engage the anchoring tissues, or a motion similar to that used to insert a curved needle bearing a suture. In one embodiment, the insertion point 122 is directed distally through the anchoring tissue and then is redirected proximally, to be grasped by the operator. The curve 128 of the coil 120 is shaped to facilitate the encircling of the target tissue. Once the insertion point 122 has been redirected proximally and retrieved by the operator, it may be inserted into the latch 130 at the proximal end of the coil 120. As shown in FIG. 5B, this forms an outer ring 132 around an inner ring 134, with the target tissue 128 within these rings. To remove the device, the outer ring 132 can be disarticulated by removing the insertion point 122 from the latch 130, and then backing the coil out through the target tissue 138. Embodiments using the coil shape or modifications thereof may advantageously use flexible materials, whether metallic or polymeric. In certain embodiments, shape memory alloys may be used to achieve configurations such as those depicted in these figures, as will be readily apparent to artisans of ordinary skill in the art. The use of shape memory alloy (SMA) and the particular use of stress-induced martensite (SIM) alloy has been described in U.S. Pat. Nos. 4,505,767 and 5,597,378, the disclosures of which are incorporated herein by reference.

Figure 6A:
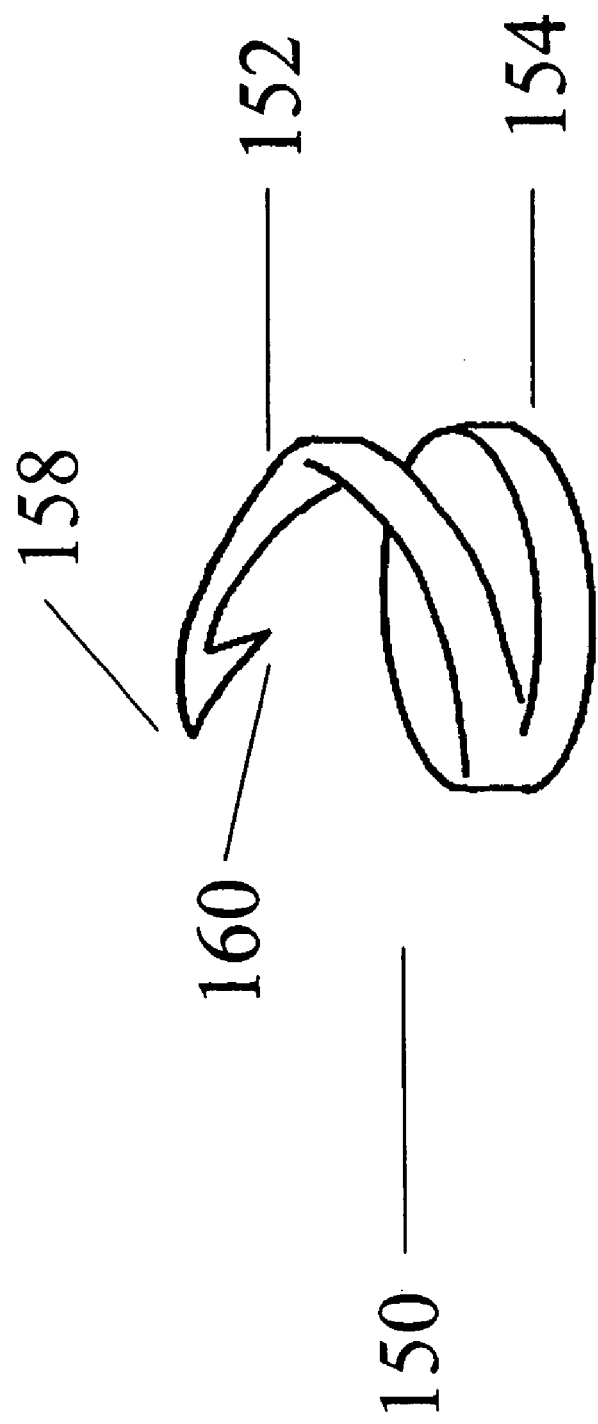
FIGS. 6A and B depict embodiments of fixation devices according to the present invention.
Figure 6B:
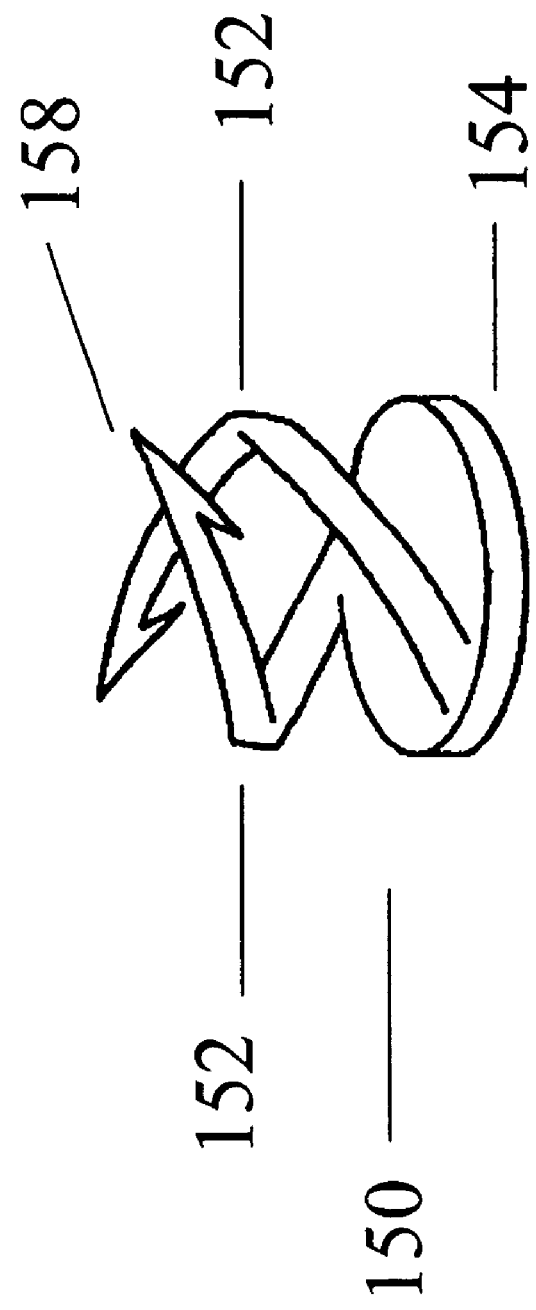

FIG. 6A shows a screw 150 with a single arm 152 extending distally from a base coil 154 that supports it. An insertion point 158 is available to penetrate the tissues as the screw 150 is inserted. A barb 160 anchors the screw 150 into the anchoring tissue, while the base coil 154 exerts pressure on the proximal tissue to affix it to the anchoring tissue. In FIG. 6B, a screw 150 is seen with a double arm 152 design, one arm being placed posterior to the other and both affixed to an anchoring coil 154. In one embodiment of the screw 150 shown in FIG. 6B, the arms 152 are made from flexible materials so that they can be manipulated so as to attain purchase on the correct anchoring tissue. Materials suitable for the screws 150 depicted in these figures may include metallics, polymers, ceramics or other materials adapted for a particular anatomic region. Furthermore, the screw 150 may be absorbable in whole or in part.

Figure 7A:
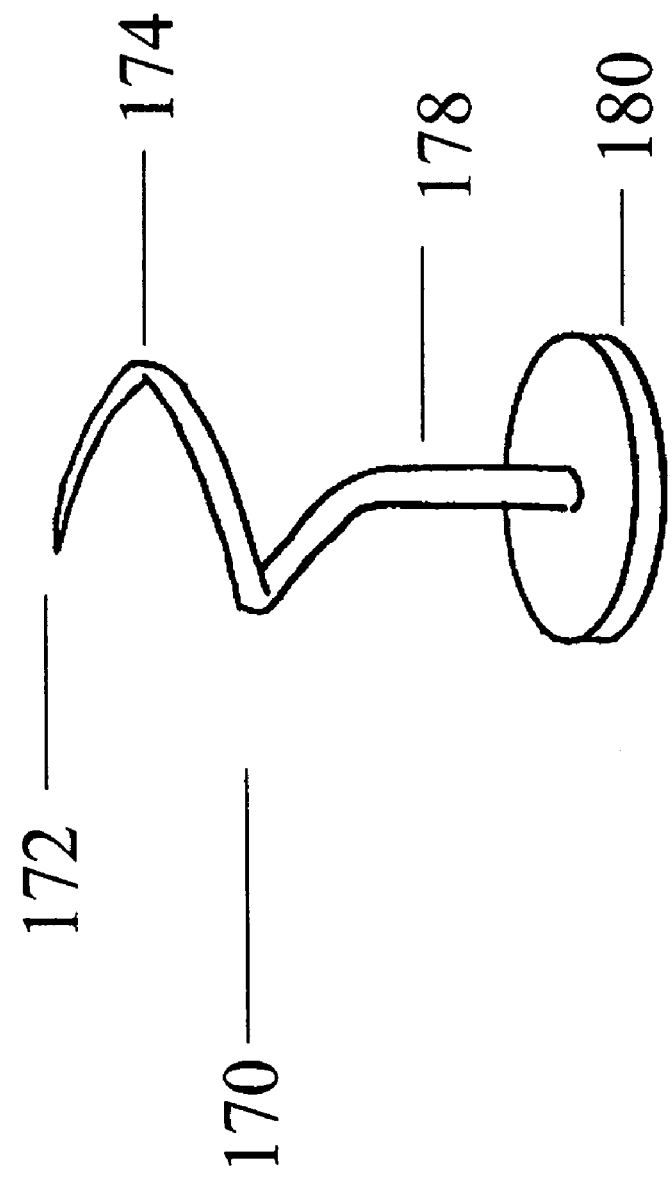
FIGS. 7A and B depict embodiments of fixation devices according to the present invention.
Figure 7B:
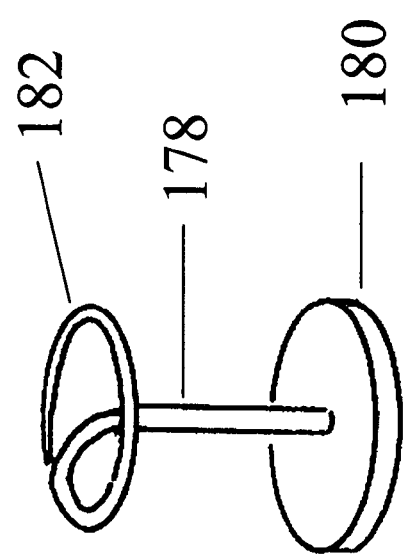

FIG. 7A shows a screw 170 comprising a coil 174 extending outward from a shaft 178, the shaft 178 being affixed to a support plate 180. An insertion point 172 is available for penetrating the outer layer of tissues. In the depicted embodiment, a SMA or a SIM may be used to form the coil 174, so that after insertion the coil 174 closes itself upon itself to form a ring 182, as shown in FIG. 7B. The ring 182 is formed after the screw 170 has been positioned within the appropriate tissue. When the ring 182 forms, it serves to encompass the insertion point 172 so that the insertion point 172 does not continue to penetrate tissues. The support plate 180 puts pressure on the first layer of tissues to allow them to be held in approximation to a second layer of tissues within which the ring 182 has formed.

Figure 8A:
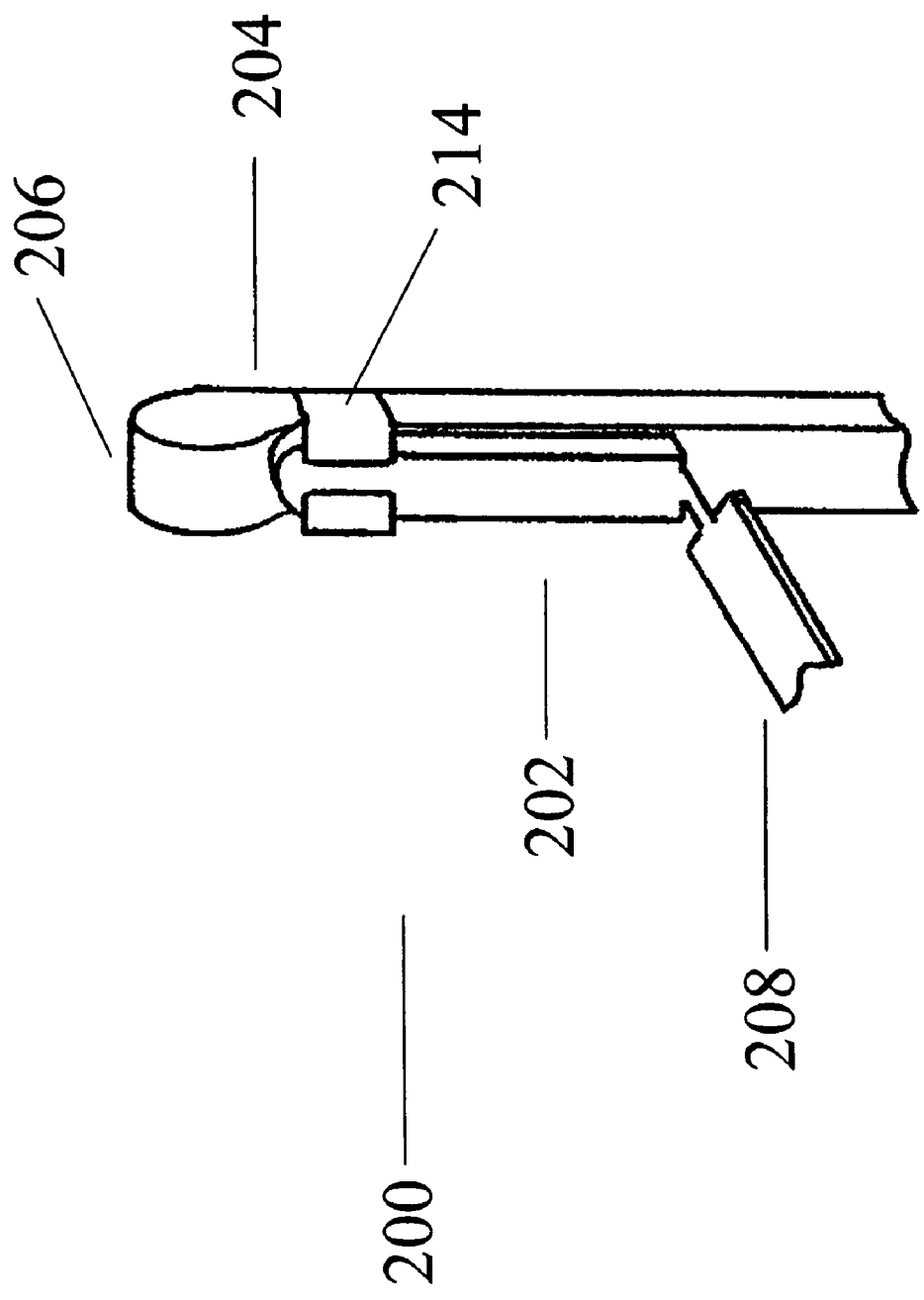
FIGS. 8A–C depict embodiments of fixation devices according to the present invention.
Figure 8B:
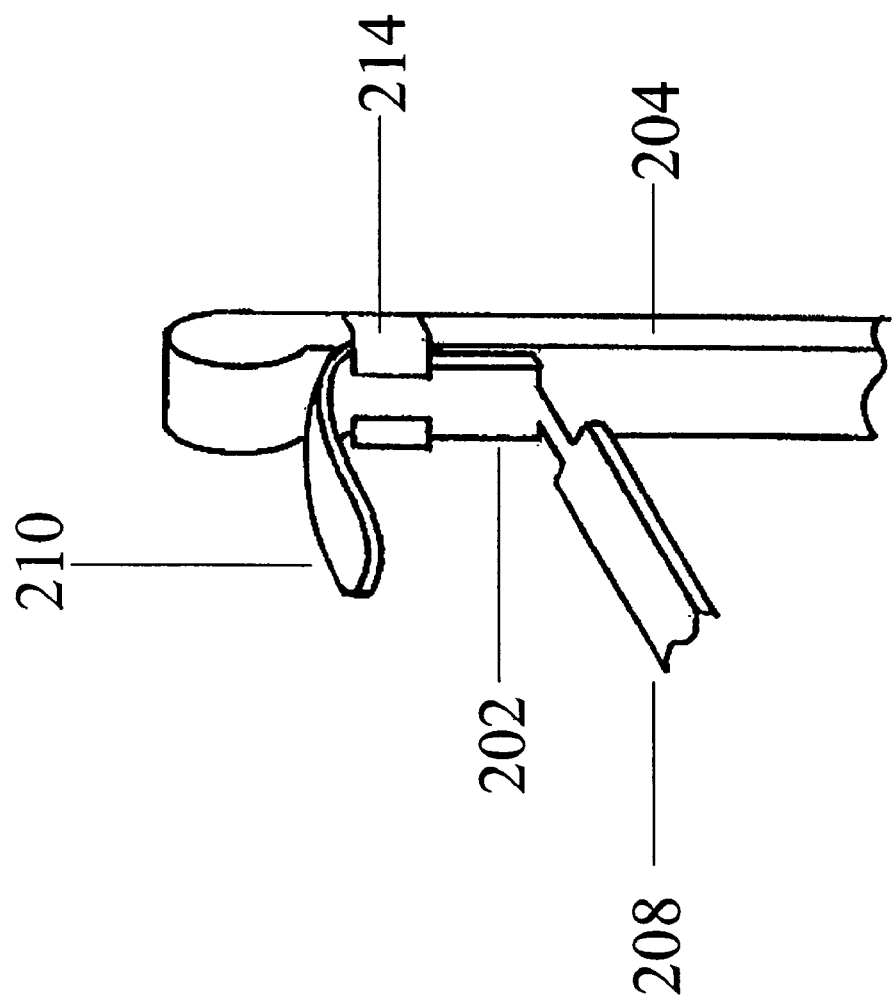
Figure 8C:
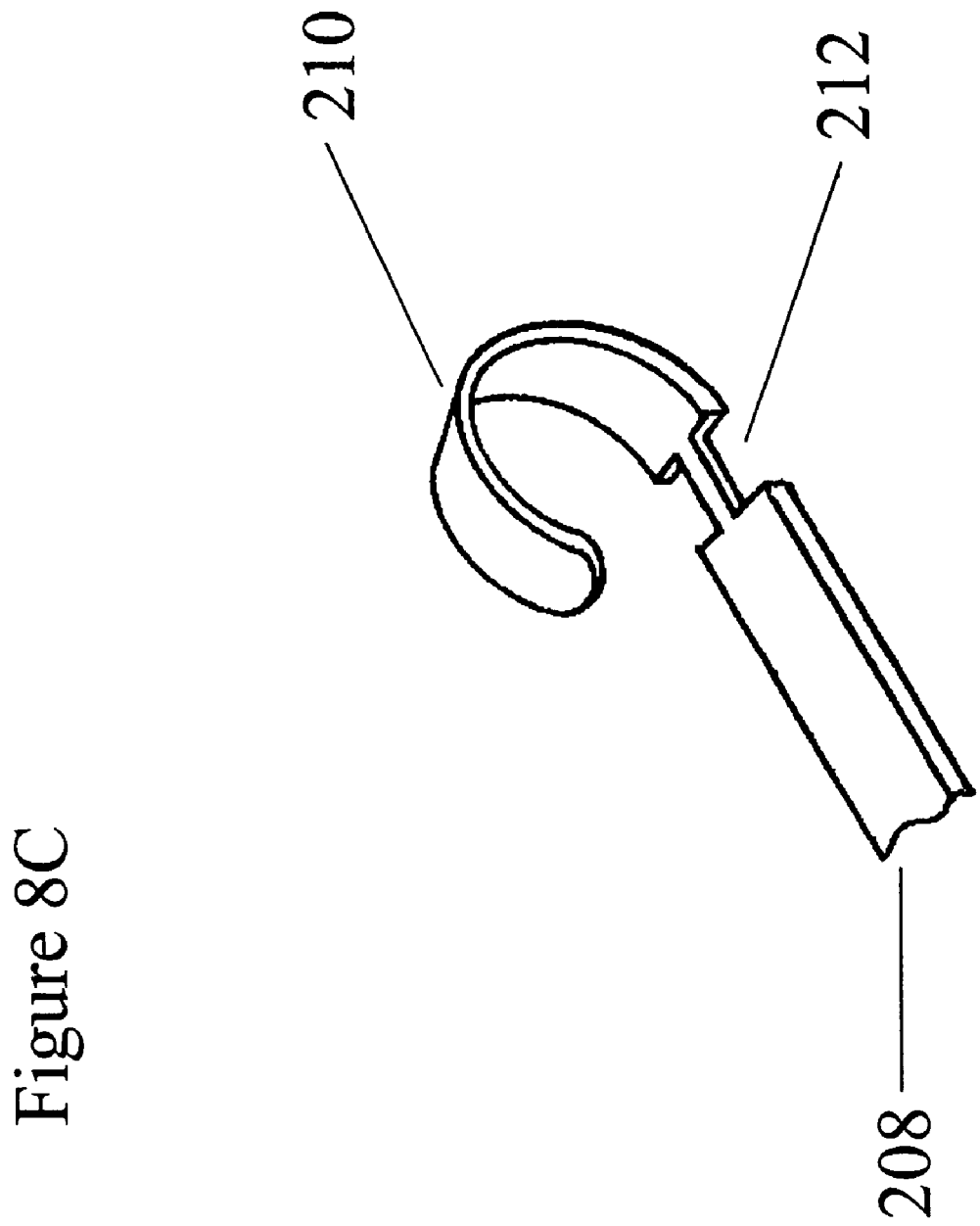

FIGS. 8A–C show an anchor system 200 for insertion into tissues to affix one tissue to another. As used herein, the term anchor refers to a structure wherein outwardly arranged arms are available to engage a target tissue. FIG. 8A shows an anchor member 202 held in a carrier 204 which is configured to hold the anchor member 202 substantially straight. In the depicted embodiment, the anchor member 202 may be originally formed to curve back upon itself, but may be straightened out by the carrier 204. The anchor member 202 may be formed in whole or in part of an elastic material to permit this to occur. As shown in FIG. 8A, the distal point 206 of the carrier 204 may be sharpened to permit insertion from a first tissue into a second. Once the distal point 206 of the carrier has reached the desired depth in the second anchoring tissue, the carrier 204 may be pulled proximally on the anchor member 202, allowing the anchor member 202 to assume its original curved shape 210, as shown in FIGS. 8B and 8C. The carrier 204 may be removed entirely from the anchor member 202 when its tabbed arms 214 reach the removal notch 212 on the anchor member 202. Alternatively, the carrier 204 may be left attached to the anchor member 202 so that by directing the carrier 204 distally on the anchor member 202, the anchor member 202 may be straightened out within the tissues and the anchor system 200 can be removed from the tissues. The proximal end 208 of the anchor system may be fitted with any sort of head or other securing device that will affix or embed the proximal end of the anchor member 202 within the first tissue layer.

Figure 9A:
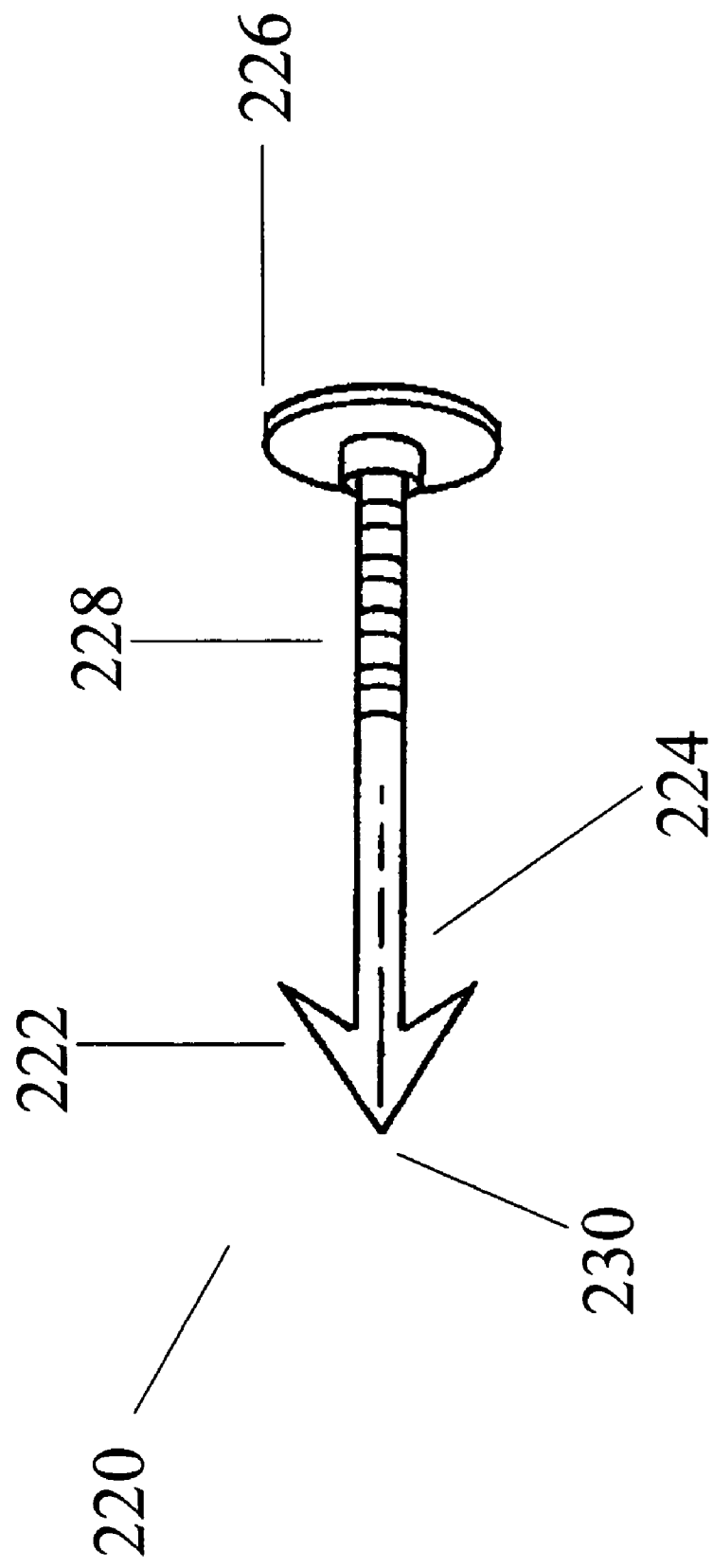
FIGS. 9A–C depict embodiments of fixation devices according to the present invention.
Figure 9B:
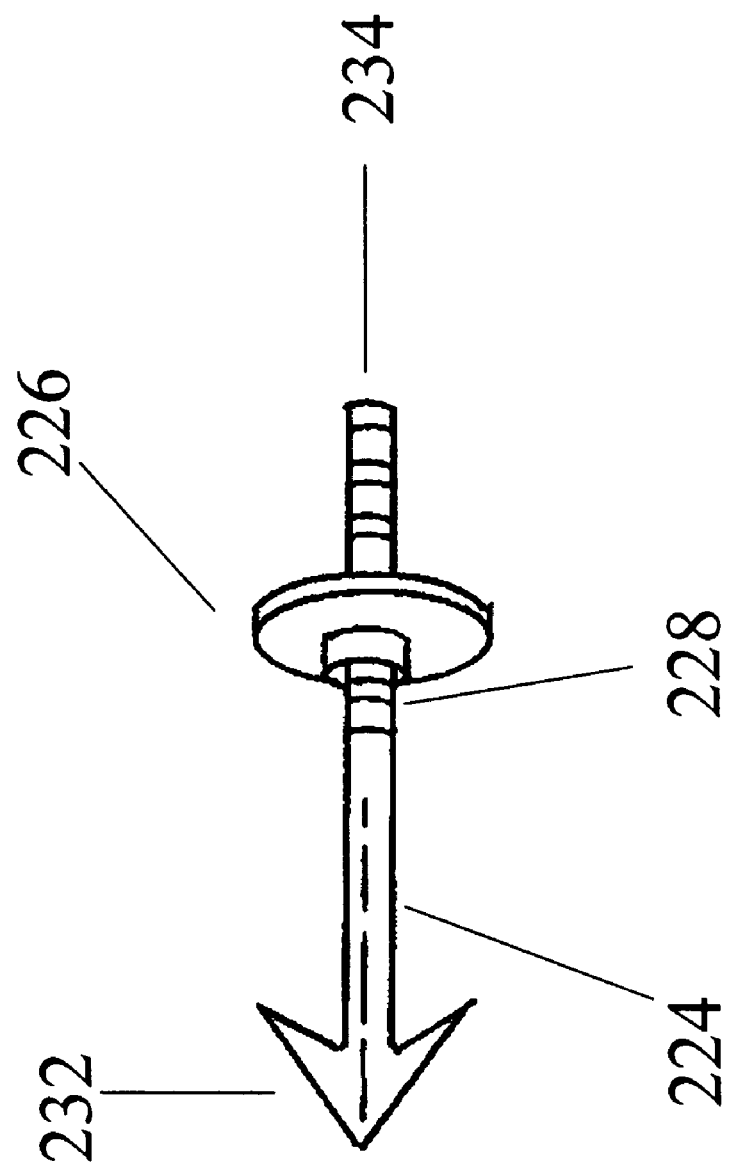
Figure 9C:
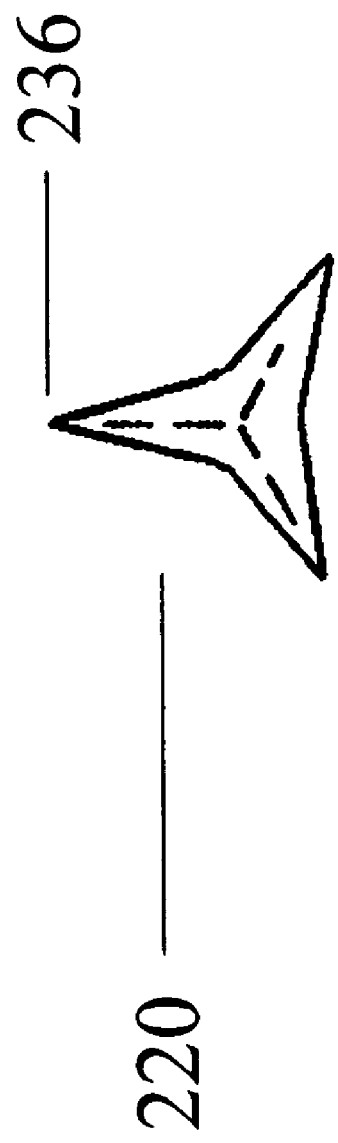

FIG. 9A shows an embodiment of an anchor 220 with a distal insertion point 230 adapted to penetrate a first tissue to arrive in a second tissue. A set of arms 222 are shown folded or collapsed axially around a central shaft 224. When the anchor 220 is inserted into the preselected anchoring tissue, the collapsed arms 222 can be directed outward into an anchoring position 232, as shown in FIG. 9B. The adjustable base 226 may then be positioned on the shaft 224 to provide the appropriate compressive force pushing the first tissue towards the second. Once the adjustable base 226 has been compressed sufficiently, it will lock into one of the circumferential grooves 228 circumscribing the shaft 224. Optionally, a protruding part 234 of the shaft 224 may be trimmed or cut flush with the base 226. As shown in FIG. 9C, a view of the top of an anchor 220, a plurality of arms 236 may be arranged according to various designs to grasp particular tissues with optimal tenacity. The structures depicted in these figures may be made of non-absorbable materials or of materials wholly or partially absorbable. In particular, where pointed areas are shown in these and other figures, it may be desirable to form the points from absorbable materials so that they do not present to the patient a long-term sharp edge.

Figure 10A:
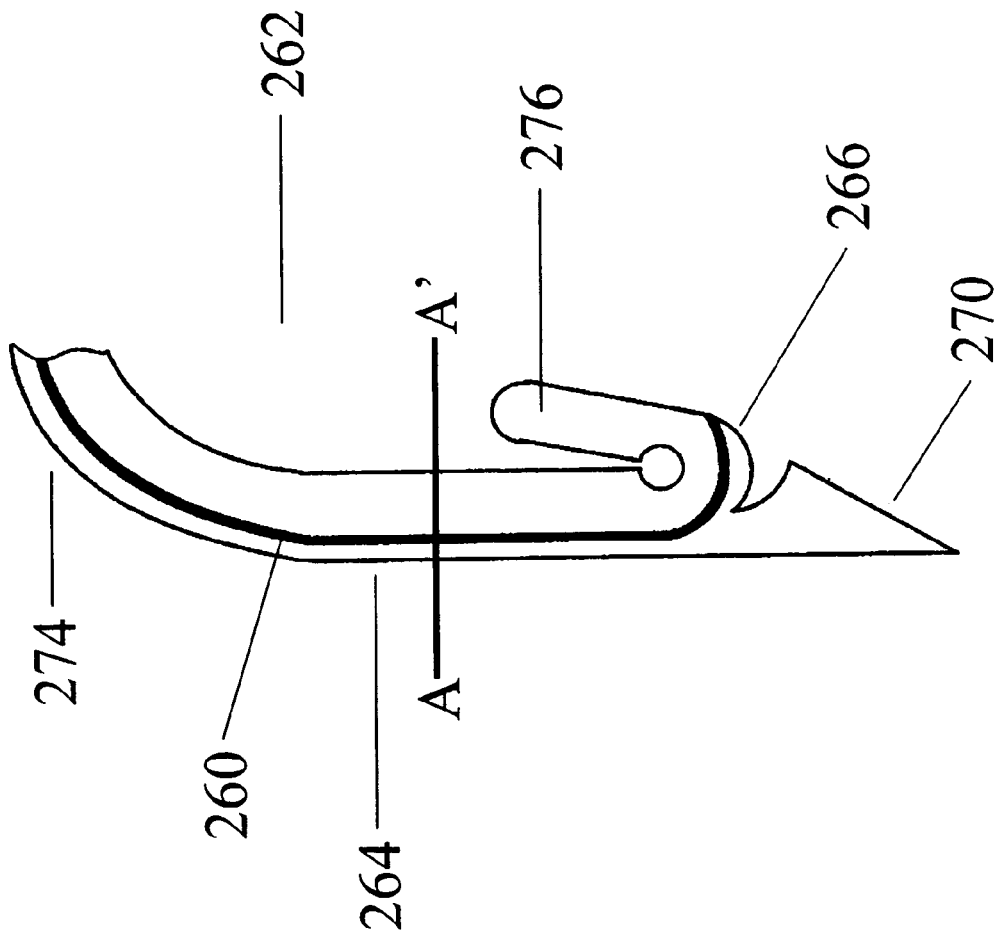
FIGS. 10A–C depict embodiments of fixation devices according to the present invention.
Figure 10B:
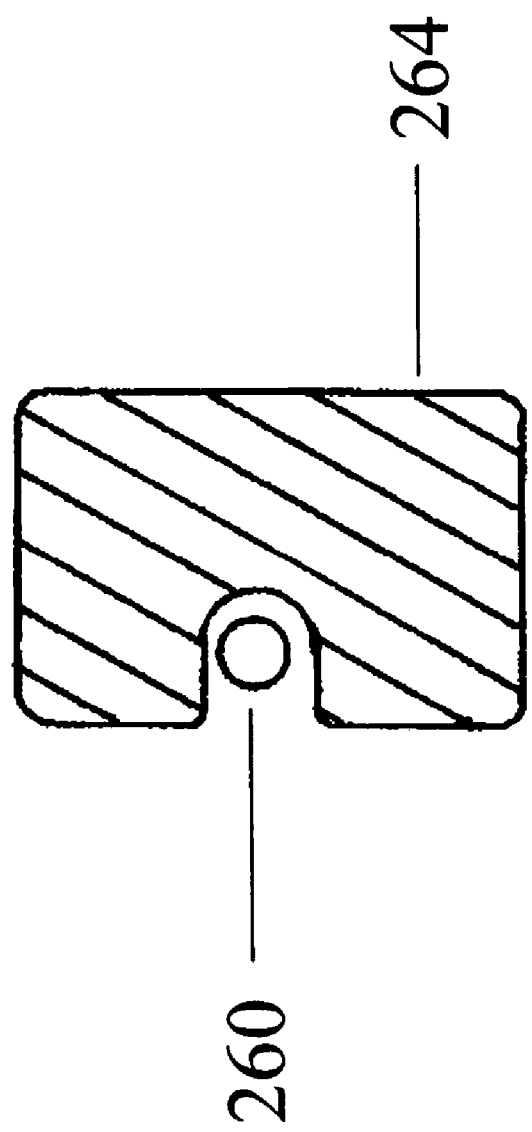
Figure 10C:
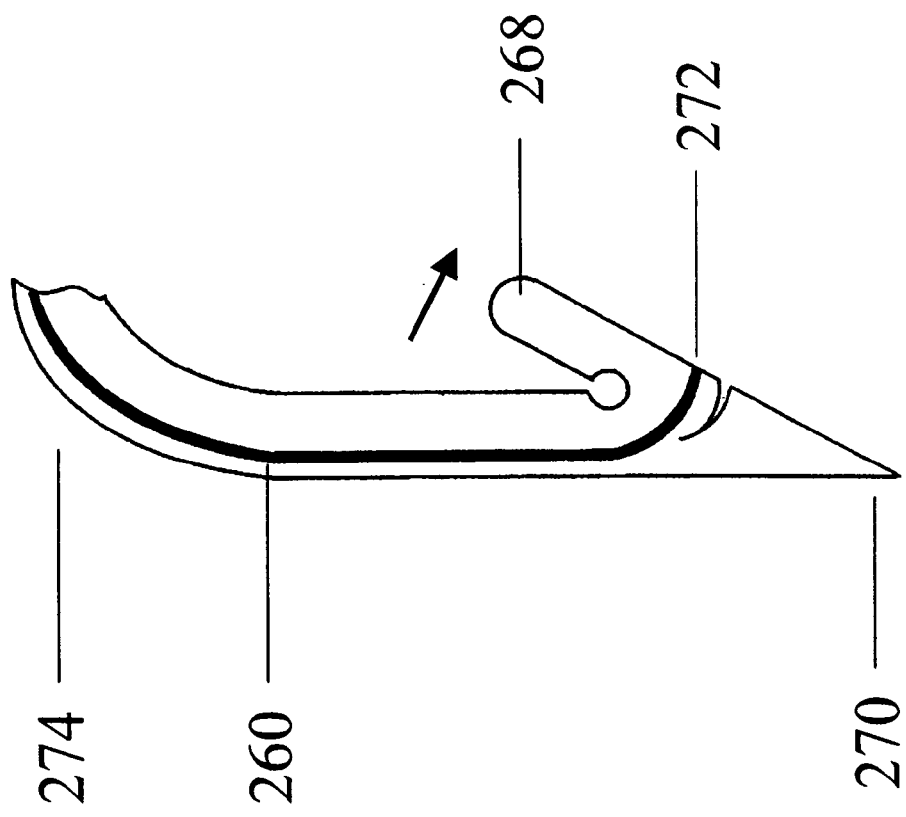

FIGS. 10A–C depict embodiments of tissue anchors that are directed to open from an initially closed position by the use of muscle wire. As used herein, the term muscle wire relates to a type of memory wire or SMA, commonly a titanium nickel alloy, that returns to a preset shape at a preset transition temperature. At the preset temperature the wire contracts in length a determined amount. In certain forms, the amount of muscle wire contraction at the transition temperature is about 3–5%. The force exerted by this contraction can be very powerful. The muscle wire has a "programmed" temperature at which it has a "programmed" shape. When the wire cools, it goes back to a non-programmed shape. As the wire is heated, it tries to return to its programmed shape. Hence, the wire has two possible states. There is the cooled state (temperature) at which the wire can be stretched, and the programmed state (temperature) at which the wire returns to its programmed length. At the programmed state, the wire exhibits a crystalline structure known as austenite. As the wire cools, the structure changes to martensite, which is a herringbone shaped crystal lattice. The martensite is much more flexible than the austenite, allowing the cooled wire to expand. When the wire is heated to its transformation temperature, the structure reverts to austenite and the wire contracts. When in the austenite state, the wire is much more susceptible to stress, and thus is more easily damaged.

As depicted in FIG. 10A, a muscle wire 260 is embedded in an anchor 262, running through the shaft 264 across a flexible joint 266 to attach to the proximal portion 272 of the anchoring arm 276. An insertion point 270 is provided whereby the anchor 260 in its collapsed state can be inserted into the target tissue. The proximal part 274 of the anchor 260 may be fitted with any fastening structure allowing it to engage and become implanted in the first tissue through which the anchor passes, while the anchoring arm 276 is adapted for lodging within the second, anchoring tissue. FIG. 10B shows a cross-section of the shaft 264 taken at a line A–A' on FIG. 10A. In FIG. 10B, a muscle wire 260 may be seen partially embedded in the shaft 264. Other arrangements will be evident to practitioners in the art whereby the muscle wire 260 can be carried in the anchor shaft. FIG. 10C shows the effect of contraction of the muscle wire 260: the muscle wire 260 has shortened and exerted tension on the proximal end 272 of the anchoring arm 276. This tension has forced the anchoring arm 276 outward from its initial contracted position, so that its distal end 268 engages the surrounding tissues. The muscle wire 260 may also exert tension on the proximal end 274 of the anchor 260, where a fastening structure has been placed. This tension on the proximal end 274 and its affixed fastener may serve further to compress the two tissues whose coaptation is desired. As has been previously described, the insertion point 270 may be made from an absorbable material so that the point does not remain in the tissues, potentially damaging them. The distal end 268 of the anchoring arm 276 is shown here to be rounded, although other shapes can be envisioned by skilled artisans in the field.

Figure 11A:
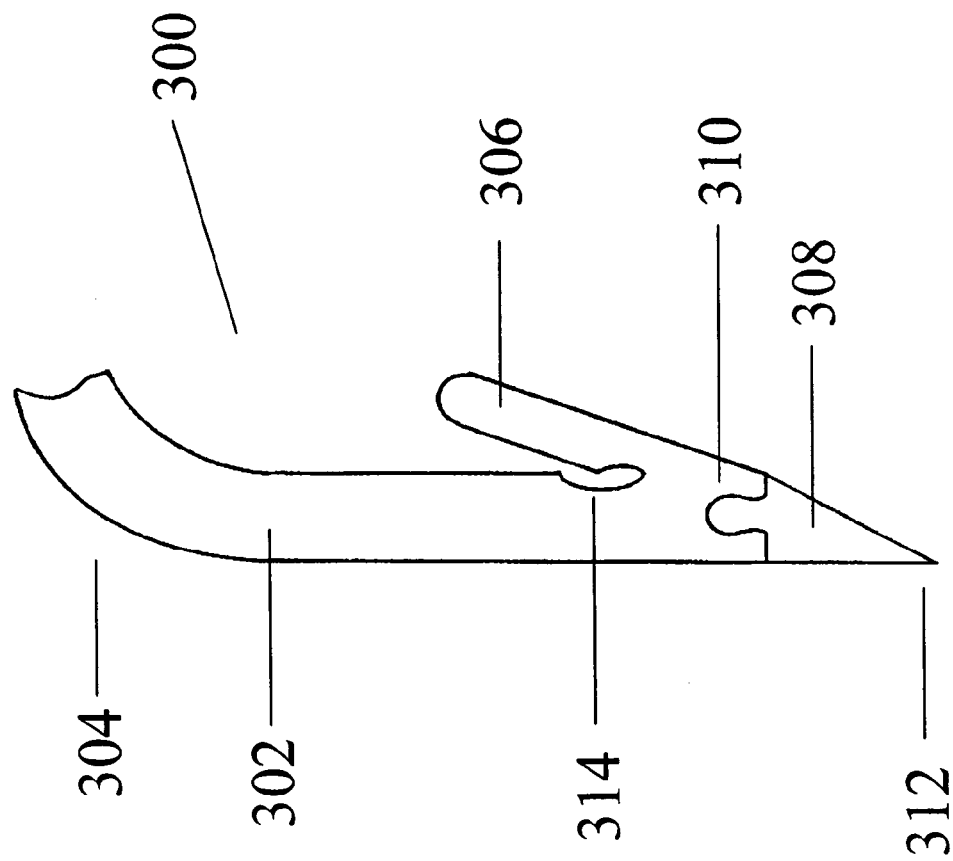
FIGS. 11A and B depict embodiments of fixation devices according to the present invention.
Figure 11B:
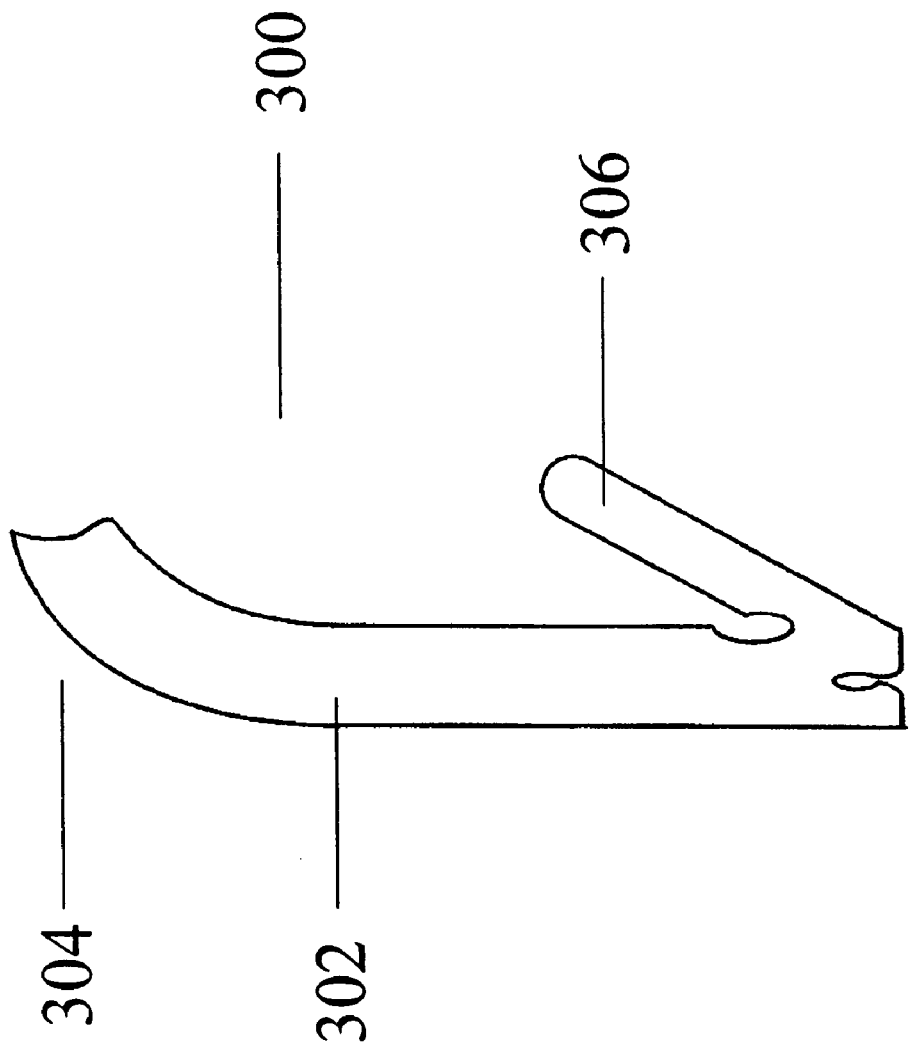

The embodiment depicted in FIGS. 11A and B takes advantage of the fact that certain polymers, well-known in the art, are biocompatible and water-soluble. In the depicted embodiment, an anchor system 300 is shown with a proximal end 304, a shaft 302 and a spring-loaded anchoring arm 306. FIG. 11A shows the anchoring arm 306 bent against the shaft 302 in a closed position. The anchoring arm 306 is held in this closed position by a water-soluble polymeric lock 308 inserted in a tongue-in-groove configuration 310 in the outer aspect of a joint 314 between the shaft 302 and the anchoring arm 306. The spring-loaded anchoring arm 306 is thus held in the closed position by the presence of the polymeric lock 308. While a tongue-in-groove lock shape 310 is shown in the depicted embodiment, it is understood that any lock mechanism that uses the water-soluble polymer to block the outward motion of the spring-loaded anchoring arm 306 may be suitable for use in this system. The polymeric lock 308 is also equipped with an insertion point 312 that may provide a leading edge for the anchoring system 300 to penetrate the tissues. As shown in FIG. 11B, when the water-soluble polymeric lock dissolves, the force resisting the outward spring of the spring-loaded anchoring arm 306 is removed and the anchoring arm 306 springs outward. In the position depicted in FIG. 11B, the anchoring arm 306 may engage the tissues, thereby seating the anchoring system 300. The proximal end 304 of the anchoring system 300 may be fitted with any appropriate fastener to seat or embed it in the most proximal tissues.

Figure 12A:
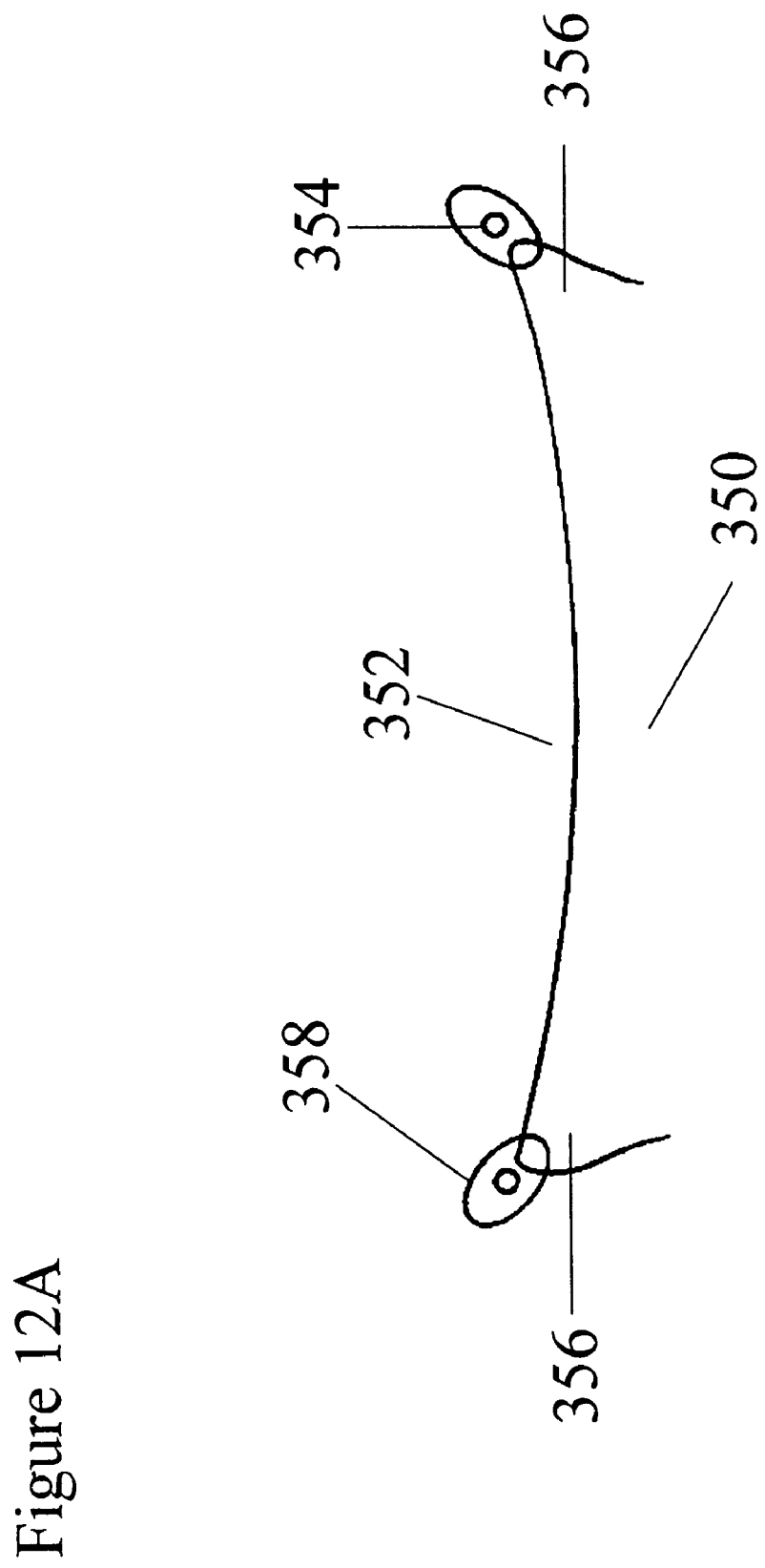
FIGS. 12A and B show schematically the anatomical basis for a paravaginal repair of a pelvic floor defect.
Figure 12B:
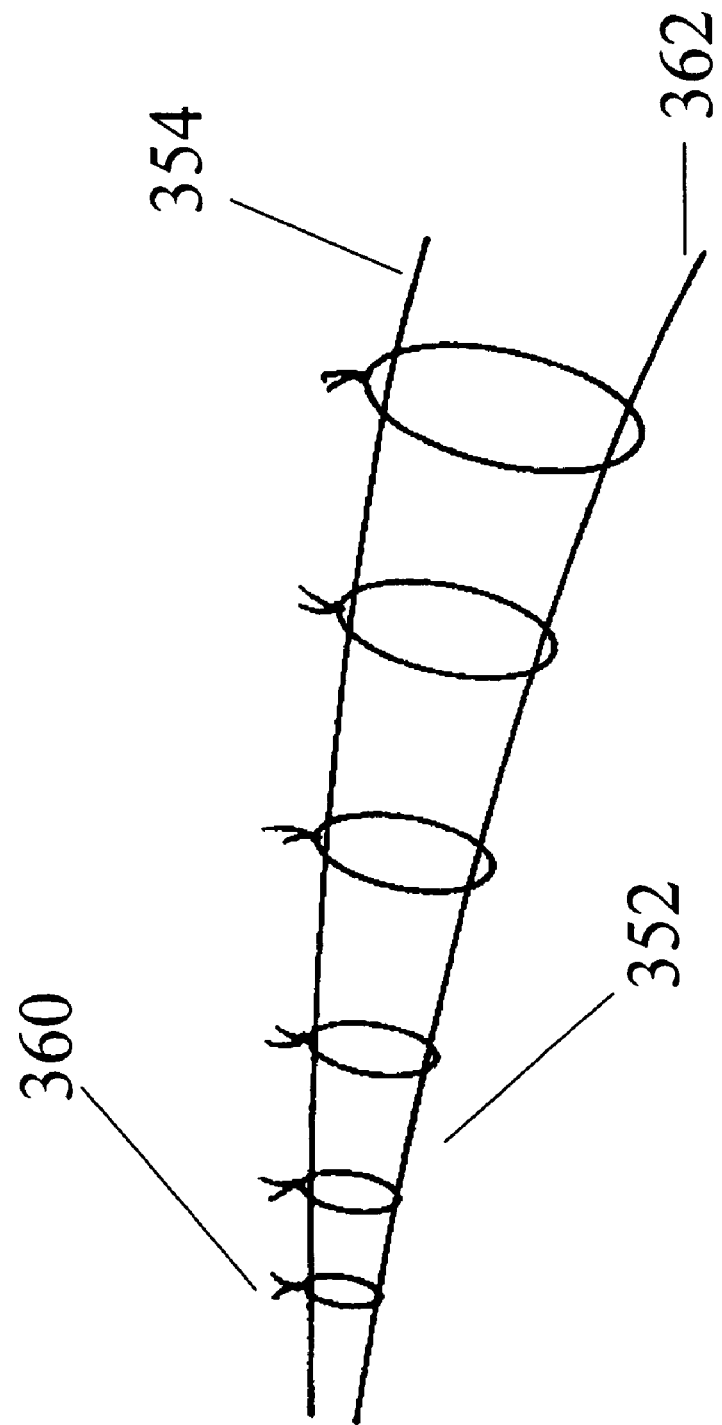

FIGS. 12–14 show an embodiment of an anchoring system, here illustrated with particular reference to soft tissue reconstruction of the female pelvic floor. While the use of this embodiment will be illustrated with reference to this anatomic location, it is understood that other anatomic applications will be readily apparent to those of ordinary skill in the art. FIGS. 12A and B show schematically how soft tissue reconstruction may be employed to treat laxity of the female pelvic floor. FIG. 12A shows a laxity of the anterior wall 352 of the vaginal vault 350 being repaired by a fixation of the lateral sulci 356 of the vagina to the ATFP 354. Any fixation device may be used to accomplish this, including sutures, as are well-known in the art. FIG. 12B shows a lateral view of the repair, where the anterior wall 352 of the vagina is being affixed to the ATFP 354 using sutures 360 placed under varying degrees of tension so that the tissues are approximated properly to suspend the anterior vaginal plane 362. FIGS. 13 and 14 show an embodiment of a fixation system adapted for soft tissue reconstruction. The fixation system depicted herein is characterized by adjustable tension and by precision placement, making it suitable for use in vaginal surgery and in other forms of soft tissue reconstruction. The schematic depictions of these figures indicate a feature of the systems and methods of the present operation, wherein a surgical incision is not created to expose the anchoring tissues. As used herein, the term "expose" relates to a surgical process well-understood by practitioners whereby a particular tissue is approached by an incision of adequate size to permit the tissue to be identified and dissected free, substantially under direct vision. Incisions used for exposure understood to be significantly larger than an incision intended to provide laparoscopic or palpation access to the same structure. In one practice of the systems and methods using laparoscopic guidance, for example, for a cystocele repair, a laparoscope may be used to visualize the defect and to visualize the intended anchoring structure for the repair. According to this method, a fixation device may still be inserted through the vagina into the lateral sulci to attain fixation in the ATFP. However, a laparoscope may also be inserted into the Space of Retzius using laparoscopic techniques well known in the art. By advancing the laparoscope, the defect requiring soft tissue reconstruction may be visualized, and the supporting structures may be identified. While this example relates to pelvic floor reconstruction, it is understood that laparoscopic or other forms of anatomic guidance may be employed within the scope of the present invention.

Figure 13A:
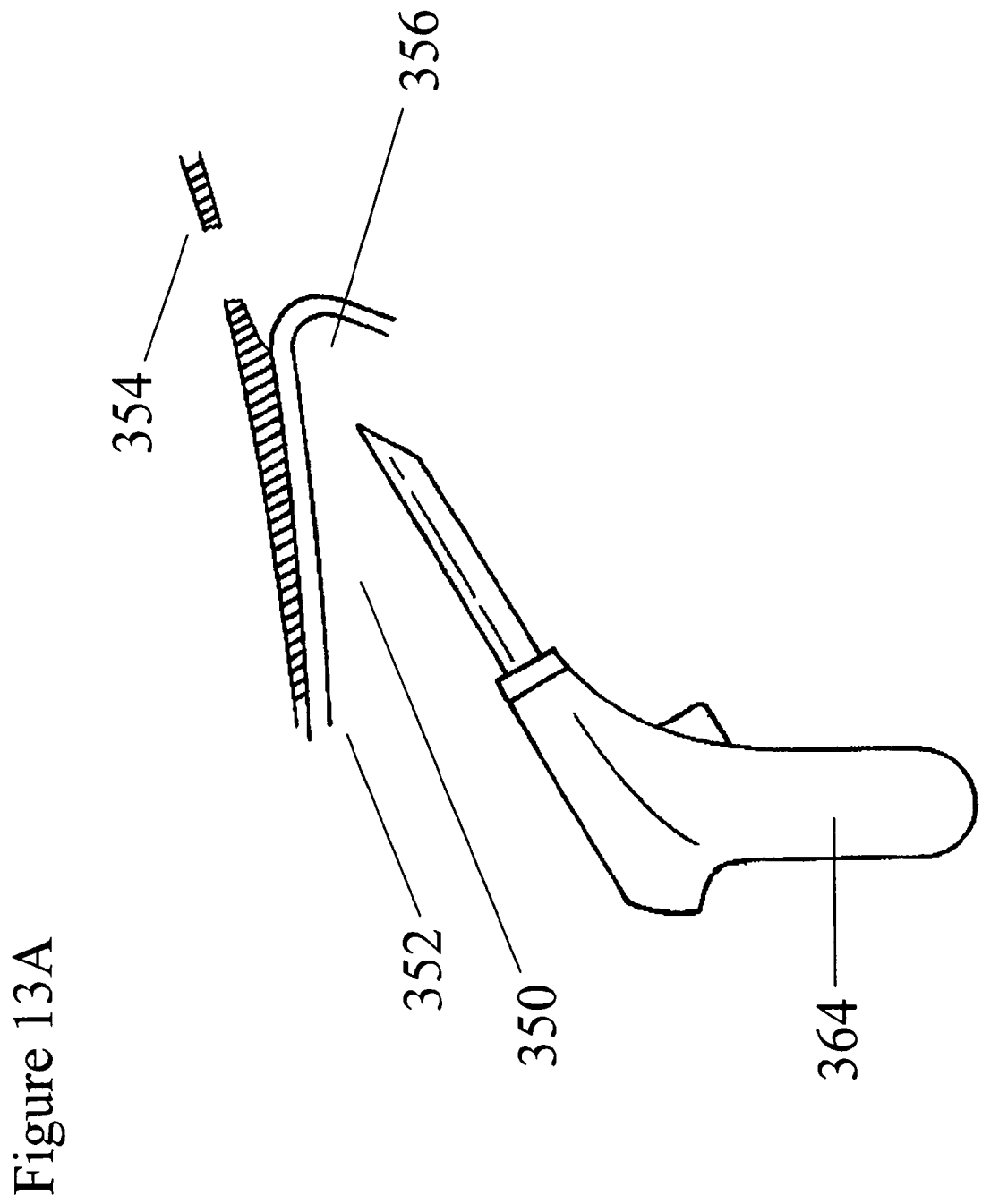
FIGS. 13A–G show schematically a repair of a soft tissue defect according to the systems and methods of the present invention.
Figure 13B:
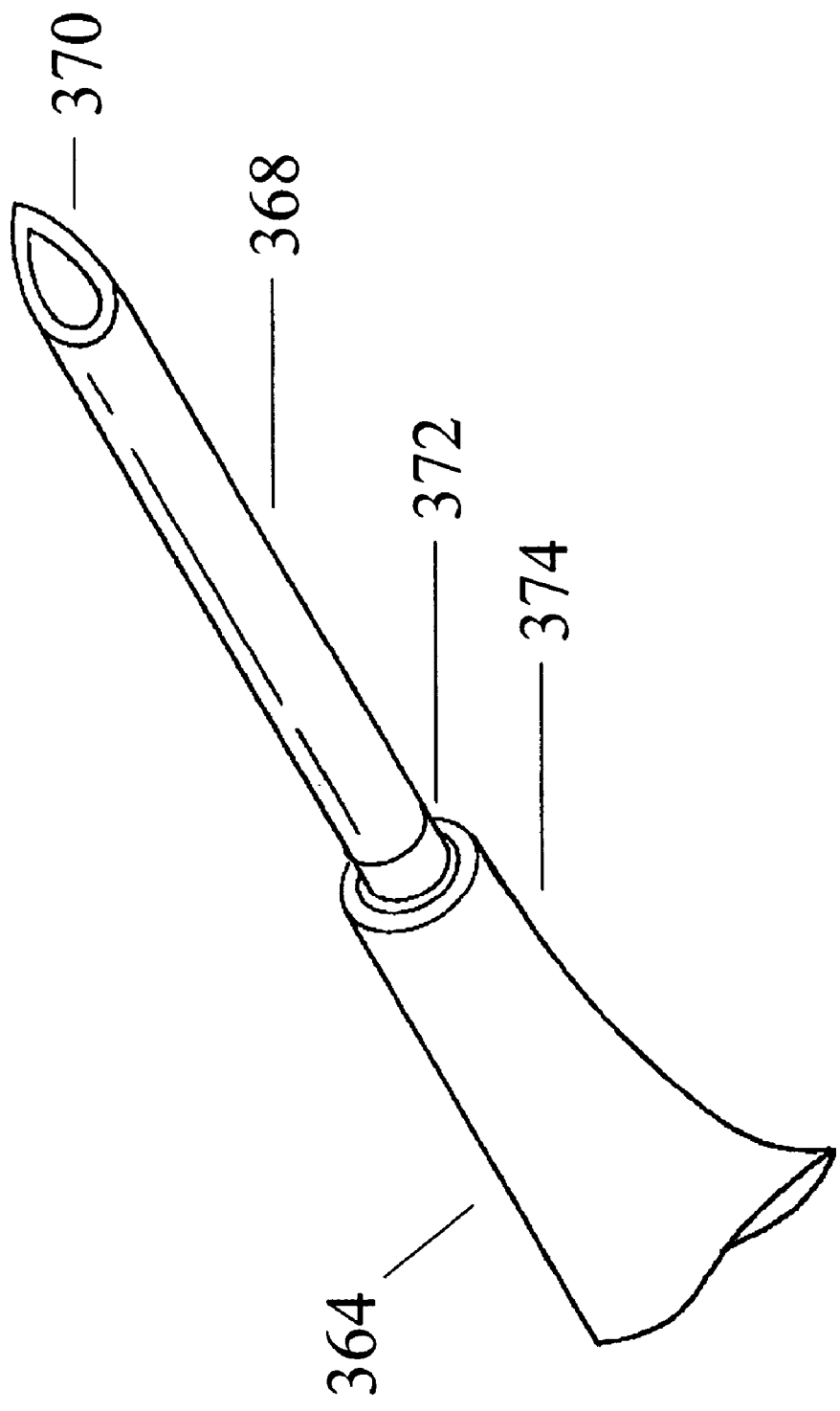
Figure 13C:
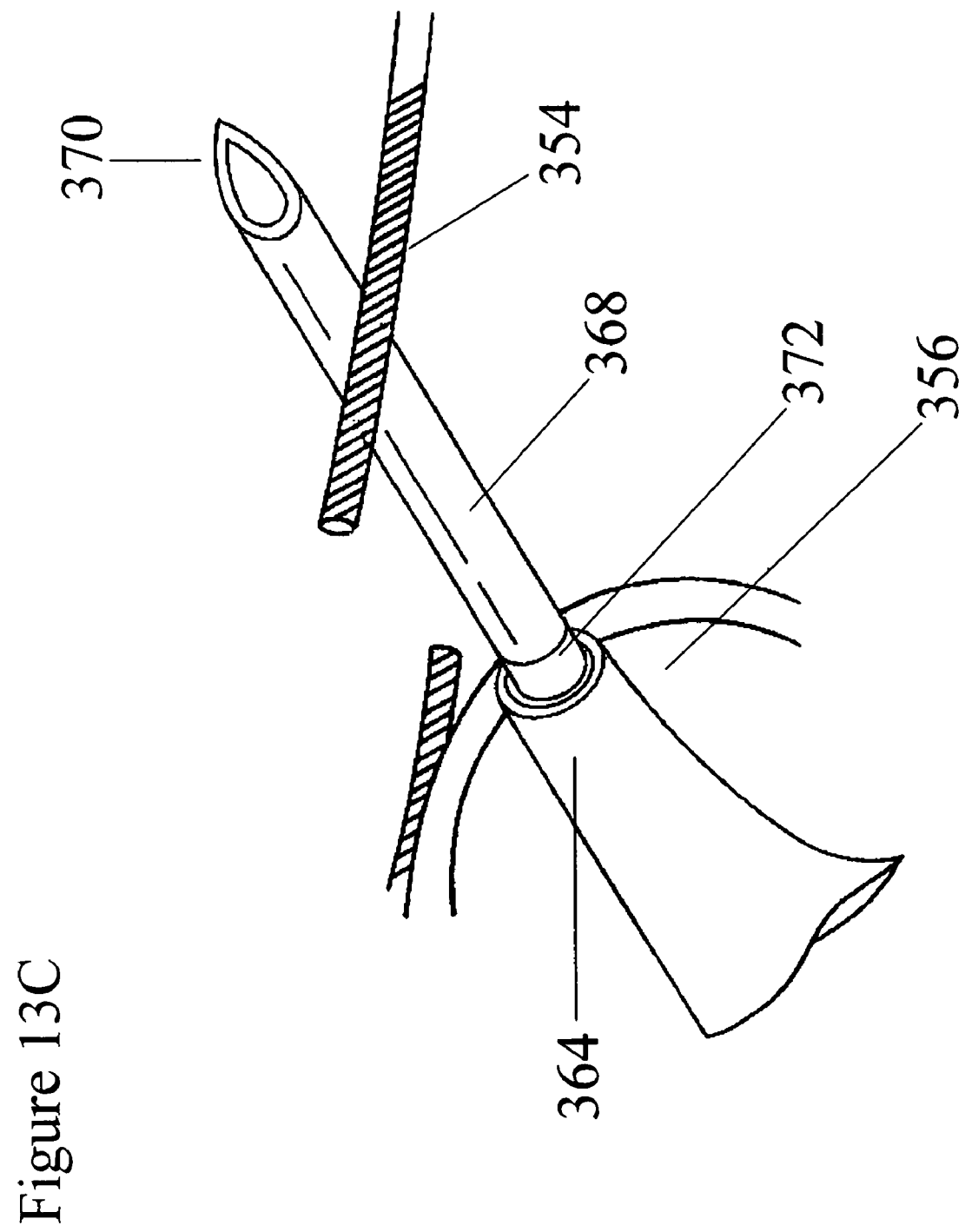
Figure 13D:
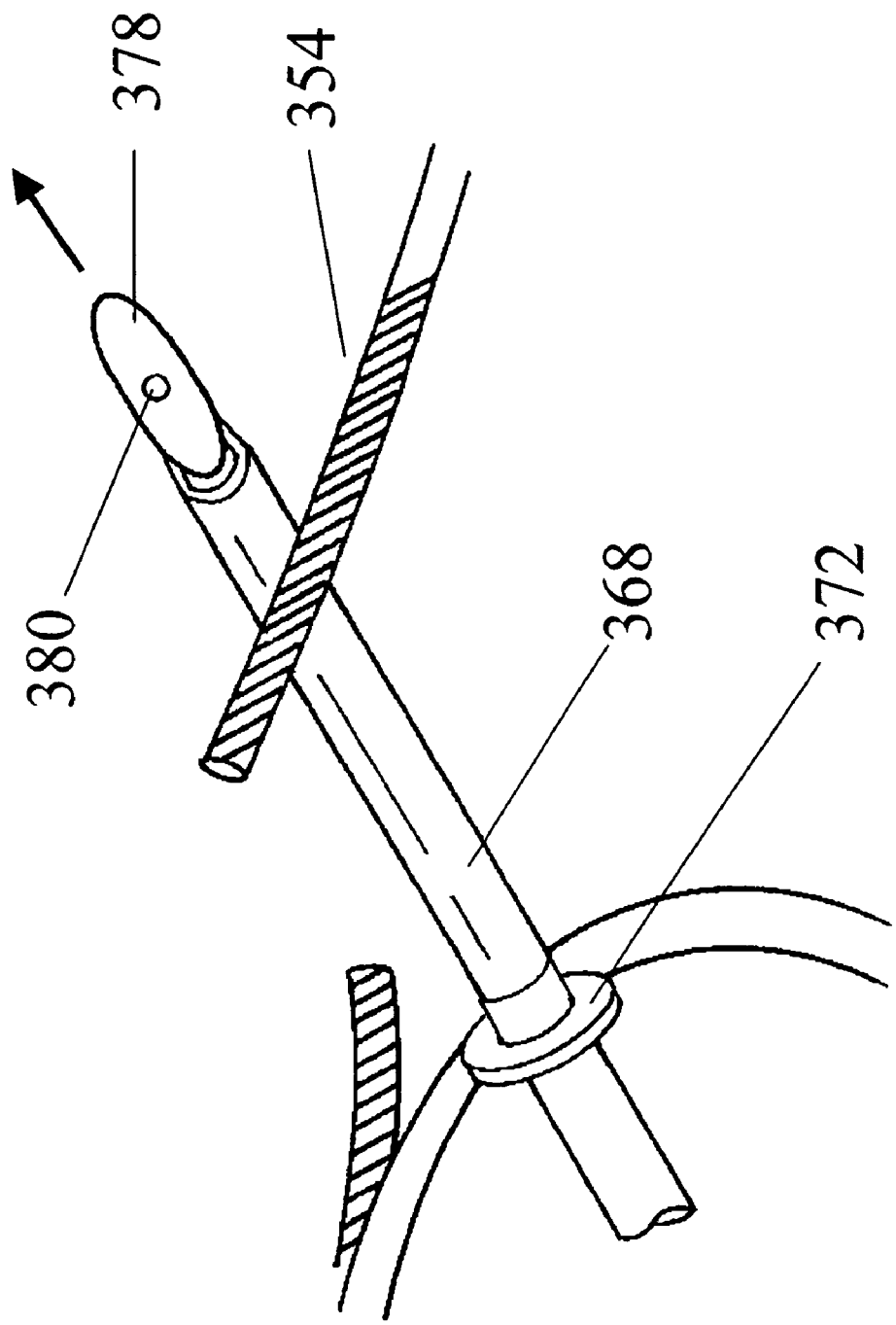
Figure 13E:
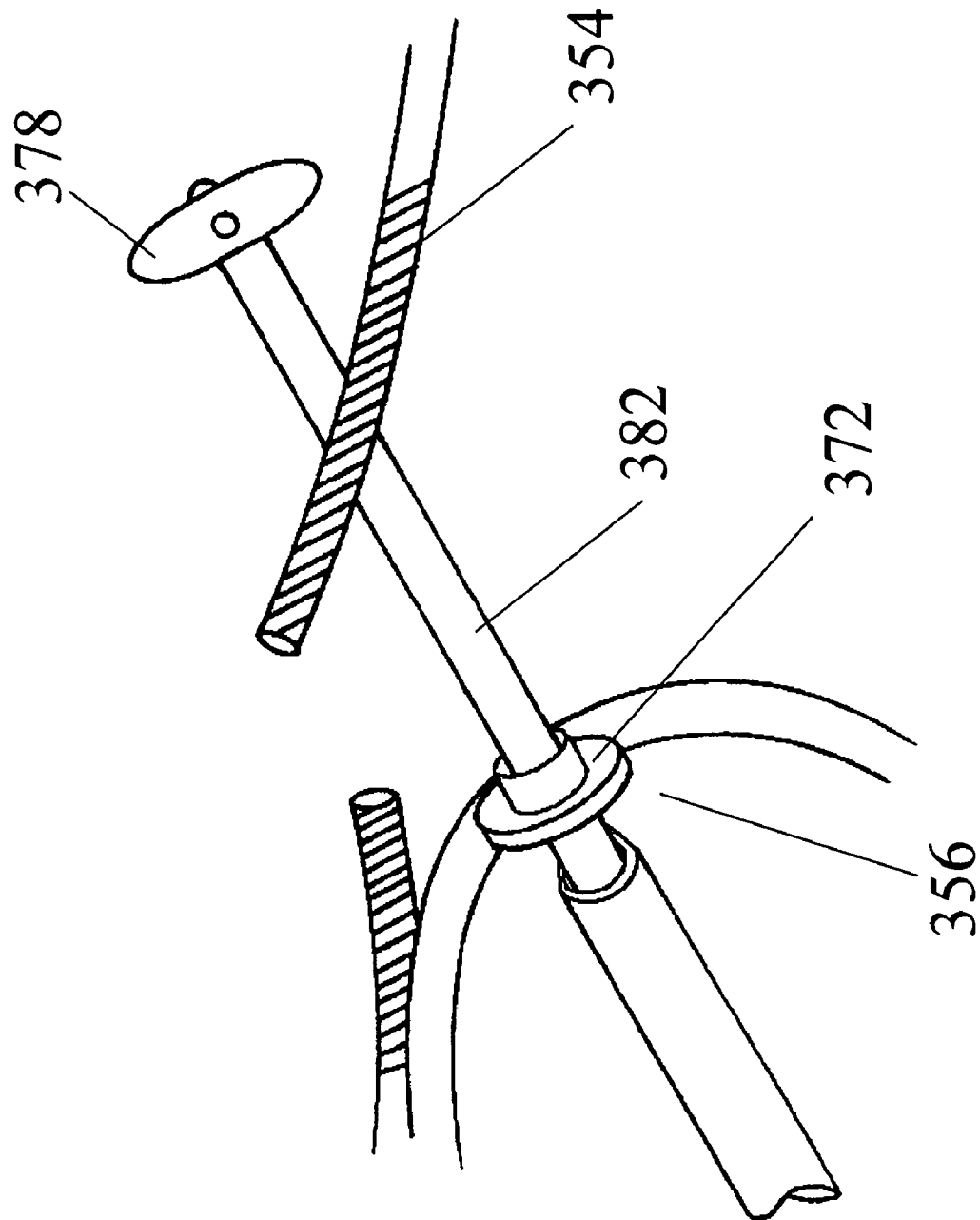
Figure 13F:
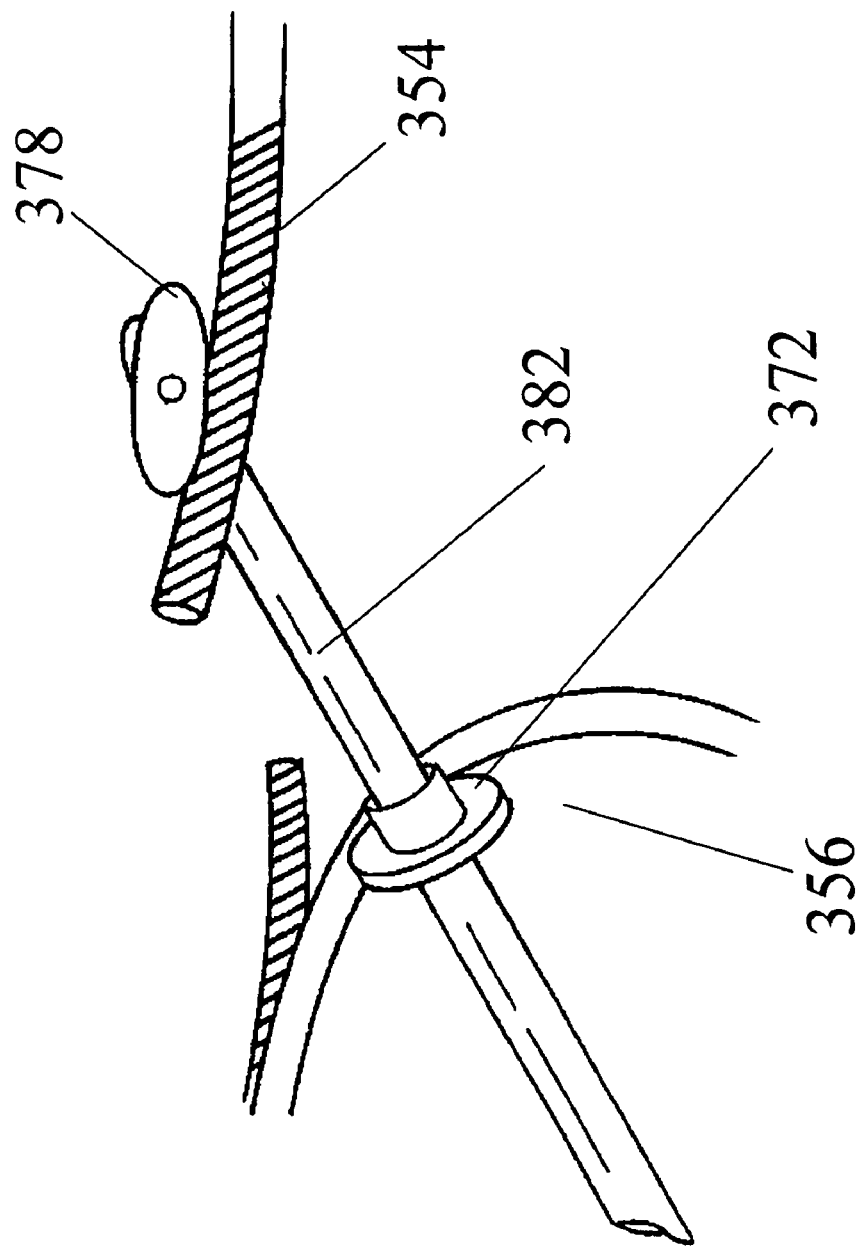
Figure 13G:
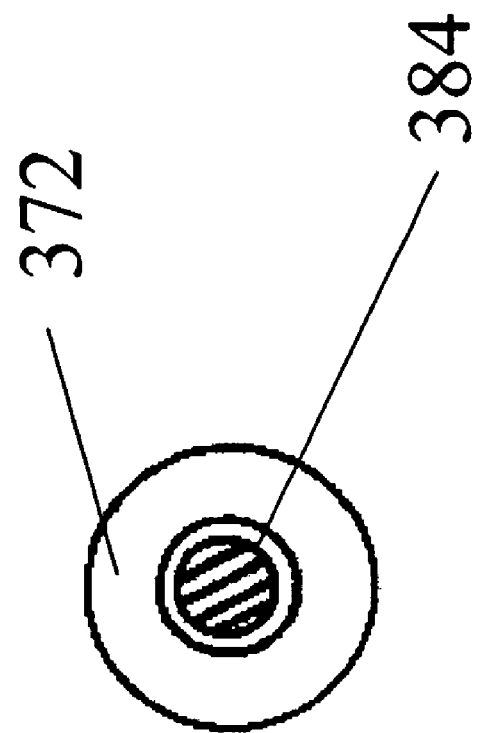

FIG. 13A shows an applicator 364 being inserted into the vaginal vault 350 to deliver a fixation device into the lateral sulcus 365 in order to affix this structure to the ATFP 354, thereby suspending the anterior wall 352 of the vagina. FIG. 13B shows in more detail the distal end 374 of the delivery device 364. In the depicted embodiment, a hollow needle 386 is situated on the distal end 374 of the delivery device 364, permitting delivery of fixation devices into the intended anatomic location. A penetrating tip 370 is located at the distalmost end of the needle so that tissues can be pierced to allow access thereto for the fixation devices. A microporous bolster 372 is shown in this figure at the proximal end of the needle. This bolster will provide proximal stabilization for the fixation device to be inserted. FIG. 13C shows the fixation device 364 directing the needle 368 through the wall of the lateral vaginal sulcus 356 and further through the ATFP 354. The penetrating tip 370 has been directed into the ATFP or just distal thereto, to permit placement of the fixation device so that it will be anchored in the ATFP. FIG. 13D shows a fixation device, here a toggle 378, being directed into the tissues comprising or adjacent to the ATFP. The toggle 378 passes through the hollow needle 368 to enter the tissues. The toggle is equipped with a swivel mechanism 380, shown in more detail in FIGS. 14D and E. When the needle is withdrawn, as shown in FIG. 13E, the toggle 378 swivels into a position normal to the longitudinal axis of the needle and remains in the ATFP 354. The microporous bolster 372 abuts against the wall of the lateral sulcus 356. A connector 382 is provided that is attached distally to the toggle 378 and that passes through or into the bolster proximally. The connector 382 may be a set of sutures or a polymeric connecting member or any other elongate structure that can be attached to the toggle 378 and further can be pulled proximally by the operator. As shown in FIG. 13F, the connector 382 may be pulled proximally through or into the bolster 356 after the needle is removed. The connector 382 exerts tension on the toggle 378 and advances the bolster 372 towards the ATFP 354. The connector 382 permits the operator to set the desired tension on the repair. When desired tension is achieved, the connector 382 is set. This may be accomplished by tying down the connector 382, as with sutures for example, or by attaching the connector 382 to the bolster 372 at an appropriate place so that constant tension is maintained. FIG. 13G shows the proximal end of the bolster 372, as seen from the vagina. The end 384 of the connector has been secured in the bolster 372 and has been cut so that it does not protrude into the vagina.

Figure 14A:
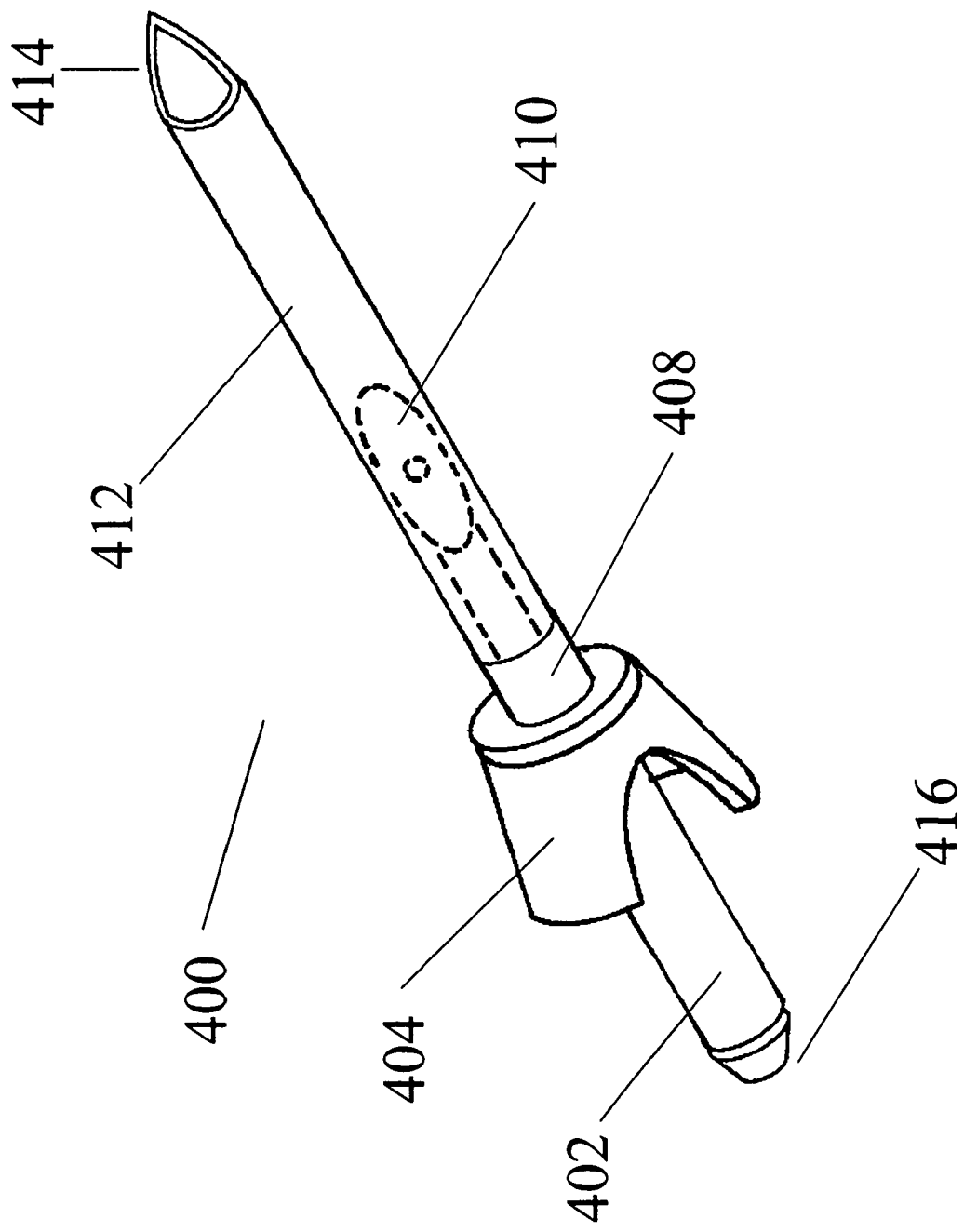
FIGS. 14A–G show in more detail embodiments of fixation systems and devices useful for the methods of the present invention.
Figure 14B:
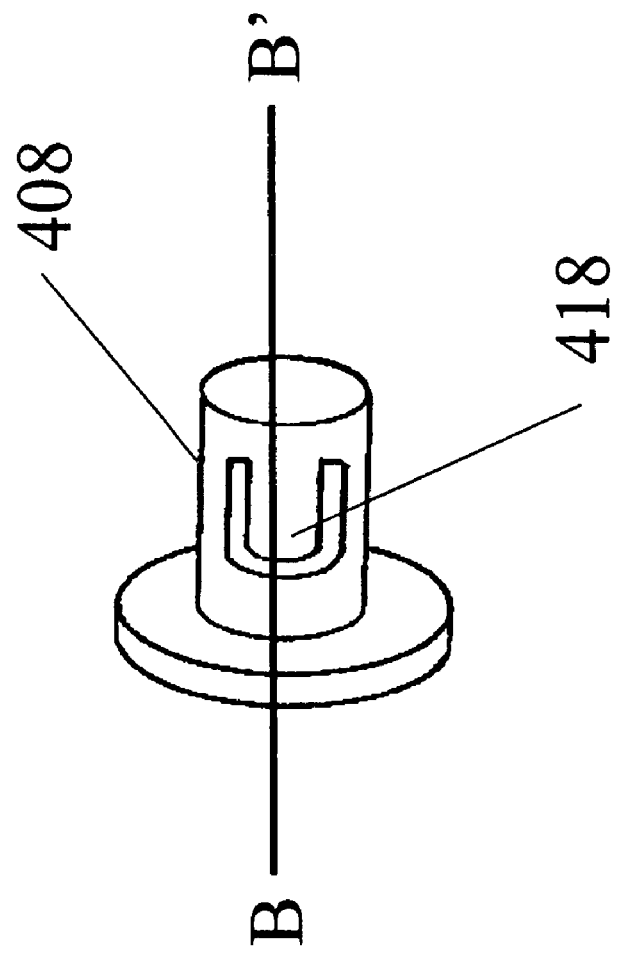
Figure 14C:
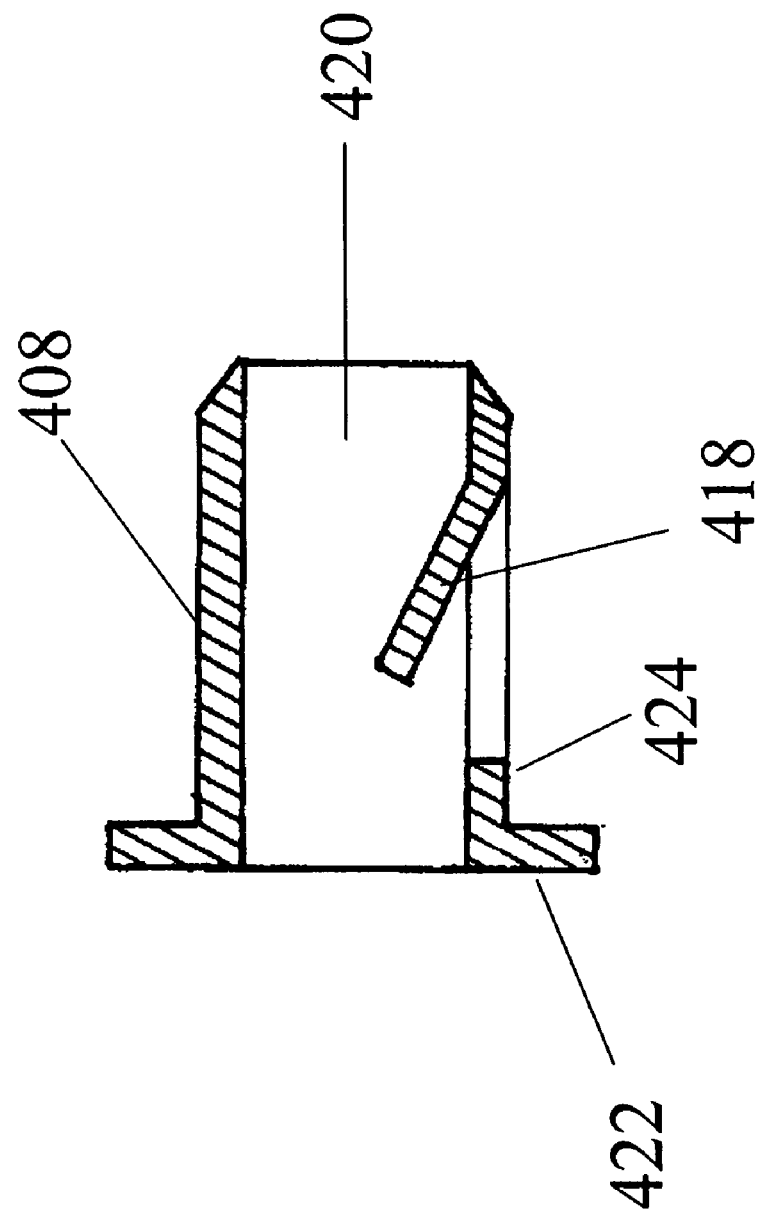
Figure 14D:
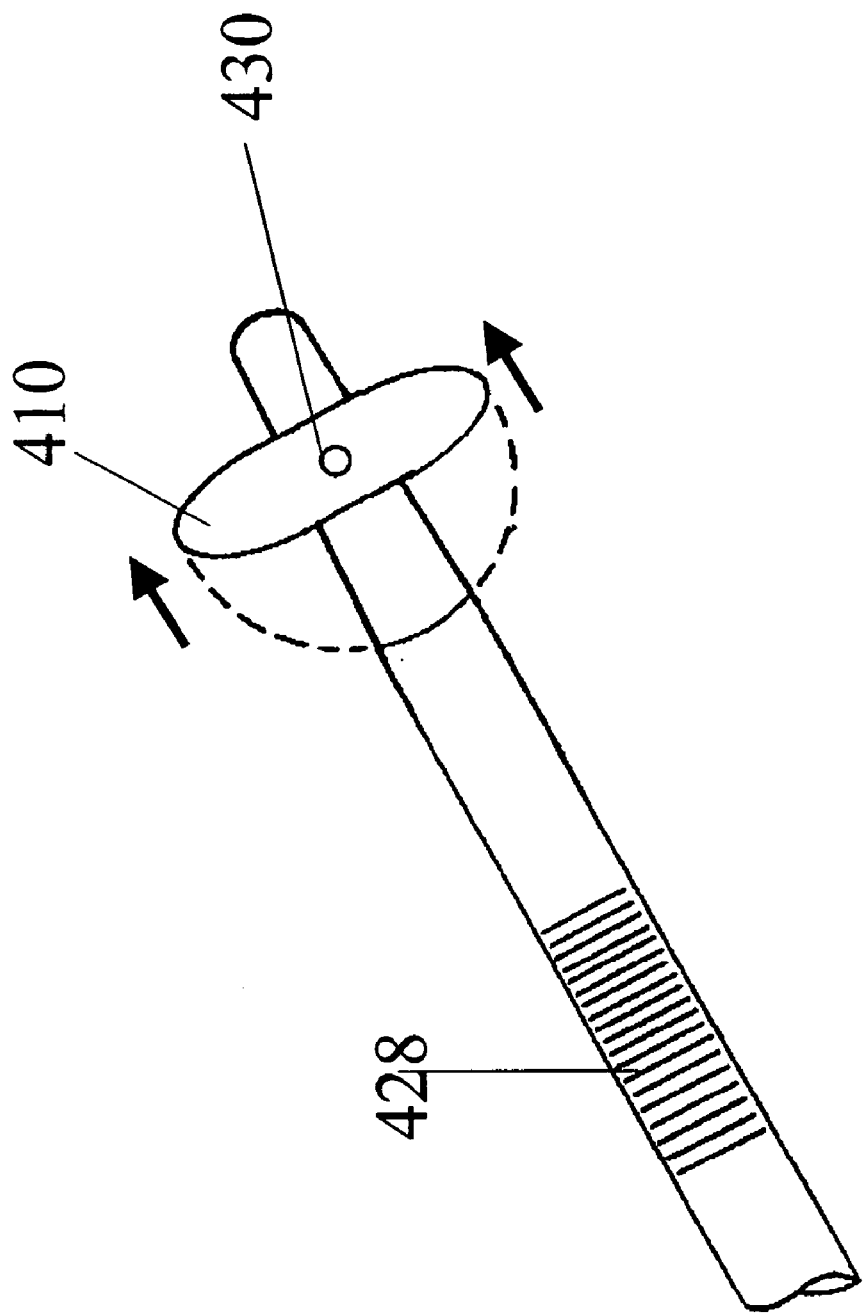
Figure 14E:
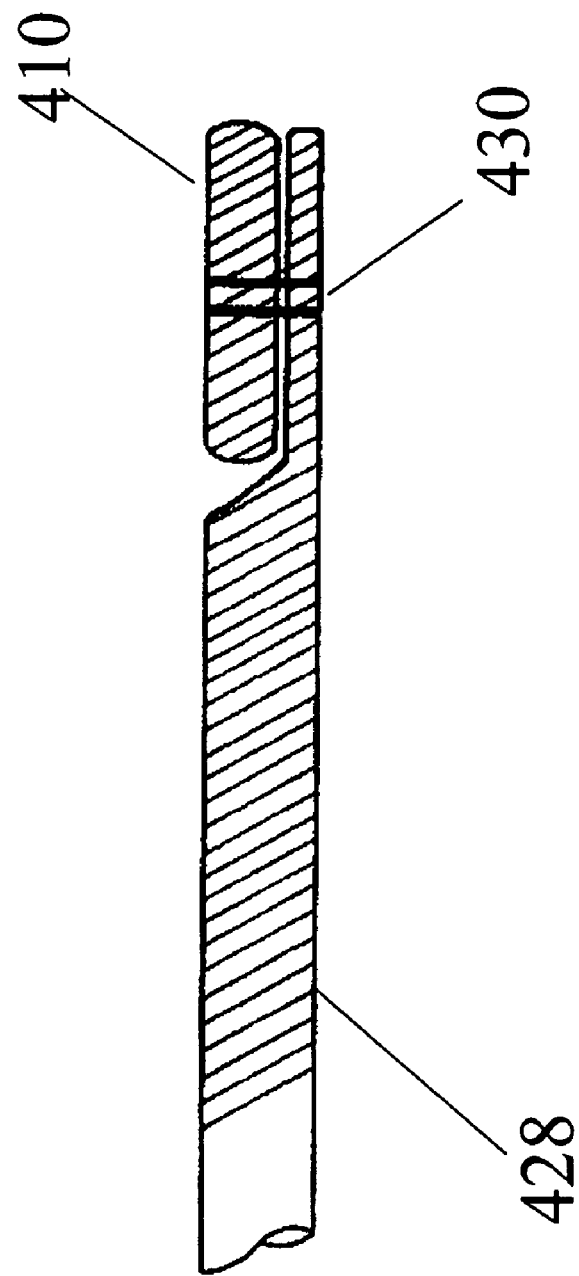
Figure 14F:
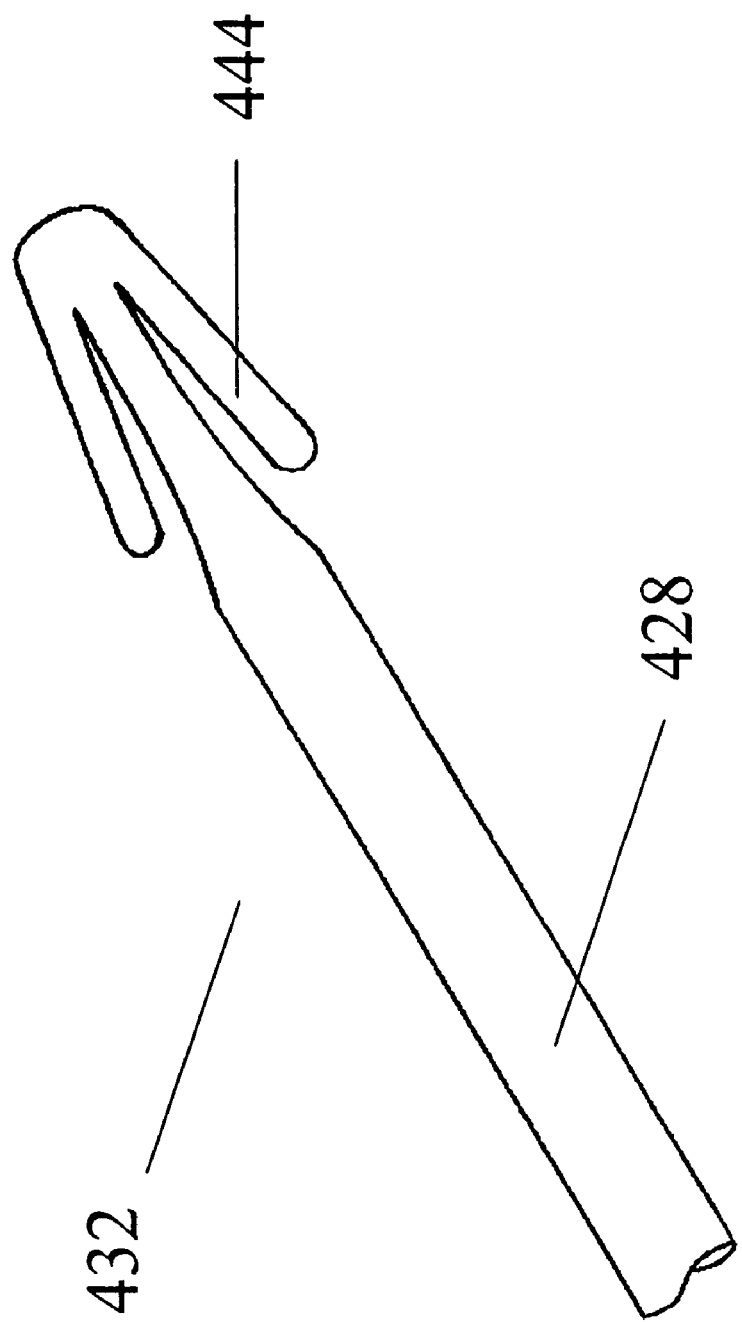
Figure 14G:
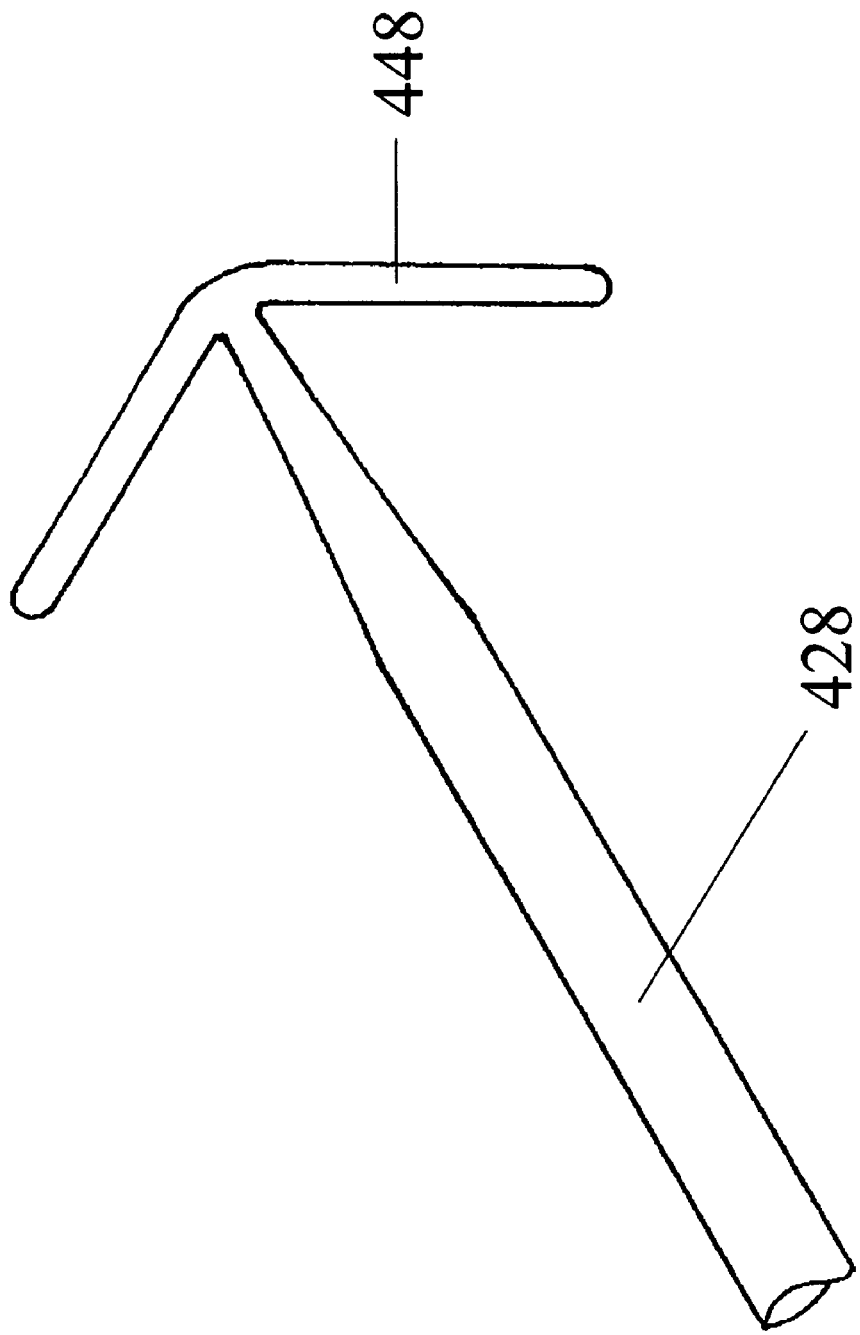

FIGS. 14A–G show in more detail features and modifications of the system illustrated in FIGS. 13A–G. FIG. 14A shows a disposable unit 400 adapted for use with a disposable or reusable applicator handle (not shown). In the depicted embodiment, an adapter cylinder 402 can be inserted within the applicator handle and can receive the plunger or other mechanism from the applicator that directs the toggle 410 outward through the needle shaft 412 to lodge in the tissues. A bolster 408 is shown along with a single toggle 410 in the depicted embodiment. The disposable unit 400 can equally be equipped with a multiple dispensing cartridge of toggles carried within it, accompanied by an associated stack of bolsters. As depicted in FIG. 14A, the proximal end 416 of the connector passes through the disposable unit 400 to permit the affixation of the toggle 410 to the bolster 408 after the toggle 410 has been properly positioned. FIG. 14B shows an embodiment of a bolster 408, wherein a flap lock 418 is provided so that the connector (not shown) can be secured after tension on the toggle is set. FIG. 14C shows a cross-section of the toggle 408 taken at line B–B' drawn on FIG. 14B. FIG. 14C shows a flap valve 418, here directed inward to catch on a notch of the connector. The flap valve 418 could equally well be outwardly directed to catch on a notch of the connector as the connector is pulled through the flap valve 418 and thus through the lateral wall 424 of the bolster. This figure further shows a lumen 420 passing through the bolster, although other designs could be readily envisioned by skilled artisans in the field. The figure also shows a flared proximal end 422 adapted to abut against the mucosa of the vaginal wall. Again, other embodiments of the proximal end could be readily envisioned by those of ordinary skill in the art. In certain embodiments, the proximal end 422 may be modified, either to permit absorption by the body, or tissue incorporation or epithelialization. These modifications, falling within the scope of the present invention, will be readily achieved with no more than routine experimentation by practitioners of ordinary skill. FIG. 14D shows in more detail the swivel mechanism that permits the toggle 410 to pivot from an axial orientation to an orientation normal to the long axis of the delivery device. A pivot 430 is provided in the mid-portion of the toggle 410 that permits it to swivel on that axis. The pivot 430 also connects the toggle 410 to the connector 428, as shown in FIG. 14E. FIG. 14F presents an alternate embodiment for tissue fixation, where a fixation device 432 is equipped with folding arms 444 that are folded in a closed position when the device 432 is loaded in a cylindrical delivery device (not shown) When the target tissue is reached by the delivery device, it is withdrawn, leaving the fixation device 432 in place. As the delivery device is withdrawn, the arms assume an extended position 448, as shown in FIG. 14G. The force urging the arms outward may be an elastic force provided by the material from which the arms are made, or it may be a force produced by a SMA, or it may be any other force that is recognized in the relevant arts.

Figure 15A:
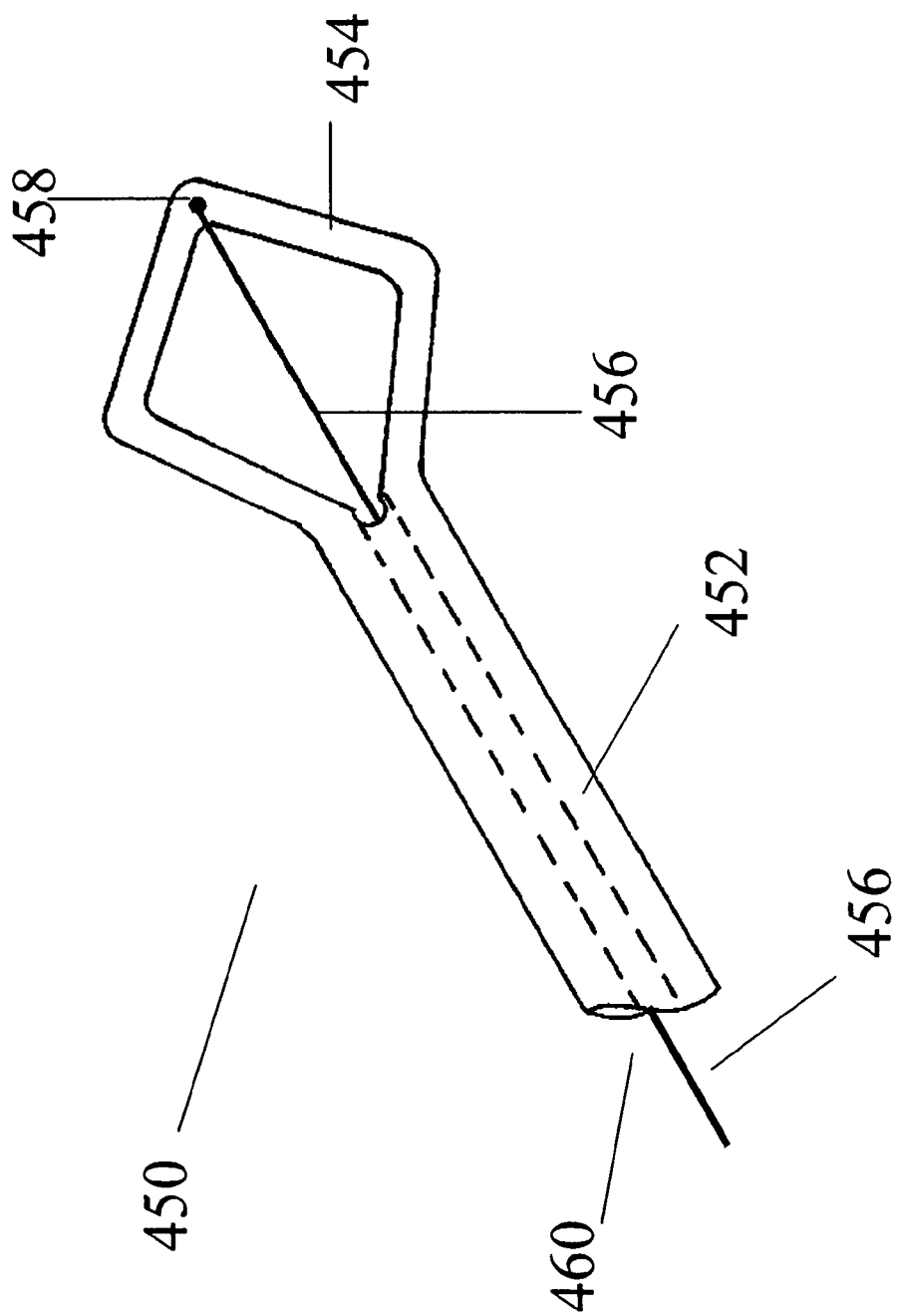
FIGS. 15A–D show in more detail embodiments of fixation systems and devices useful for the methods of the present invention.
Figure 15B:
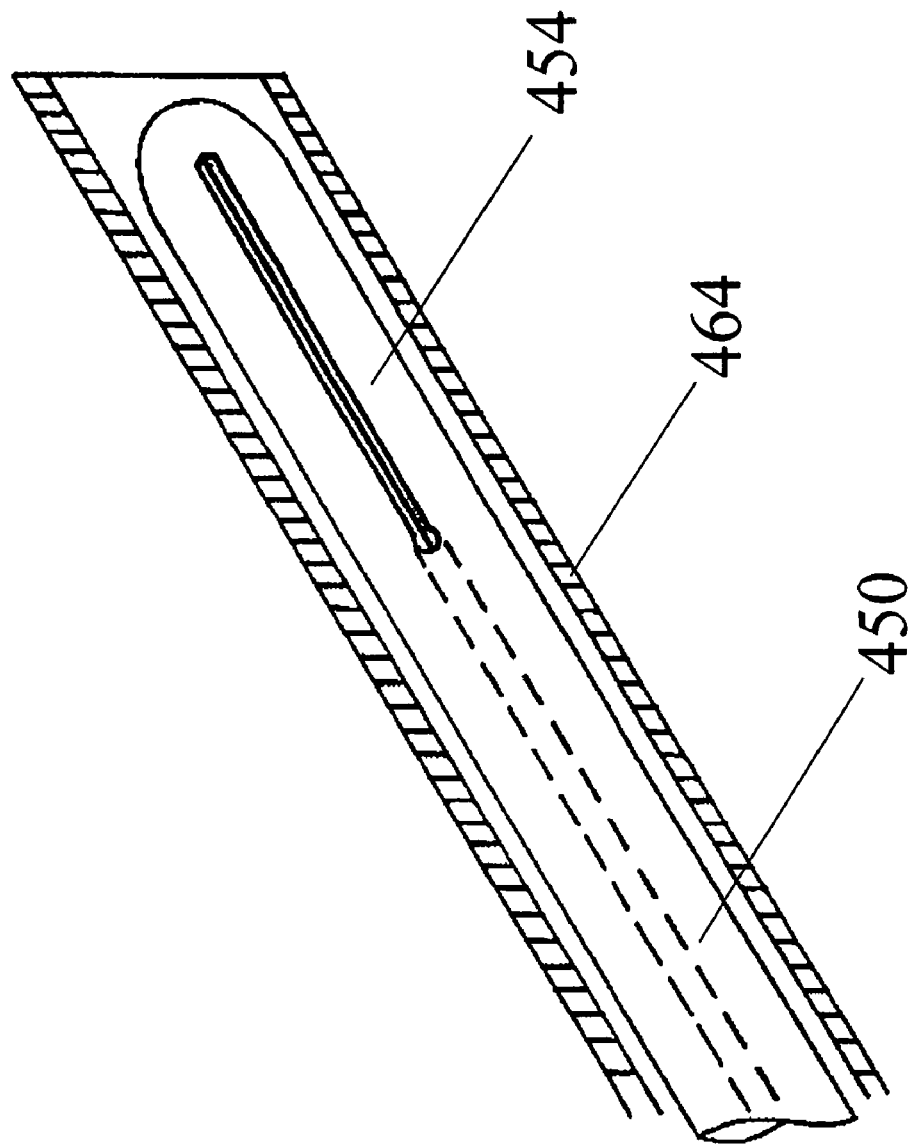
Figure 15C:
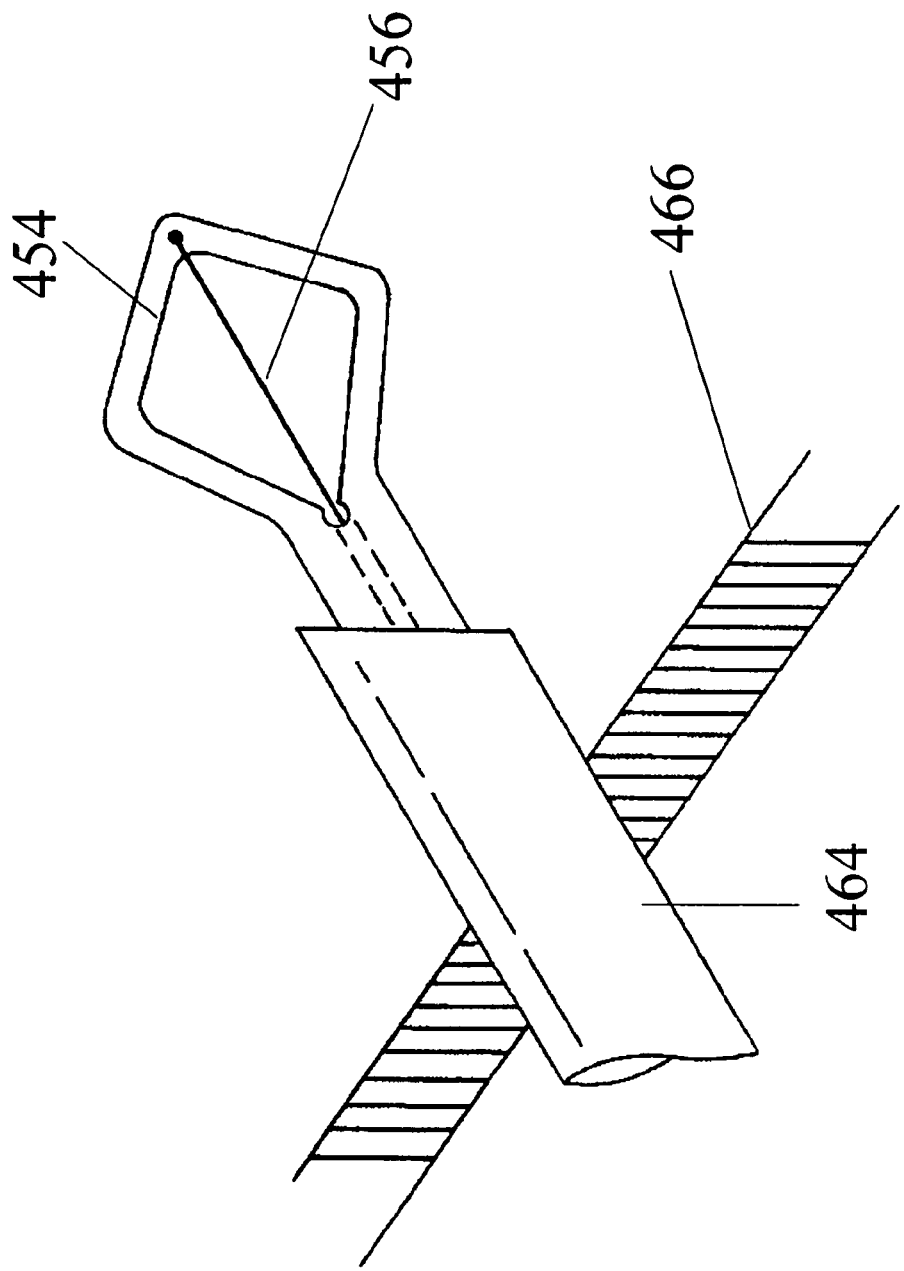
Figure 15D:
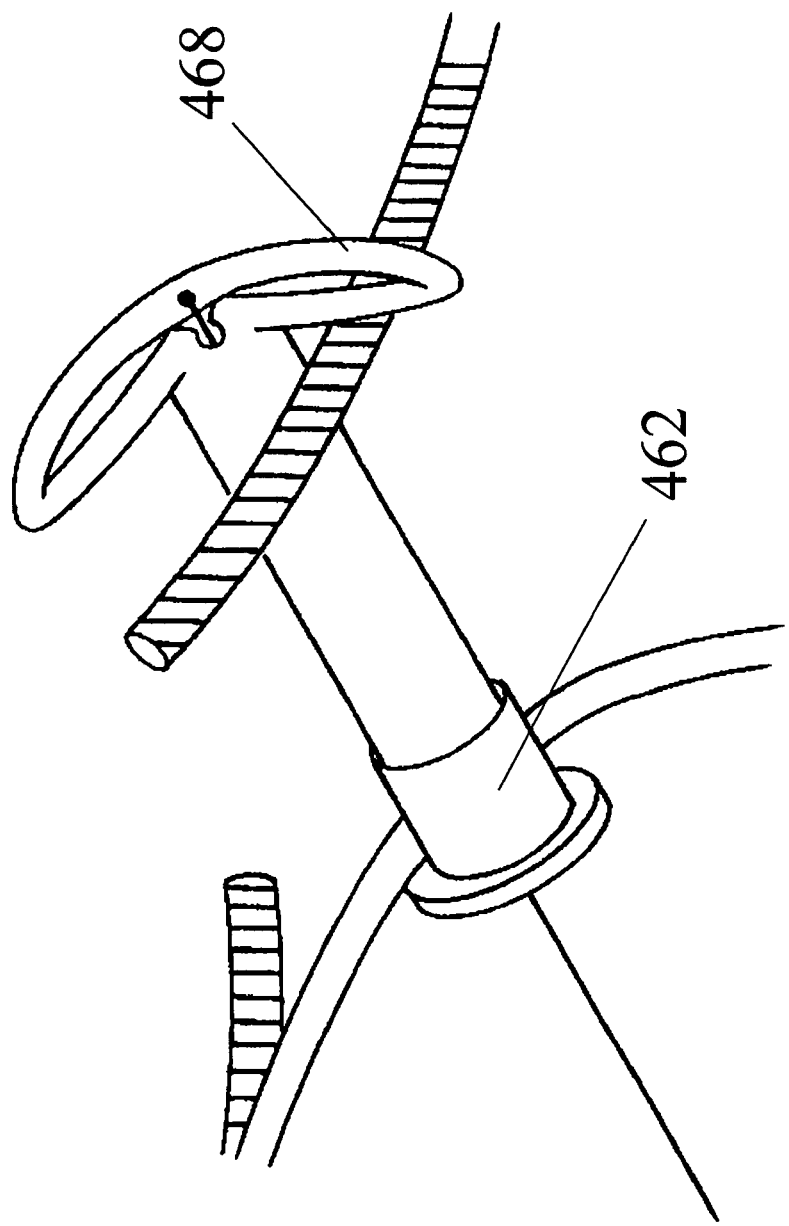

FIGS. 15A–D show an alternate embodiment of a fixation device 450 adapted for positioning in a soft tissue, and further adapted for ready removal. In FIG. 15A, a fixation device 450 is shown, comprising an expandable end 454 to the distal end 458 of which is affixed a pull wire 456 or a monofilament suture. The pull wire 456 passes through the hollow shaft 542 of the fixation device 450 to emerge through the proximal end 460. The proximal end 460 is adapted to be used with a bolster, as seen in FIG. 15D. To insert the fixation device 450, it is placed within a delivery device that includes a distal needle 464. The expandable end 454 is compressed so the device 450 can fit within the needle 464, as shown in FIG. 15B. FIG. 15C shows the needle 464 having penetrated an anchoring tissue 466. As the needle 464 is withdrawn, the expandable end 454 assumes its expanded contour. By further withdrawing the needle and further applying traction to the pull wire 456, the shape of the expandable end 454 can be further altered, as seen in FIG. 15D. A proximal pull on the pull wire 456 will deform the expandable end 454 so that it assumes a mushroom shape 468 or some other shape intended to affix it in the tissues. The expandable end 454 is held in this mushroom shape 468 by continuous traction on the pull wire 456. To secure two tissues together, tension is applied to the pull wire 456 and the pull wire 456 is inserted through the bolster 462 and affixed thereto to provide constant tension. In order to remove the device, the pull wire 456 may be cut or disengaged, permitting the expandable end to revert from the mushroom shape 468 to its previous shape. Applying traction to the flexible expandable end 454 may permit its ready detachment from the tissues in which it has been embedded.

Figure 16A:
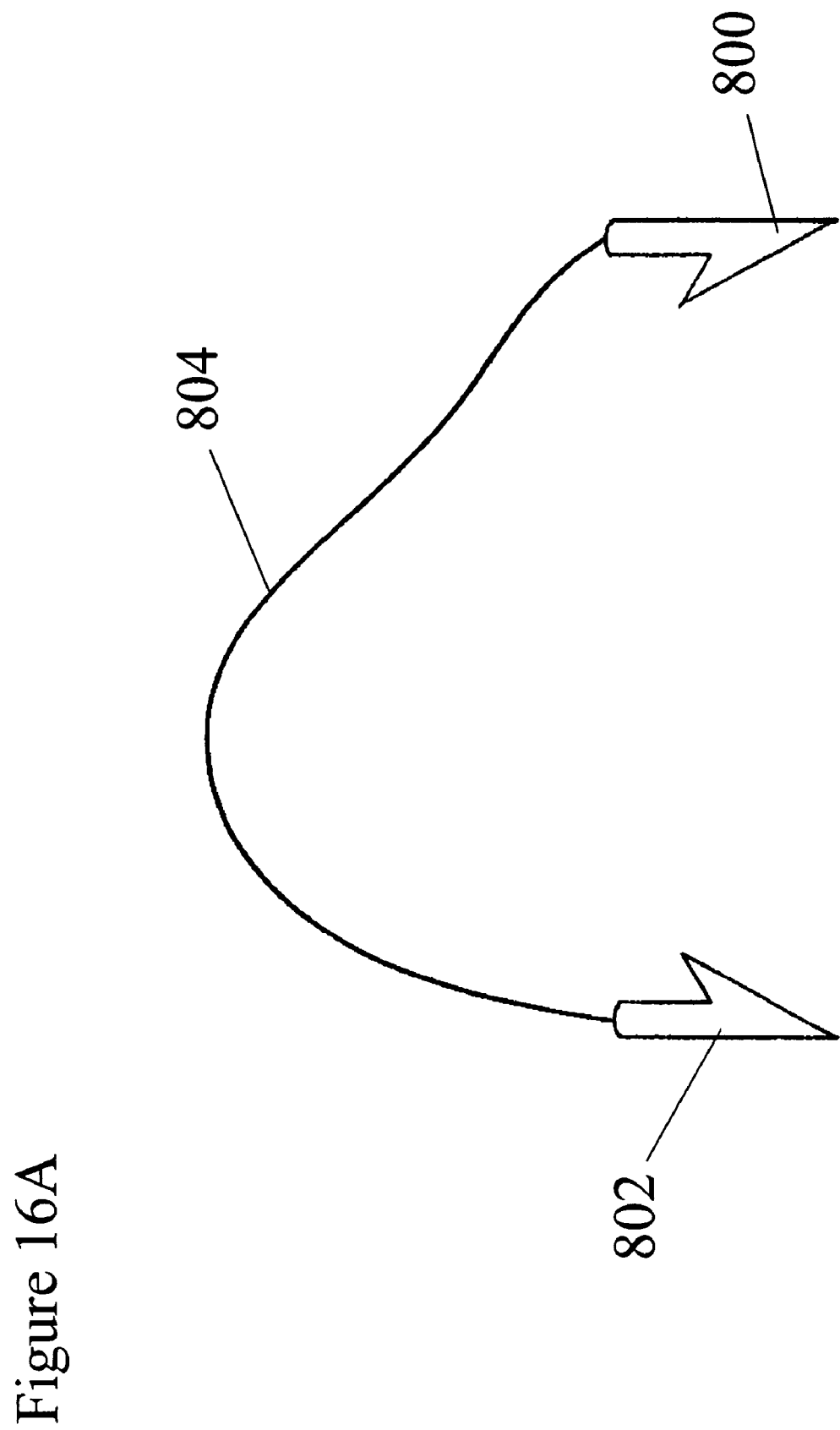
FIGS. 16A and B depict embodiments of fixation devices according to the present invention.
Figure 16B:
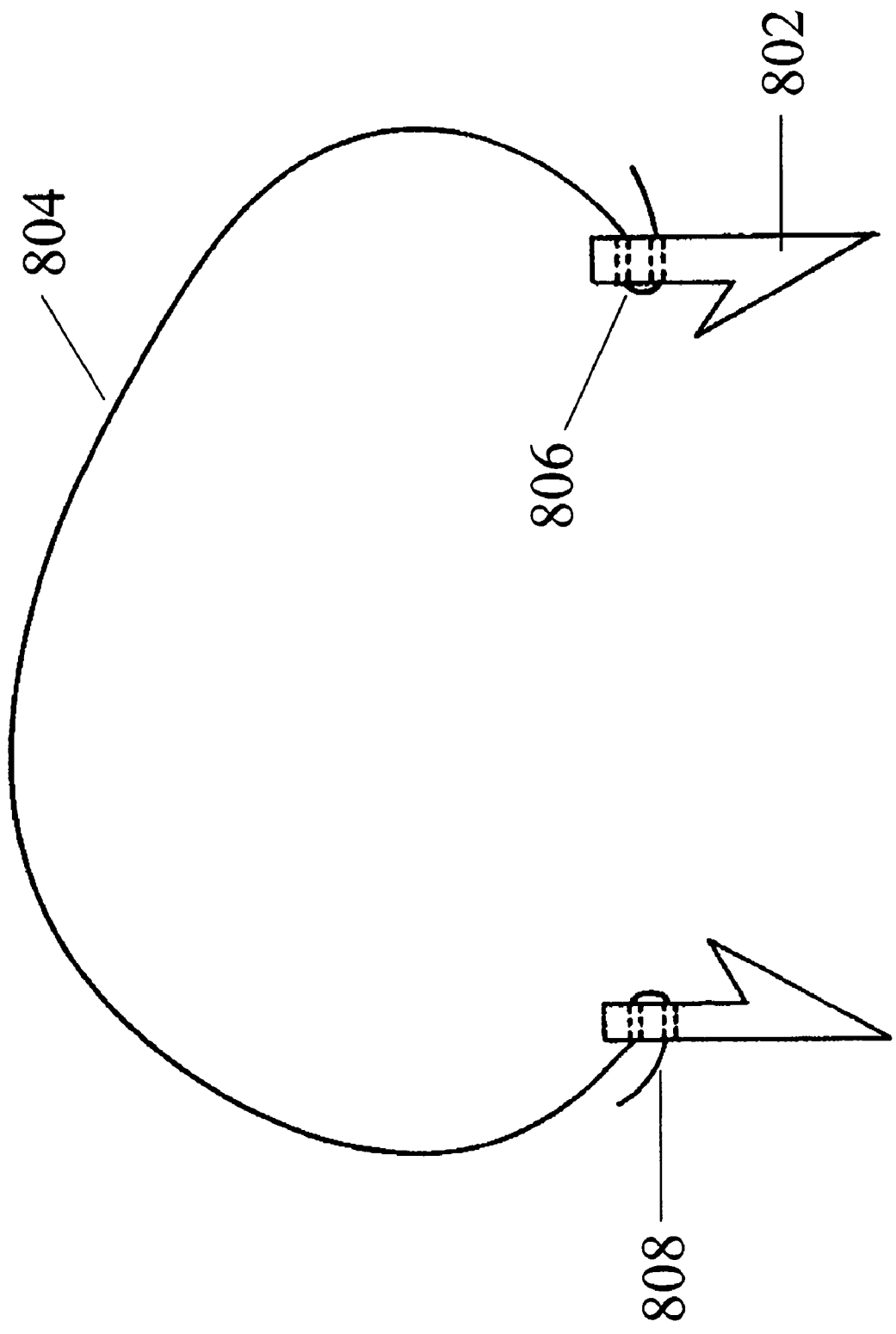

An embodiment permitting tension adjustment and ready release is depicted in FIGS. 16A and B. This embodiment shows two tissue fixation devices 802 connected by a flexible connector 804. Each tissue fixation device 802 is embedded in the target tissue and is anchored therein with the barb 800. The tension on the flexible connector 804 is then adjusted to the operator's specification. In FIG. 16B, a modification is shown wherein the flexible connector 804 passes through a connector lock 806 on the end of at least one tissue fixation device 802. The connector lock 806 permits varying tension to be applied to the connector 804 by proximally directed traction on its proximal end 804. In certain embodiments, the connector lock may be configured like the "quick releases" for backpack straps, wherein the straps are locked by threading them through an assembly that changes their direction, and wherein straps can be quickly released by manipulating the assembly.

Figure 17A:
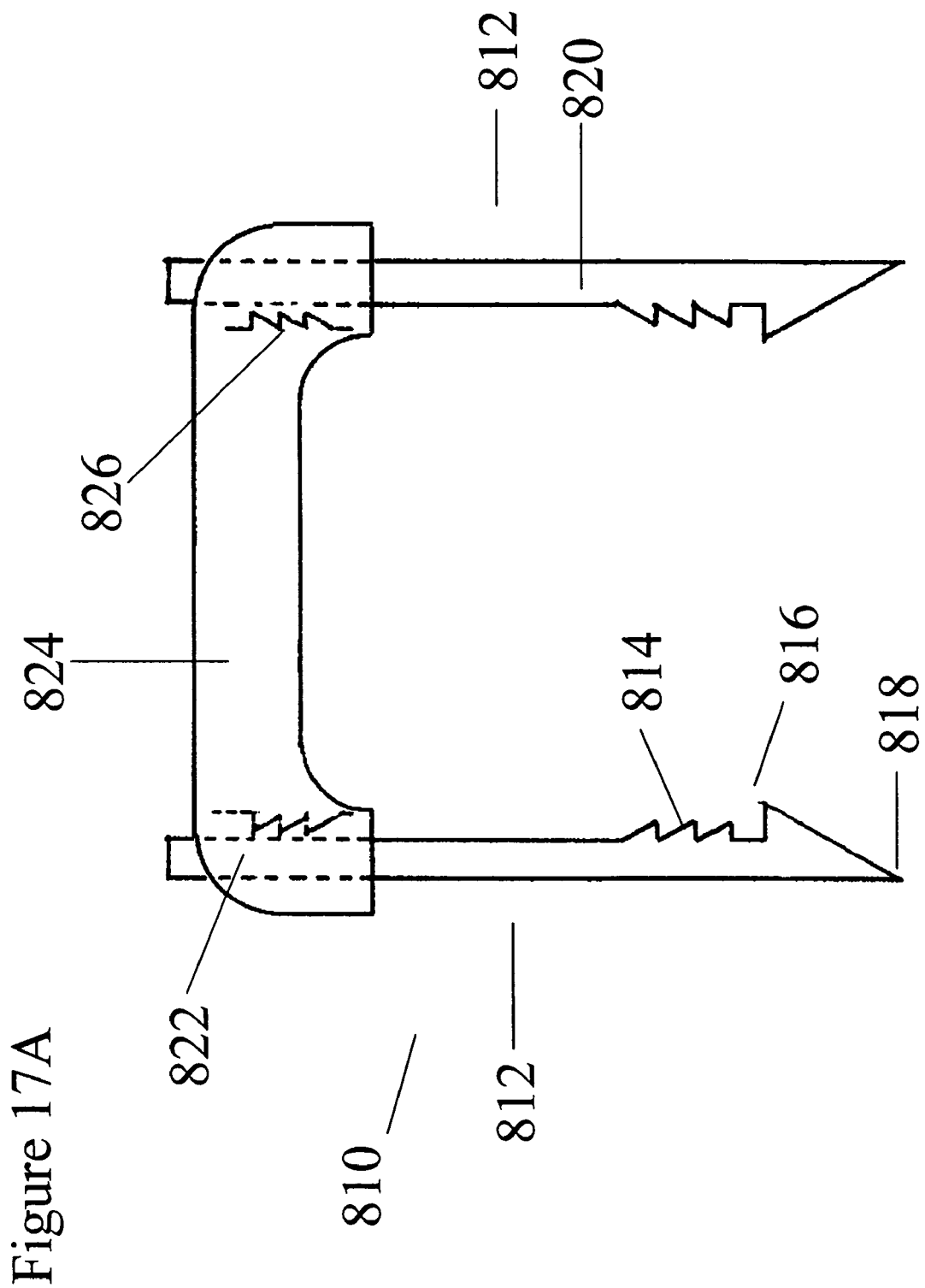
FIGS. 17A and B depict embodiments of fixation devices according to the present invention.
Figure 17B:
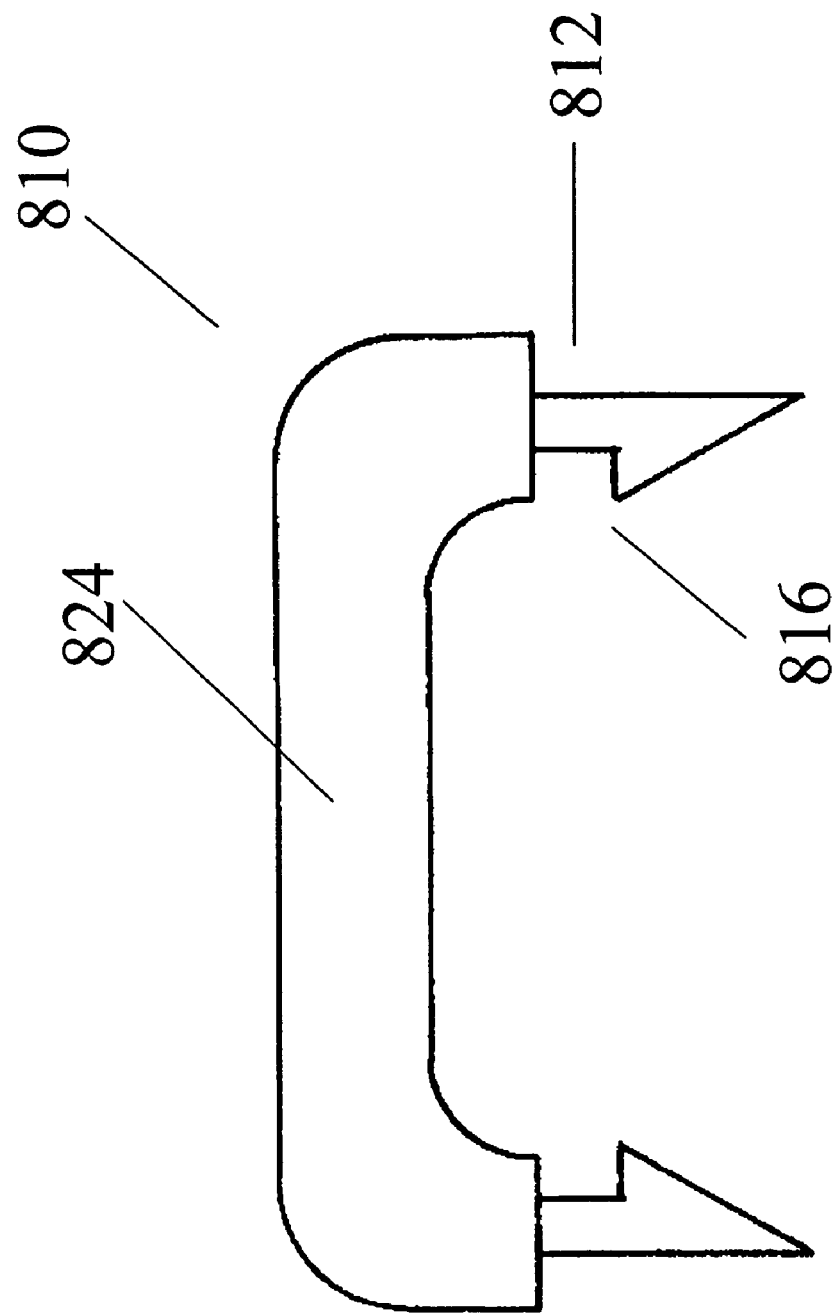
FIG. 17C depicts an embodiment of a top side of a ratchet assembly according to the present invention.
Figure 17C:
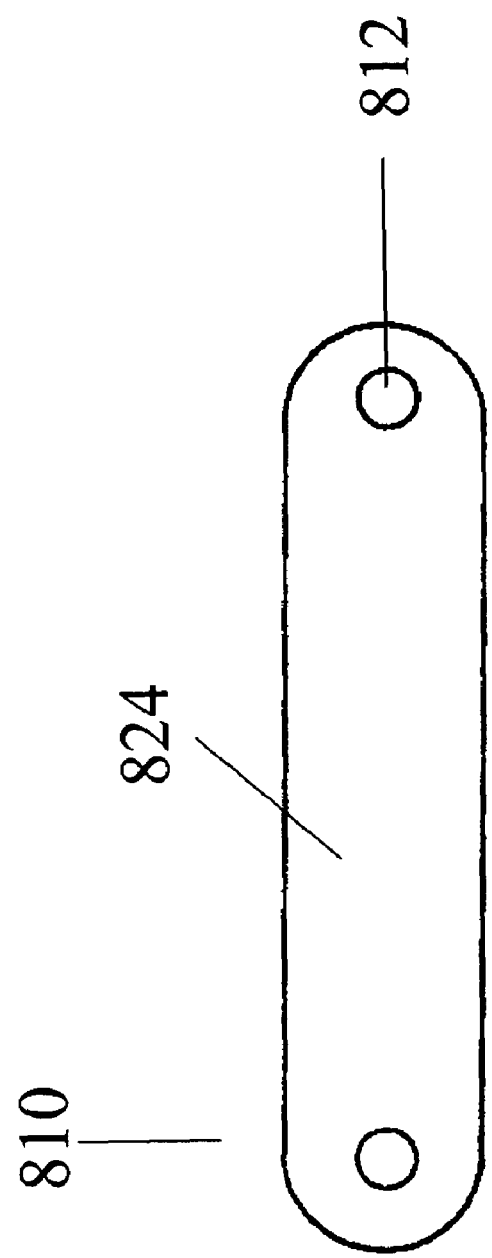

FIGS. 17A and B show a ratcheting assembly 810 to permit tension adjustment on a tissue fixation device. According to the systems and methods of the present invention, the tissue fixation device will be inserted from one side of the tissues only, and its distal end will reside wholly or in part within the target tissue, so that the distal end is not accessible for manipulation or for attaching to other components. A ratcheting system according to these systems and methods therefore is desirably configured so that it applies its ratcheting compression from one side only, preferably the proximal side. In the depicted embodiment, two arms 812 are provided for insertion into the tissues. Each arm 812 is comprised of a shaft 820 bearing a series of ratchet teeth 814. In the depicted embodiment, a barb 816 is provided for engaging the target tissues, although other engagement mechanisms may be readily envisioned. An insertion point 818 is further provided at the distalmost end of the arm 812. In the depicted embodiment, each arm 812 passes through a channel 822 in a horizontal affixation member 824. The arm 812 may pass completely through this channel 822 to exit the proximal side of the affixation member 824. Within the channel is a set of ratchet teeth 826 shaped to interdigitate with the ratchet teeth 814 on the arm 812. While a set of interdigitating ratchet teeth are depicted in this figure, it is understood that they may be modified or replaced by any system of cooperative, interdigitating structures that permit a ratchet-like variable affixation of the position of the horizontal affixation member 824 with respect to the arms 812. In the depicted embodiment, the ratcheting assembly 810 can be driven through a first tissue into a second tissue, with the insertion points 818 of the device entering the second tissue. The affixation member 824 which has remained external to the first tissue may be ratcheted down on the arms 812 to apply coapting tension between the first and the second tissues. Any proximal part of the arms 812 that protrude proximally through the affixation member may be cut or otherwise modified so that they do not protrude when the affixation procedure is completed. FIG. 17B depicts a ratcheting assembly 810 wherein the affixation member 824 has been snugged down on the arms 812 and any proximally protruding portion of the arms 812 has been removed. Barbs 816 are present in the depicted embodiment to grasp the anchoring tissue. FIG. 17C depicts a top side of a ratchet assembly 810 showing the arms 812 passing through the affixation member 824. In the depicted embodiment, the arms 812 have been trimmed so that they do not protrude from the affixation member 824.

Figure 18A:
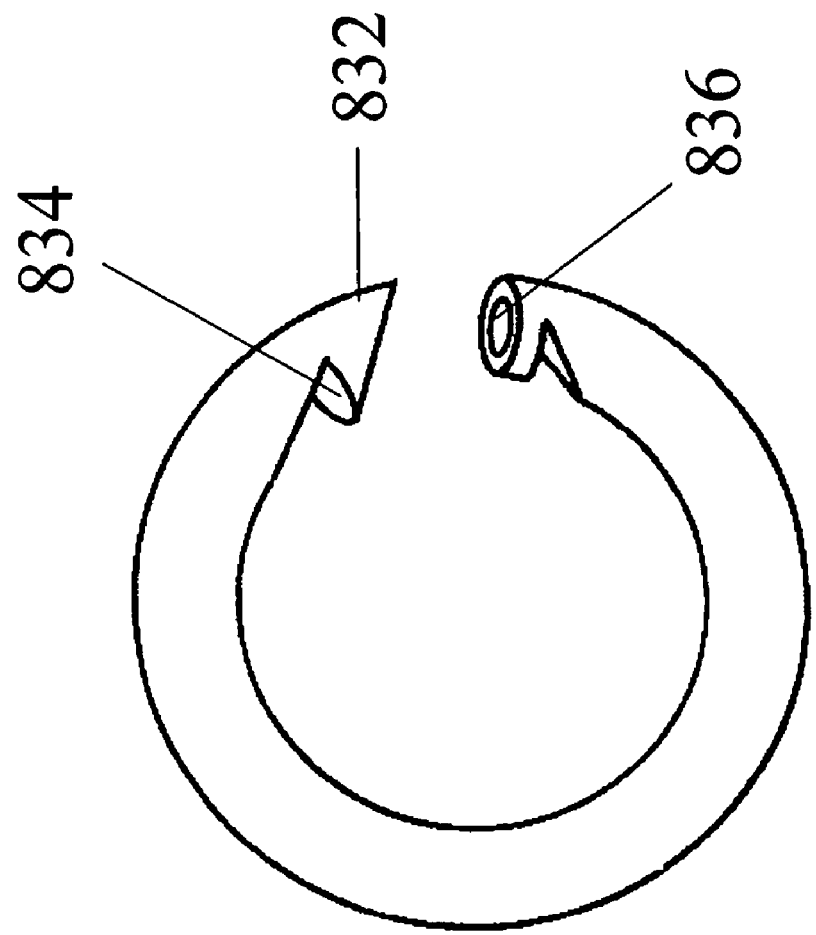
FIGS. 18A and B depict embodiments of fixation devices according to the present invention.
Figure 18B:
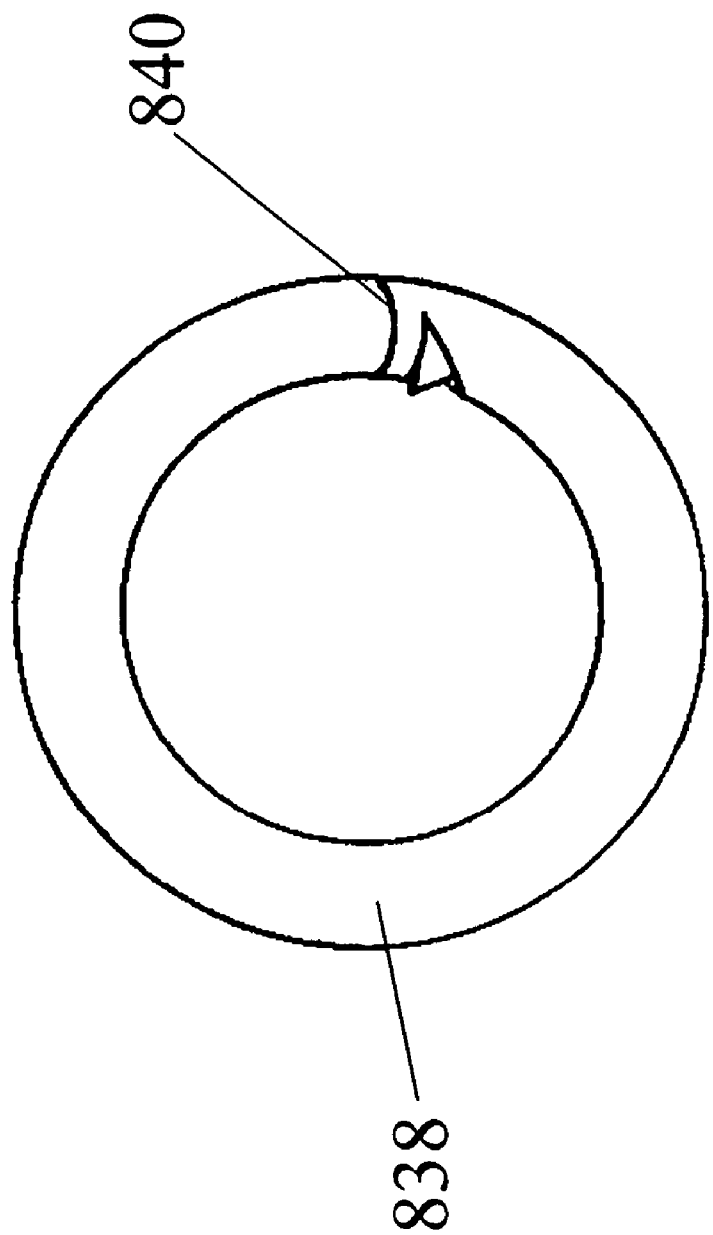

FIG. 18A shows a ring shaped fixation device 830 adapted for easy removal from tissues even after it has been securely inserted. An insertion point 832 is provided to permit penetration of target tissues. A barb 834 is provided in the depicted embodiment to engage the tissues and prevent backsliding as the fixation device 830 is urged forward. A locking channel 836 is shaped to receive the insertion point and to secure this and the barb within a passage interior to the device 830. Once the point 832 and the barb 834 are fastened within the locking channel 836, there are no sharp points directed externally to injure the patient. Rather, the tissues are held encircled by the closed loop 838 formed by the fixation device 830, as shown in FIG. 18B. FIG. 18A further shows a seam 840 representing the place where the insertion point and the barb have entered the locking channel. In a preferred embodiment, directing force against this seam may permit the barbed end to become detached from the locking channel. If this takes place, the ringed fixation device may be readily freed from the tissues relatively atraumatically. Once the barbed end has been detached from the locking channel, the operator may continue to push the barbed end through the tissues until it exits. Further traction on the barbed end may free the fixation device from the tissues.

Figure 19A:
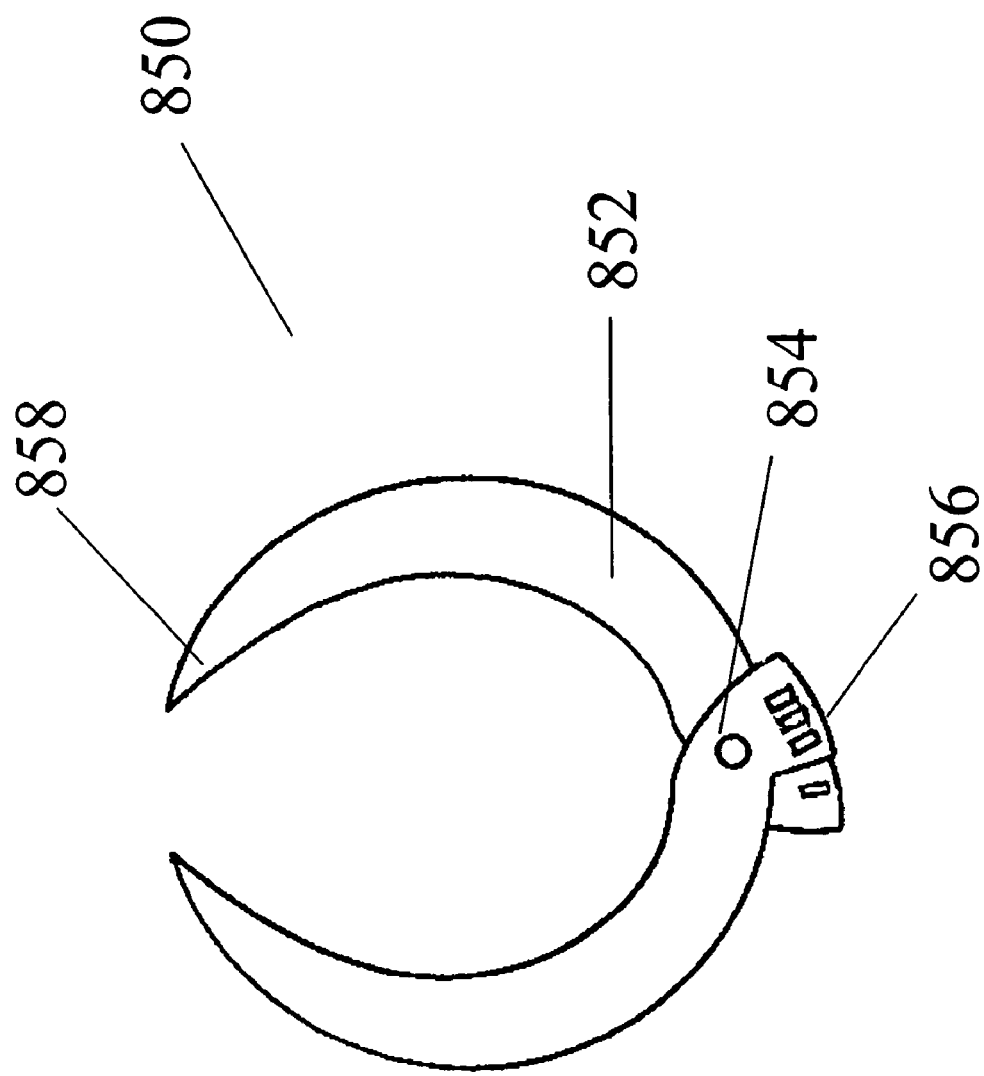
FIGS. 19A and B depict embodiments of fixation devices according to the present invention.
Figure 19B:
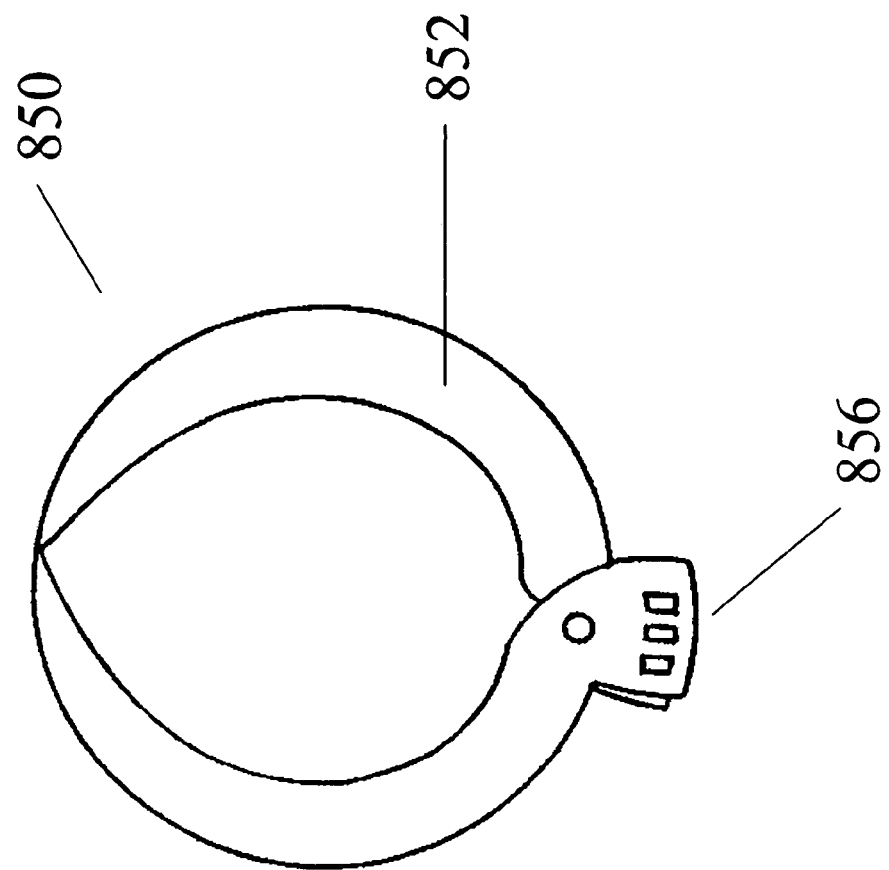

FIGS. 19A and B show yet another embodiment of a fixation device 850. In this embodiment, two pincers 852 are provided, attached to each other by a hinge and capable of rotating inwardly with the application of inward force. When inserted into target tissue, the insertion points 858 of the pincers 852 penetrate and engage the tissue. A lock mechanism 856 located proximally can be activated after the pincers have adequately engaged the target tissue. FIG. 19B shows the pincers 852 of the fixation device 850 in a closed position to engage the target tissue therebetween. In the depicted embodiment, a lock mechanism 855 may be activated to hold the pincers 852 in their closed position.

Figure 20A:
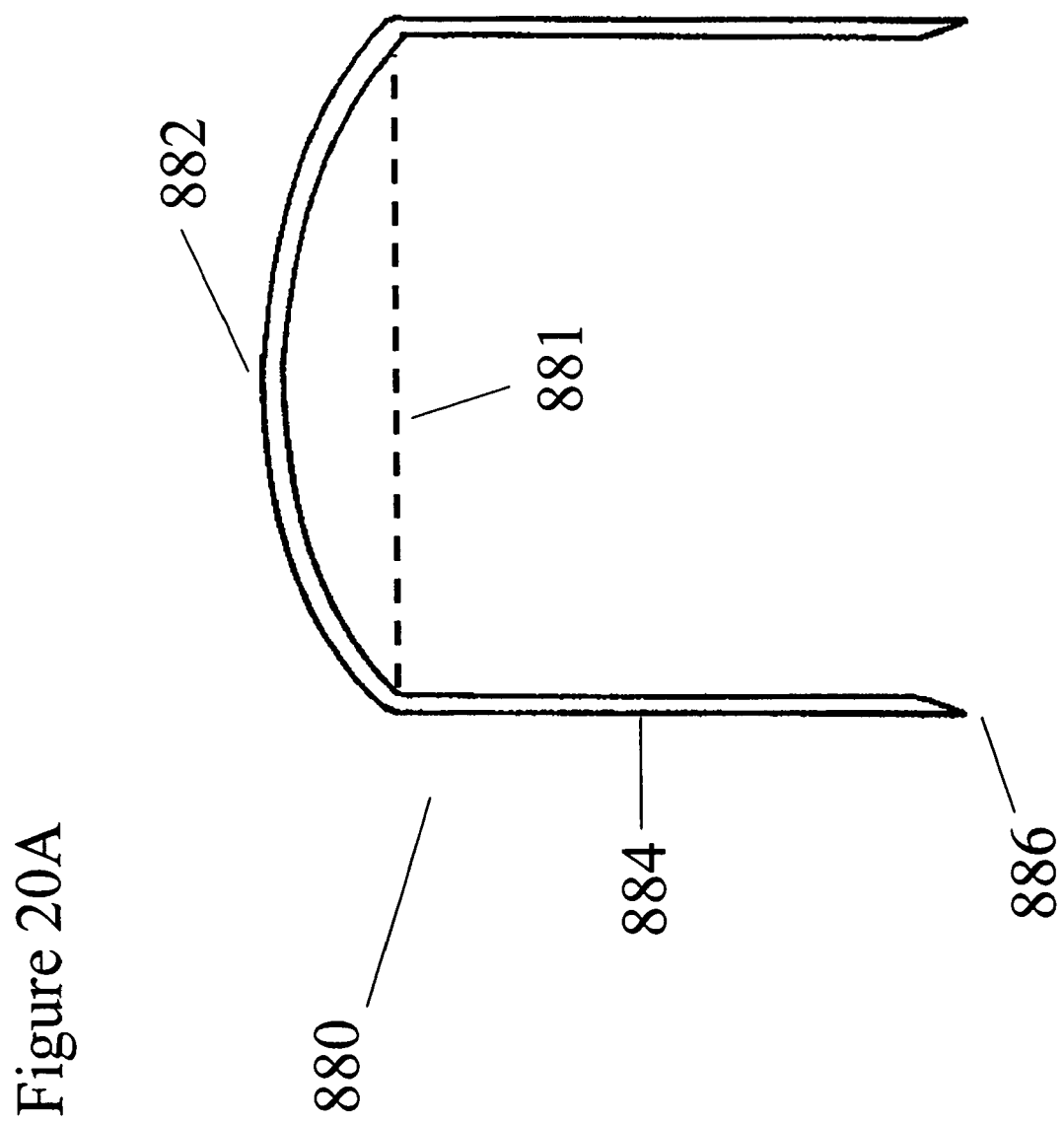
FIGS. 20A–D depict embodiments of fixation devices according to the present invention.
Figure 20B:
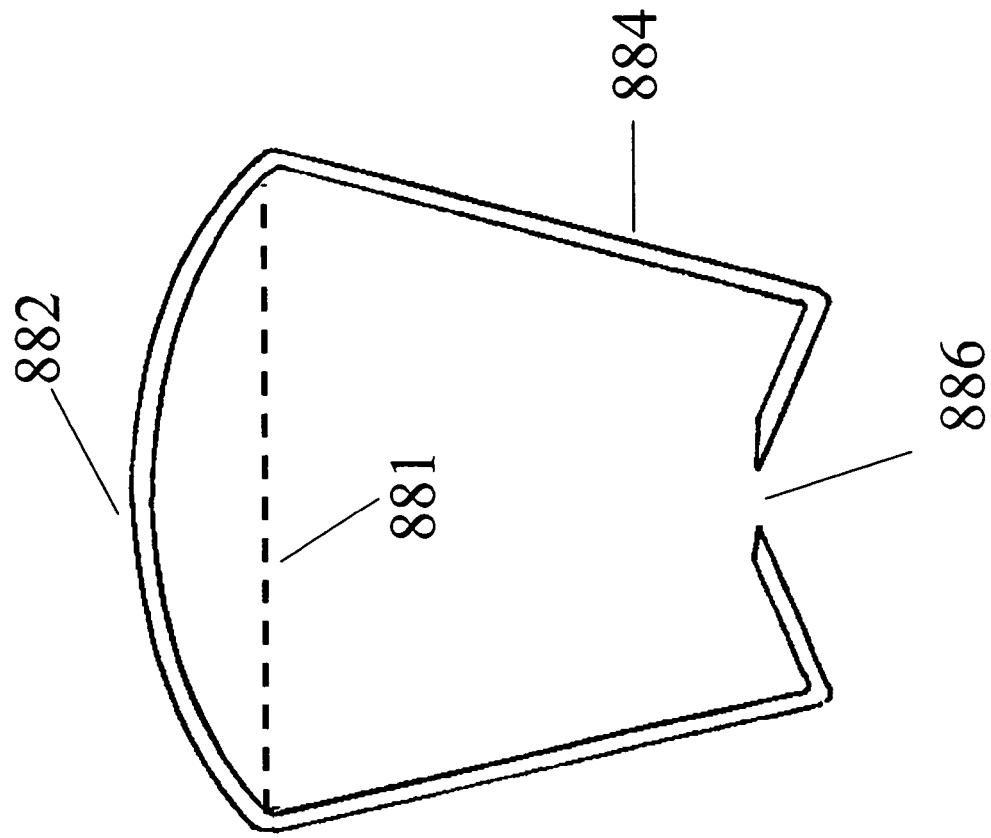
Figure 20C:
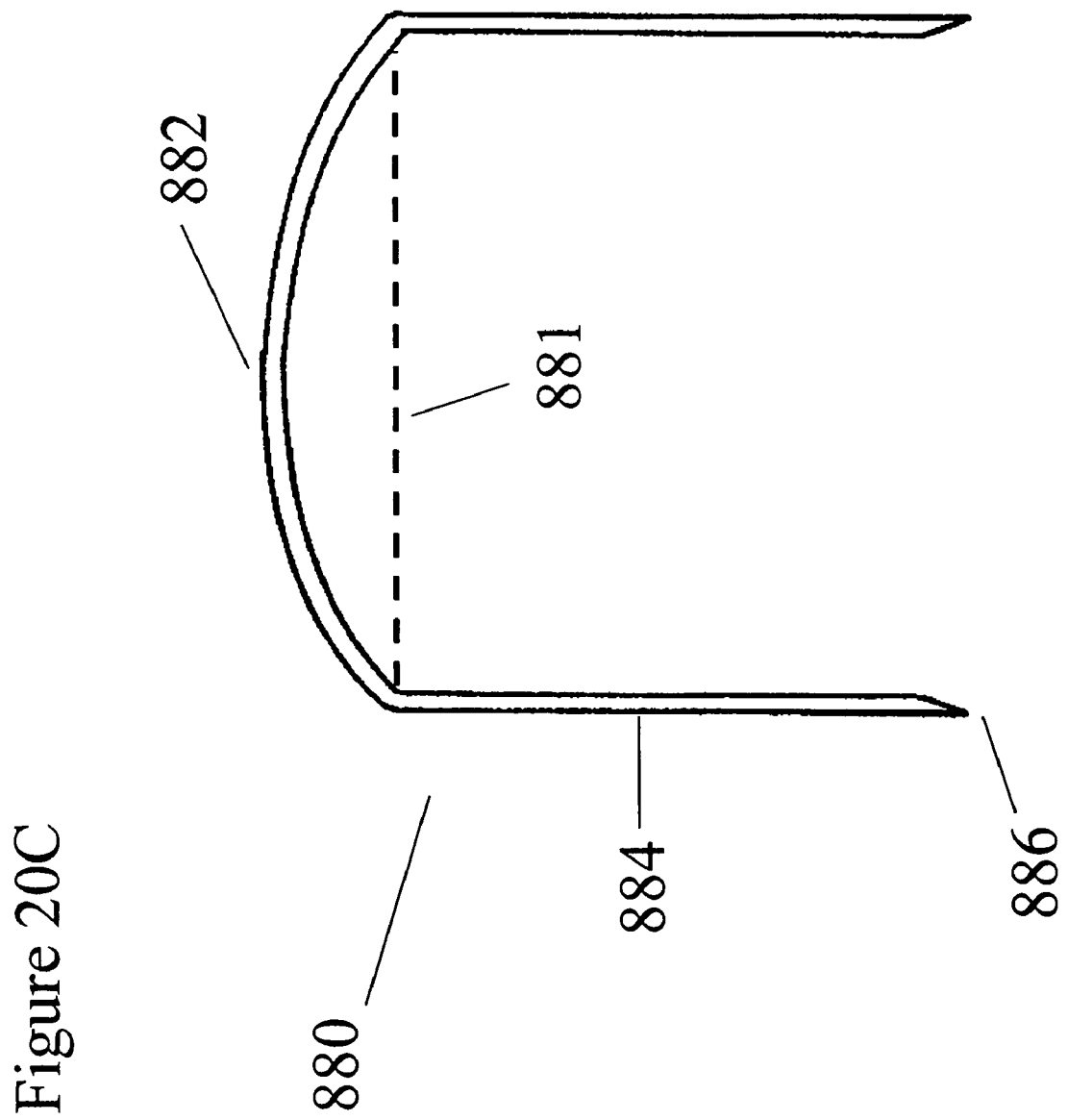
Figure 20D:
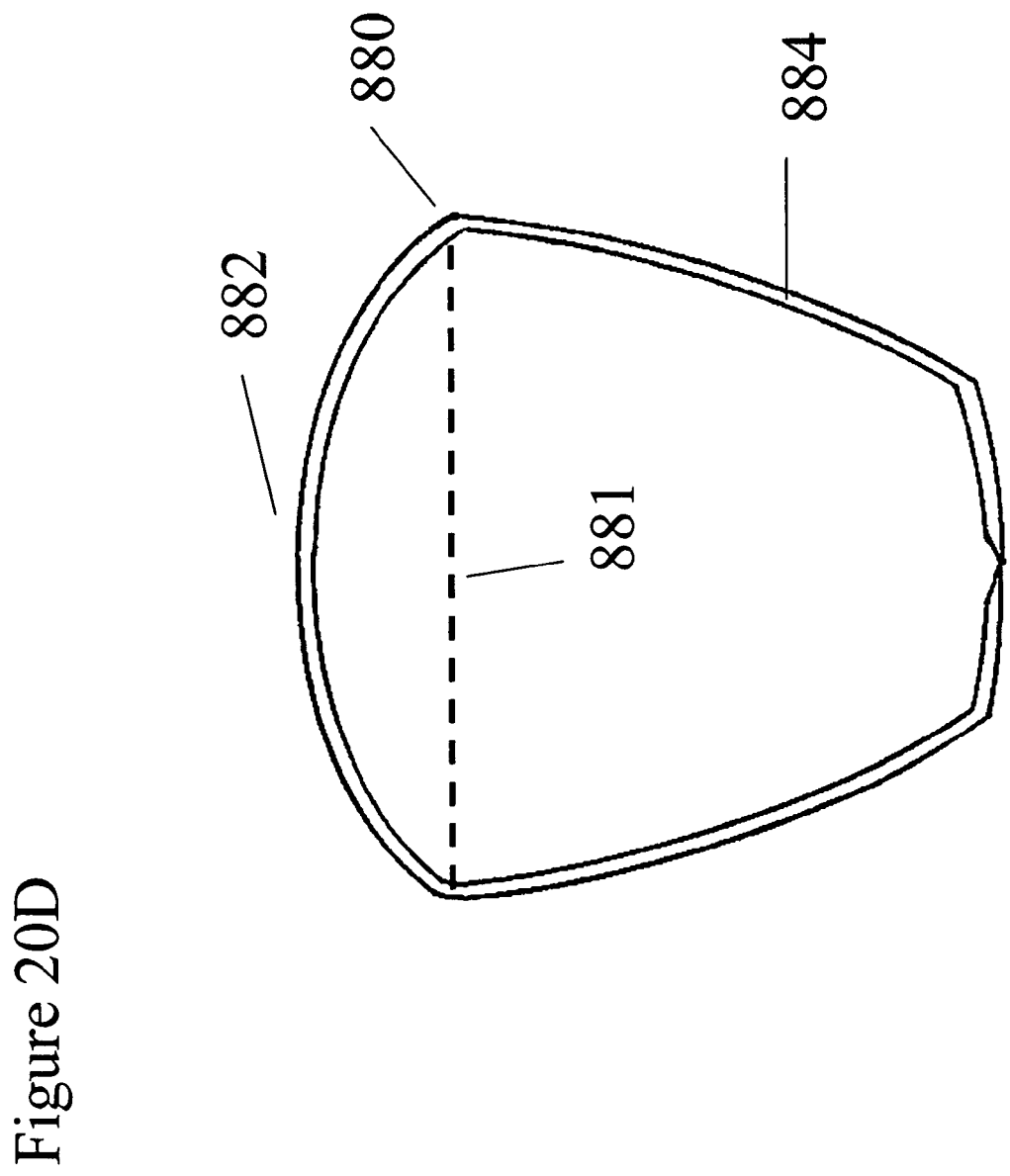
Figure 21A:
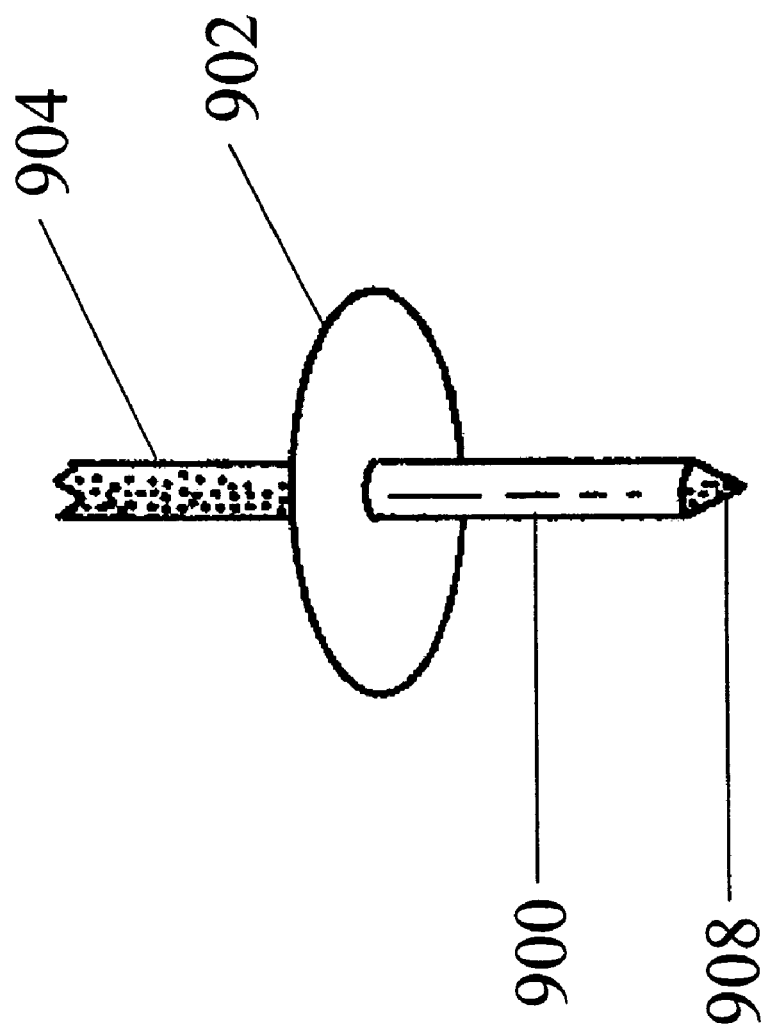
FIGS. 21A–I depict embodiments of fixation devices according to the present invention.
Figure 21B:
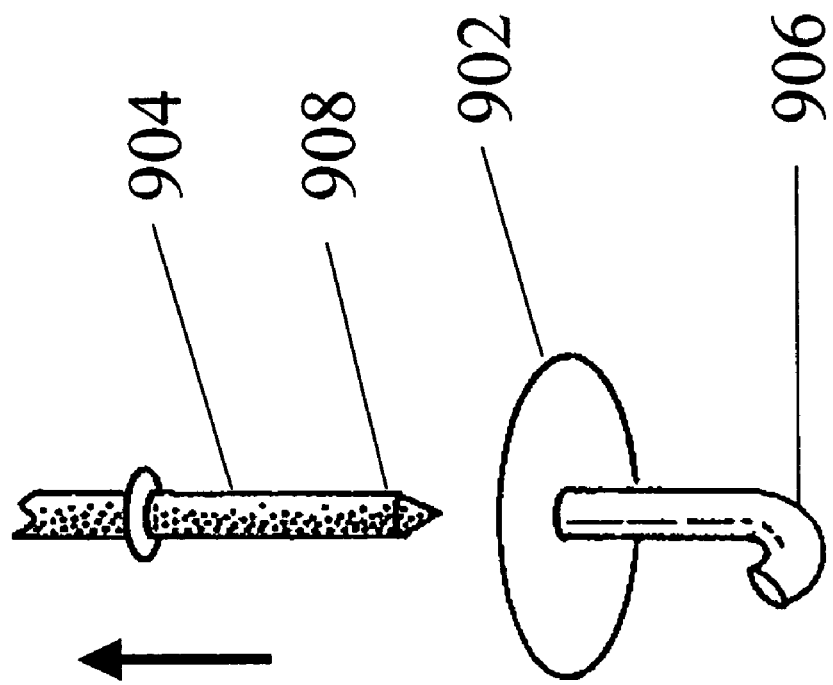
Figure 21C:
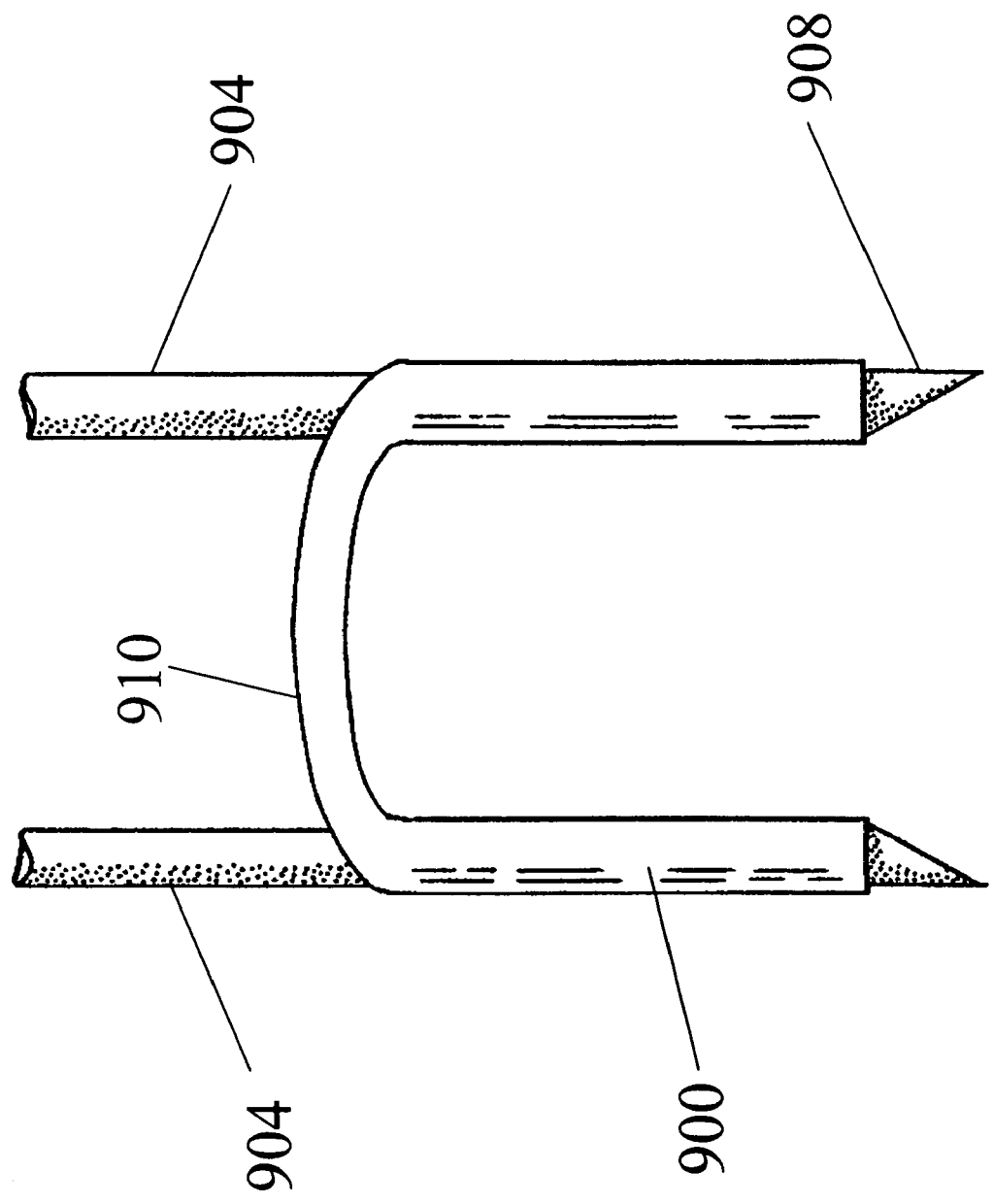
Figure 21D:
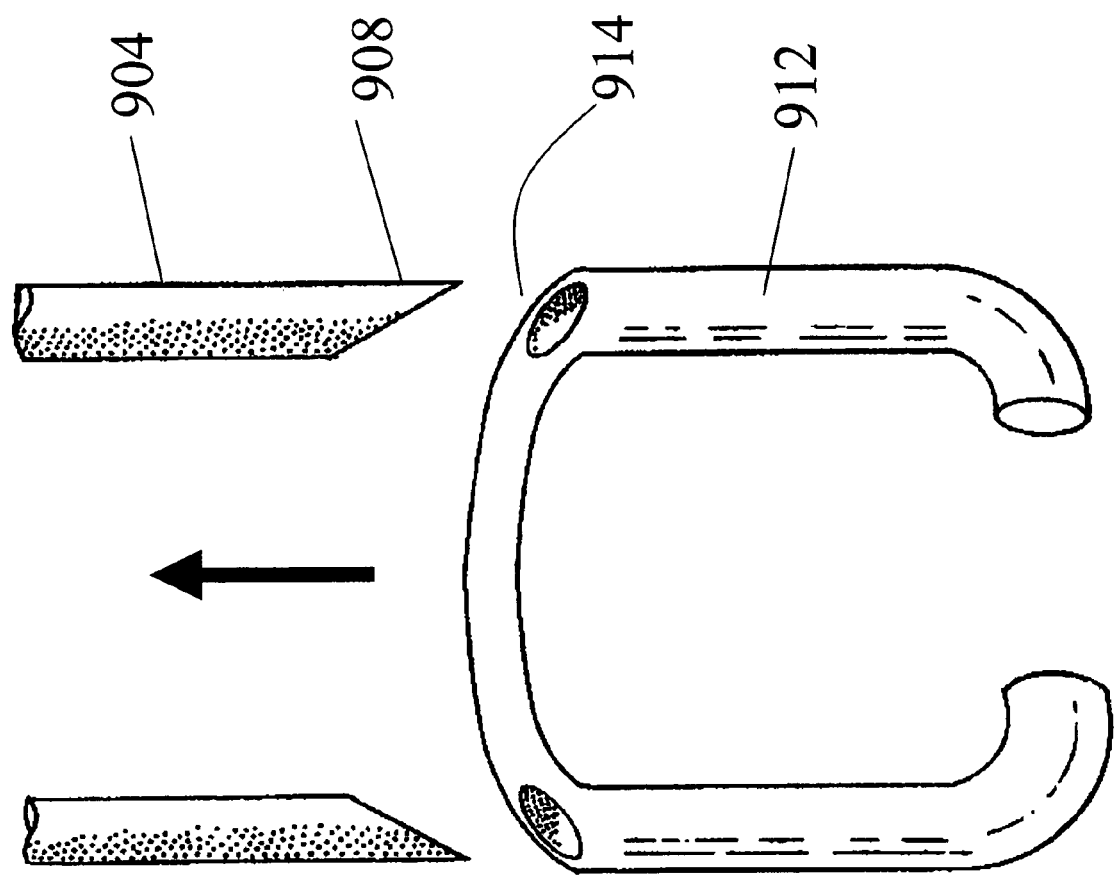
Figure 21E:
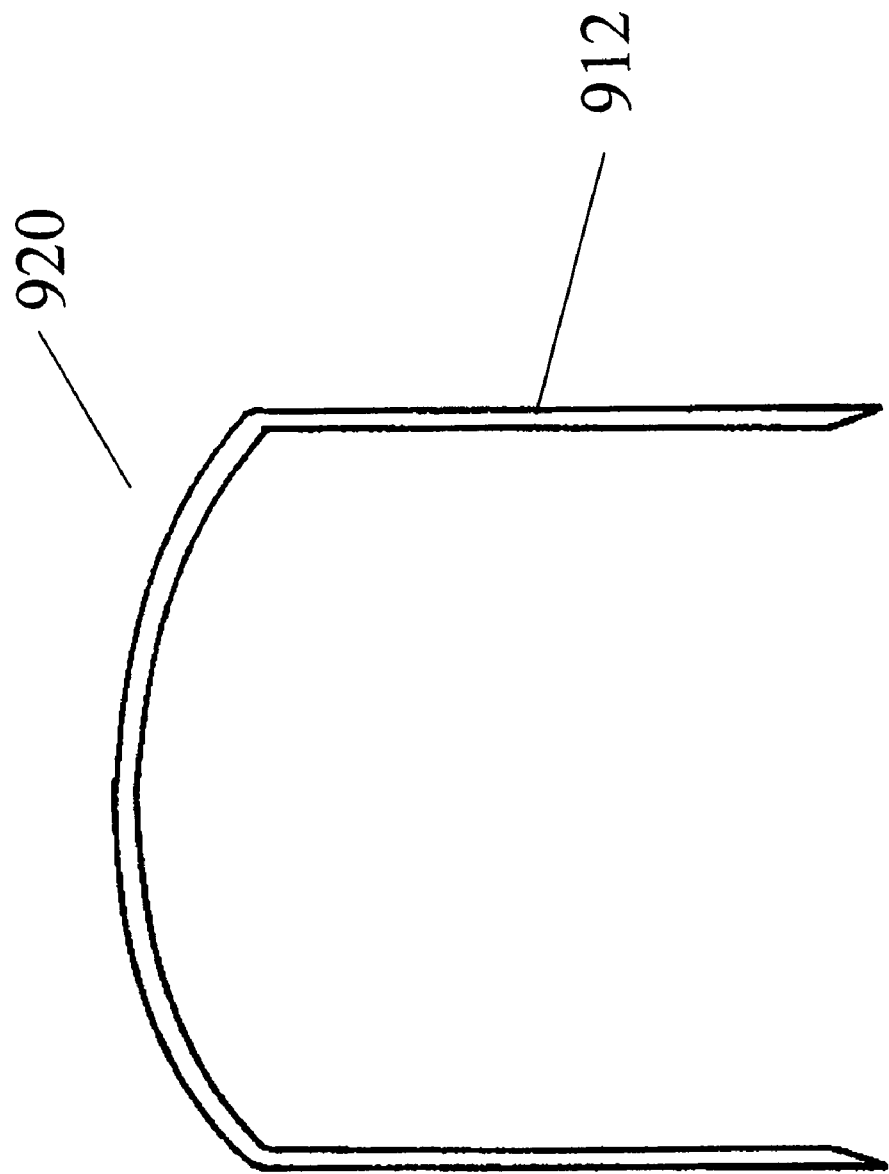
Figure 21F:
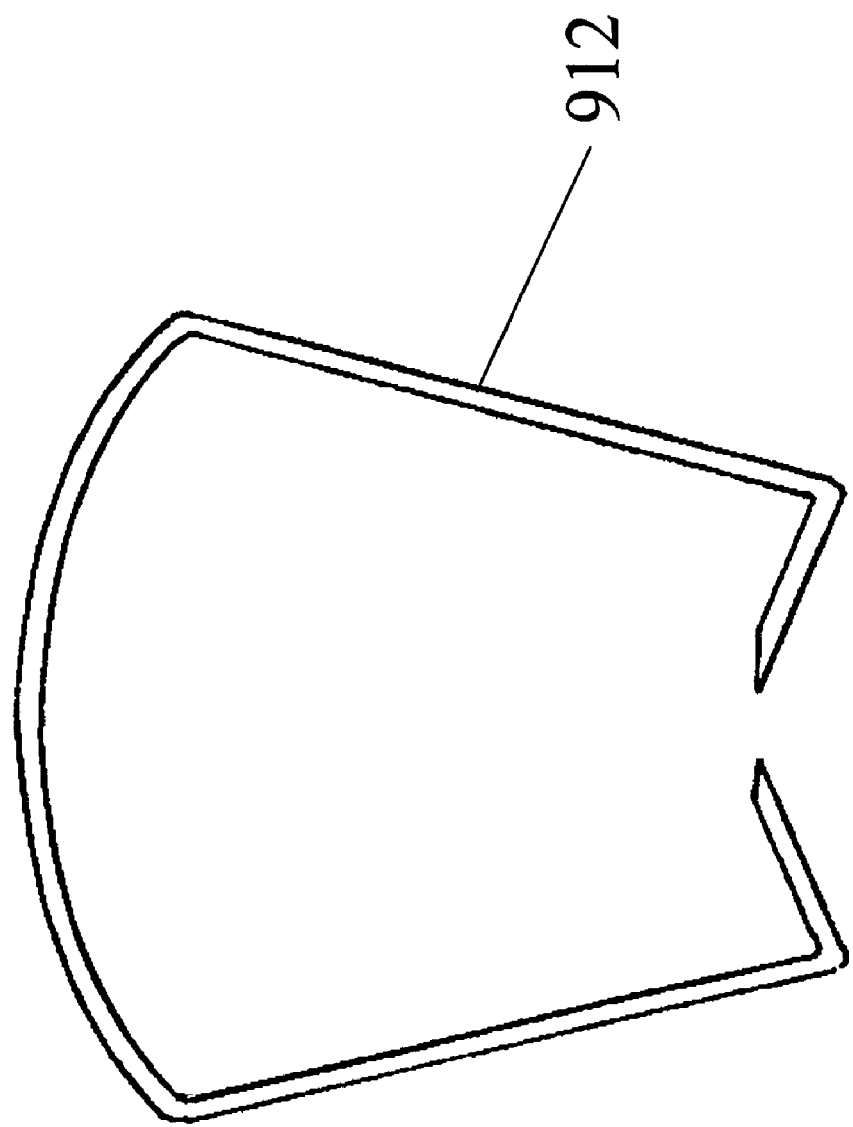
Figure 21G:
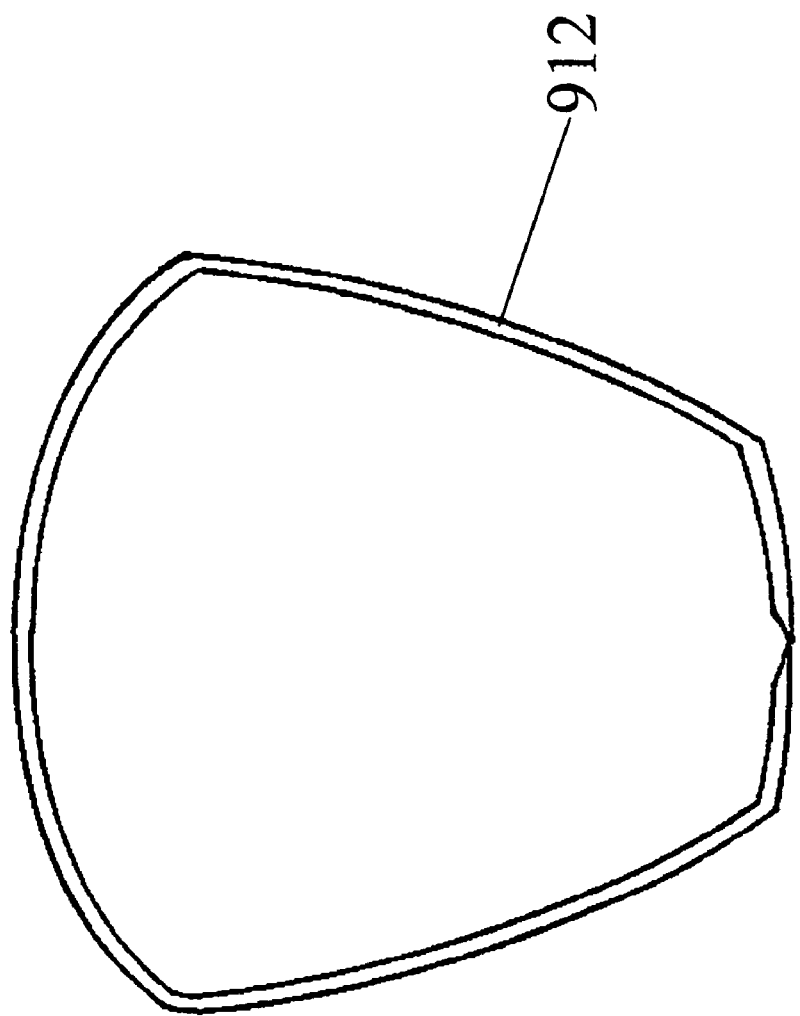
Figure 21H:
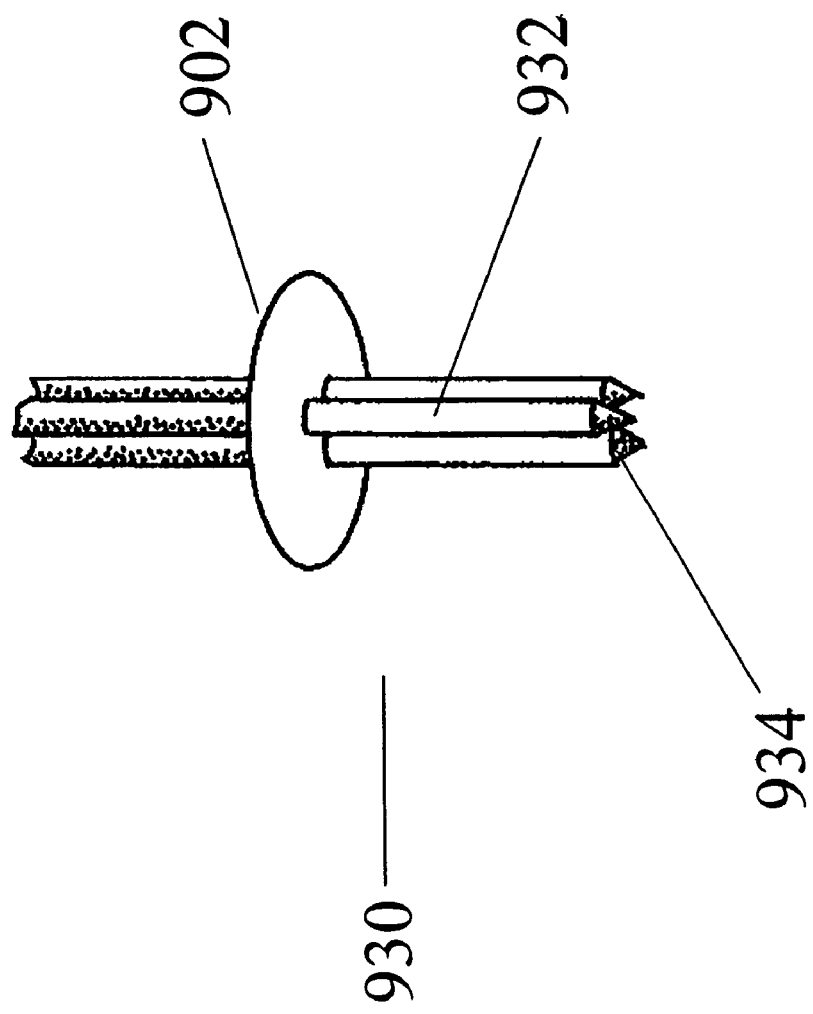
Figure 21I:
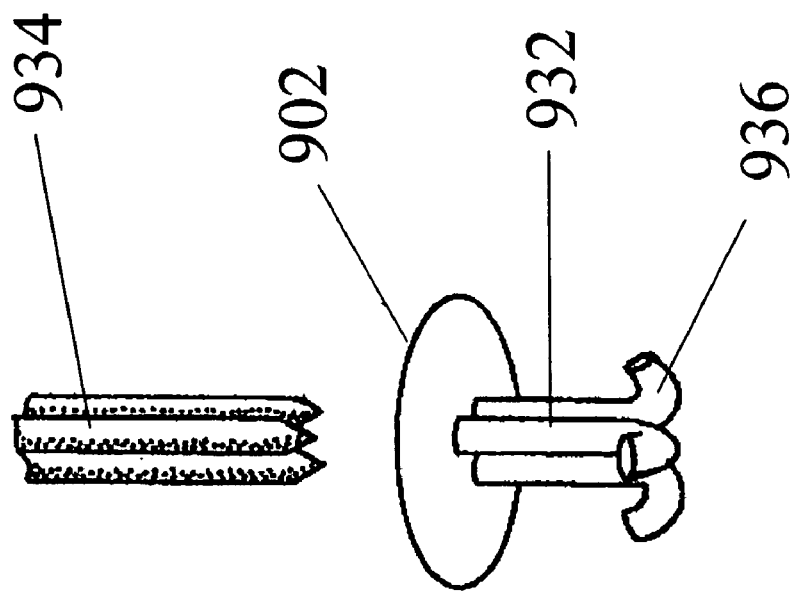

As has been mentioned previously, fixation devices according to the present invention advantageously are adapted for ready removal. The use of SMA and various SIM materials offers a mechanism by which easy insertion and ready removal may be achieved. FIGS. 20A–D depict embodiments where a shape memory alloy may be used to alter the shape of the fixation devices after heating. FIG. 20A shows a fixation device 880 according to the present invention ready for insertion. In the depicted embodiment, a horizontal bar 882 connects to a vertical arm 884 at each end. The dotted line 881 indicates the width of the device at the level of the horizontal bar 882. The vertical arms 884 are attached to the horizontal bar 882 at substantially right angles. Each vertical arm 884 is equipped with a penetrating end 886 dimensionally adapted for insertion through a first tissue into a second tissue. In an embodiment suitable for vaginal use, the entire vertical height of the fixation device 80 may be approximately 13 mm. Each vertical arm 884 is comprised of two segments, a proximal one about 8 mm in length and a distal one about 3 mm. in length. The length of the horizontal bar 882 may be about 10 mm. As shown in FIG. 20B, with the application of heat, the proximal segment of the vertical arm 884 is bowed inward somewhat, while the distal segment of the vertical arm 884 bends on itself. Since the penetrating end 886 of each staple is optimally located in the target tissue, application of heat to the depicted device may affix it firmly within the target tissue. As indicated by the dotted line 881, the width at the level of the horizontal bar 882 does not change. FIGS. 20C and D show modifications of the same structure. FIG. 20C show a fixation device 880 adapted for insertion into intact tissues according to the systems and methods disclosed herein. Once the insertion points 86 have entered the target tissue, then heat may be applied to the device 800. The application of heat may cause the fixation device 800 to bow in the distal part of its arms 884 and the distal part of the penetrating edge 888, as seen in FIG. 20D. FIG. 20D shows the penetrating ends 886 of the vertical arms 884 to be nearly touching, and further shows a smoother configuration with fewer angulated edges than the device shown in FIG. 20B.

A variety of embodiments are shown in FIG. 21 where issues of removability are addressed. FIG. 21A shows a hollow fixation device 900 that is inserted into the tissues by being carried on an introducer pin 904 with a sharpened insertion point 908. A proximal seat 902 is depicted that allows the fixation device 900 to apply pressure on proximal tissues, thereby to approximate them to distal tissues. As shown in FIG. 20B, once the fixation device 900 has reached the target tissue, the introducer pin 904 may be removed, permitting the hollow fixation device to assume its natural curve 906. The curve may be imparted to the hollow fixation device 900 by selecting a flexible material that can be shaped into a curve and that can tolerate being straightened temporarily by the introducer pin 904. Other materials, such as SMA, may be used, as well as those materials that will be apparent to ordinary skilled practitioners. 21C and D show an arrangement where two fixation devices 900 are joined together by a horizontal bar 910. Introducer pins 904 are inserted into each arm 912 of the fixation device, thereby straightening each arm. When the fixation device 900 is properly inserted into the target tissue, the introducer pins 904 may be removed, permitting the device to assume a curved position. Removal of the depicted embodiments may take place by reinserting the introducer pin 904 so that the fixation device straightens out, permitting its removal. A hole 914 for the insertion of the introducer pin 904 is seen on each lateral aspect of the horizontal bar 901, permitting access of the introducer pin 904 into the hollow interior of each arm 912. FIGS. 21E–G figuratively depict an embodiment where a fixation device 920 is made of a material that exhibits a two-way shape memory affect. When inserted into tissue at body temperature, the fixation device 920 may take on a particular shape, as shown in FIGS. 21F and G. These shapes show the arms 912 having assumed a bent or a closed position, thereby encircling tissues. As generally depicted, these fixation devices may be termed staples. As used herein, a staple may be any structure wherein the arms angulate inward with the application of a force (including a force intrinsic to the device itself, such as the change in shape that occurs in a SMA with heating or cooling), so that the arms encircle the designated tissue. To remove the fixation device 920, it may be cooled so that it returns to a shape with straight arms 912, as shown in FIG. 21E. Once the arms have straightened, the device 900 may be readily removed. FIGS. 21H and I show an embodiment of a fixation device 930 comprised of a plurality of hollow tubes 932 that each contain an introducer pin while the device 930 is inserted into body tissues. Once the device 930 has been positioned within the target tissues, the introducer pins 934 may be removed, allowing the hollow tubes 932 to revert to their naturally curved state 932. As mentioned above, a variety of materials may be used to fabricate the hollow tubes 932, including polymers and metallics, particularly those comprising shape memory alloys.

Figure 22A:
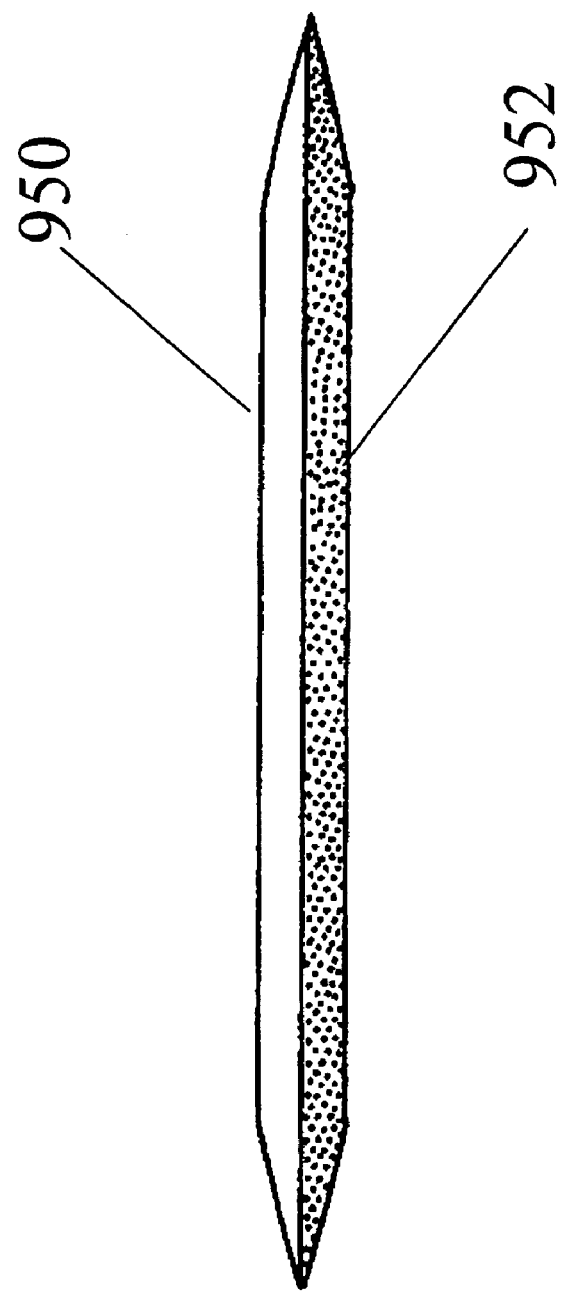
FIGS. 22A–C depict embodiments of fixation devices according to the present invention.
Figure 22B:
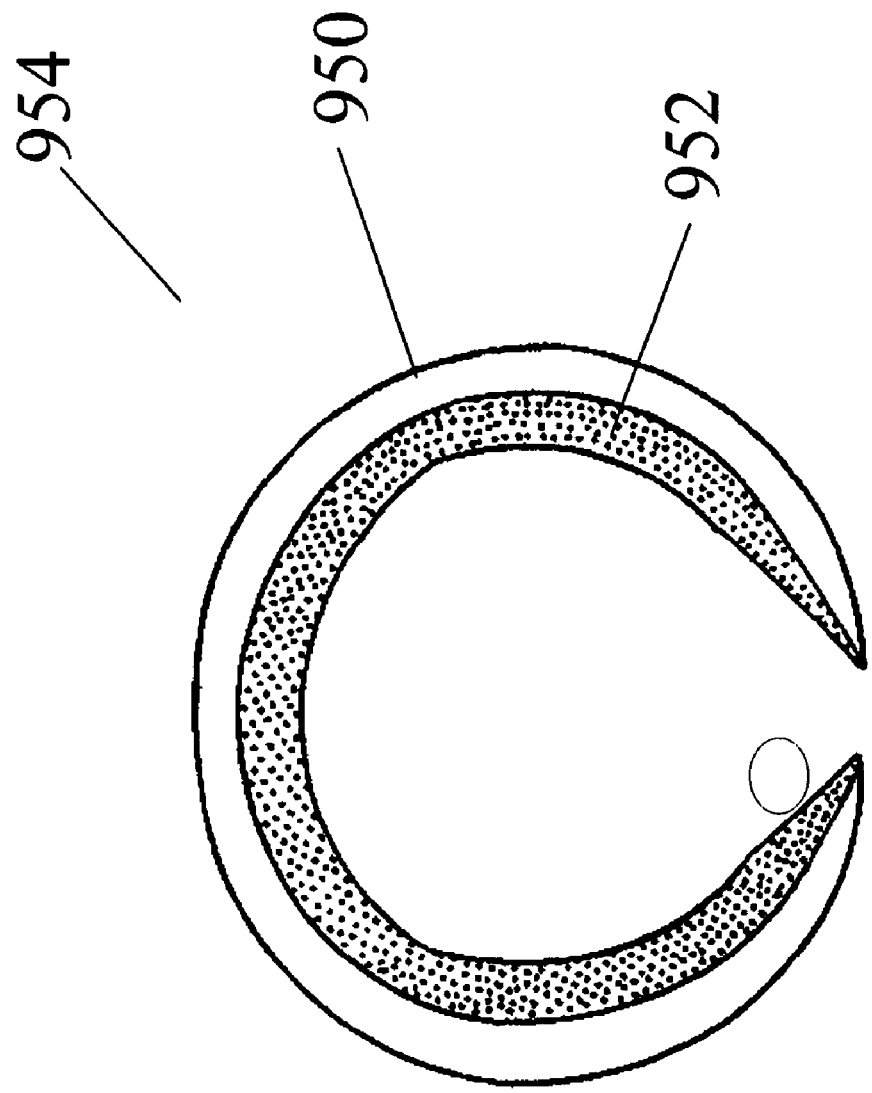
Figure 22C:
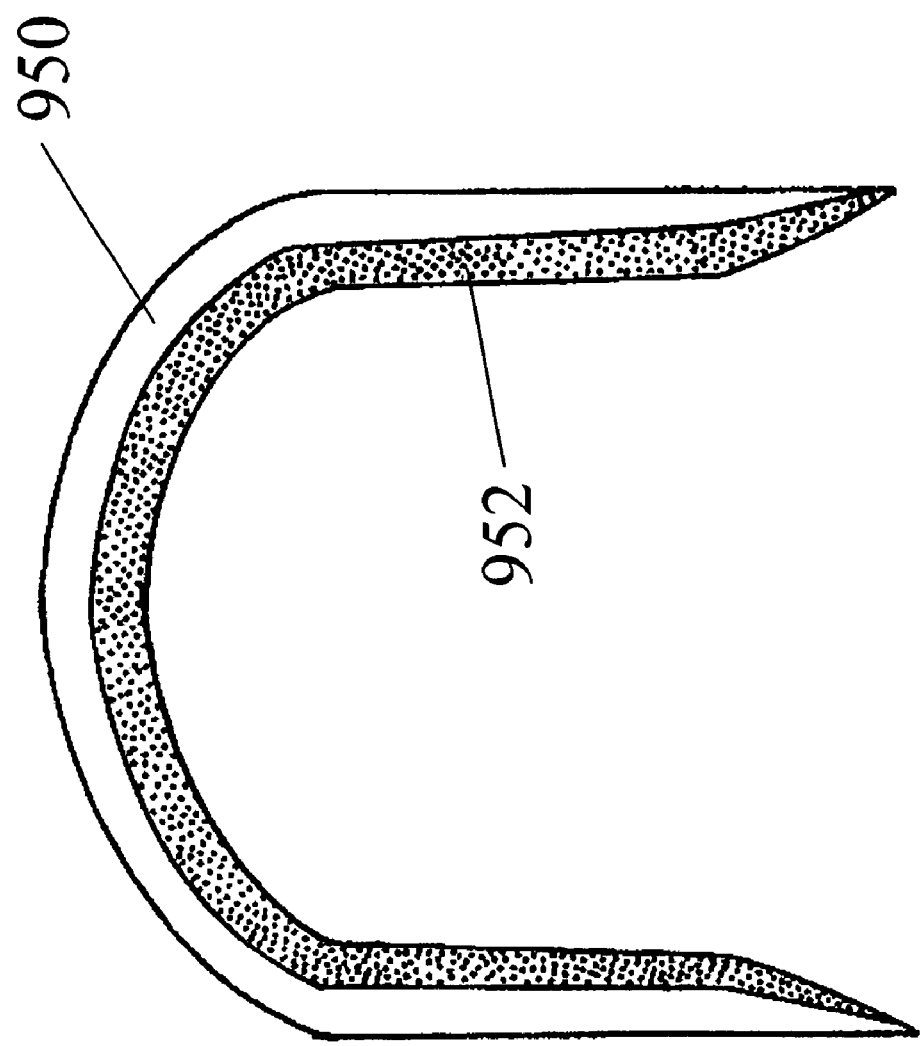

The embodiments depicted in FIGS. 22A–C may incorporate shape memory activators, as shown in FIG. 22A. A shape memory activator is a laminate comprising a spring 950 and a shape memory element 952. The shape memory element may be formed to hold a certain shape at a warm temperature, as shown in FIG. 22B, where the memorized shape is curved when the structure is warm and the inwardly curving force of the SMA element 952 overpowers the externally located spring 950. Conversely, when the SMA element 952 is cool, as shown in FIG. 22C, the spring 950 can overcome the force exerted by the SMA element 952. By selecting shapes properly, a reversible situation can be established wherein the memorized shape of the laminated activator structure at warm temperatures is intended to grasp or affix the tissues and wherein the cooled shape permits easy removal of the device from the patient.

Figure 23:
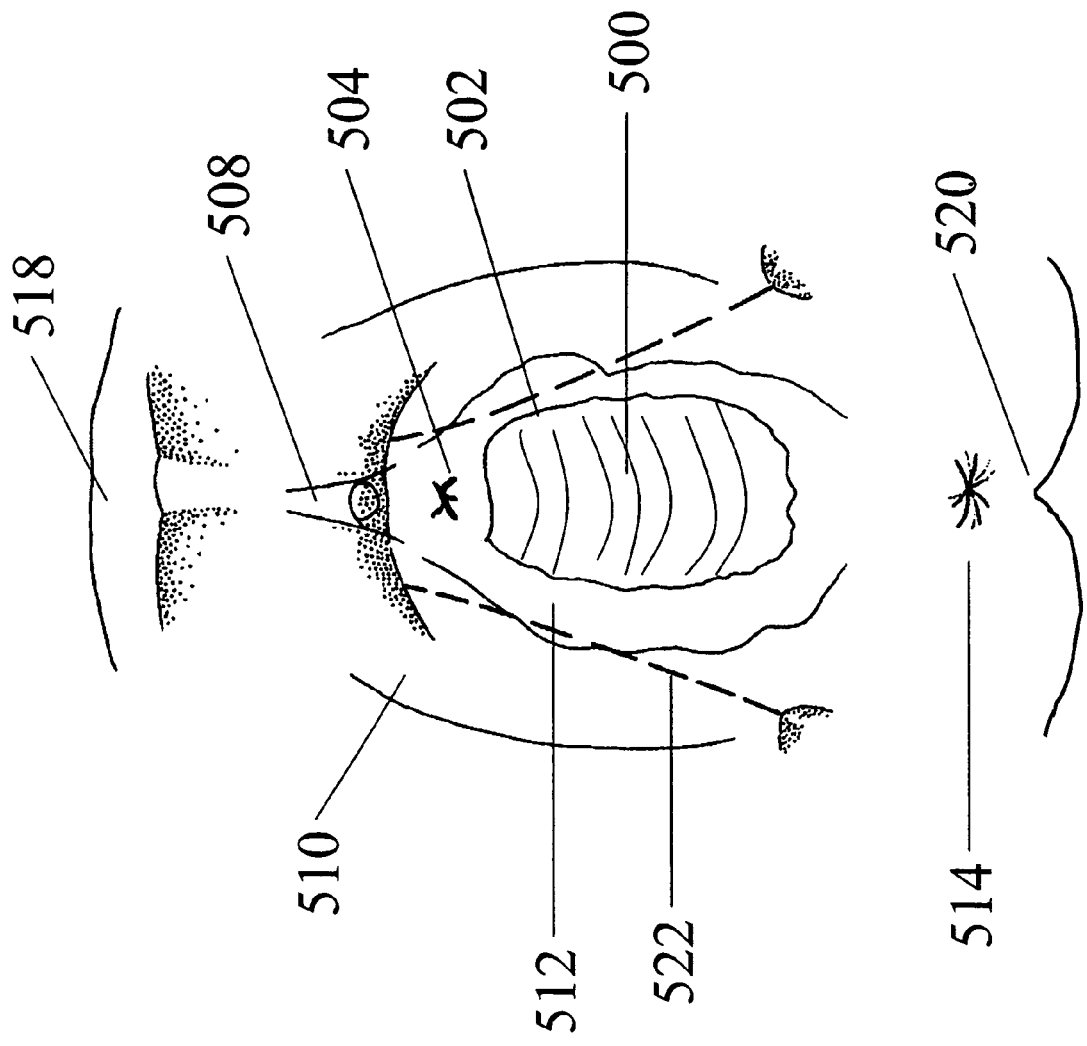
FIG. 23 shows a schematic anatomic diagram of the female perineum illustrating positioning of fixation devices according to one embodiment of the present invention.

In one embodiment of these systems and methods, a fixation device can be used to perform a procedure for repairing lax soft tissues in the female pelvis. As one example, these systems and methods may be used to simplify the surgery required for performing a paravaginal cystocele repair and thereby to eliminate many of the complications of traditional reconstructive surgery. FIG. 23 depicts a schematic anatomic representation of a gynecological view of the female perineum, illustrating places where fixation devices could be inserted according to these systems and methods to effect a paravaginal repair. In FIG. 23, anatomic landmarks are provided for orientation: the urethra 504 located posterior to the clitoris 508 between the labia majora 510, and the anus 514 positioned posteriorly. The mons pubis 518 indicates the anterior boundary of the region, and the intergluteal fold 520 indicates the posterior edge. The lips of the labia minora 512 have been displaced by lateral traction to render more visible the more medial anatomic features. In FIG. 23, a large cystocele 500 is shown, being visualized through the introitus 502 of the vagina. To perform a paravaginal repair according to these systems and methods, adequate anesthesia is induced, either general, regional or local, and appropriate prepping and draping is carried out. The fascial arcus or arcus tendineus fascia pelvis (ATFP) is identified by palpation. The ATFP is a condensation of fascia overlying the obturator internus and levator ani muscles, and can be found coursing between the posterior surface of the pubic bone and the ischial spine. With this knowledge, the location of the ATFP may be palpated through the vaginal mucosa. Once identified, the ATFP may provide the anchoring structure for the paravaginal cystocele repair. After the position of the ATFP has been identified by palpating it or otherwise identifying it, the tissues of the superior lateral sulci may be affixed thereto, along a line roughly indicated by 522. The number of fixation devices applied will be determined by the surgeon using routine surgical judgment. In certain cases, between 4 to 8 fixation devices will be applied on each side. The placement of these fixation devices across the vaginal epithelium into the arcus tendineus will effect the suspension of the paravaginal tissues and thus will reduce the cystocele.

Other gynecological and general surgical applications for these fixation devices may include rectocele and vaginal vault prolapse repair. Since the most proximal portion of the ATFP is located near the ischial spine, a procedure according to these systems and methods may provide apical support for vaginal vault prolapse. In addition, the fixation devices may be applied to the sacrospinous ligament, which can also be palpated transvaginally, effecting vaginal vault suspension. For rectocele repair, fixation devices according to the invention may be applied to affix the inferior lateral sulci to the ATFP and/or the levator ani, depending upon the diagnosed anatomic defect.

Figure 24A:
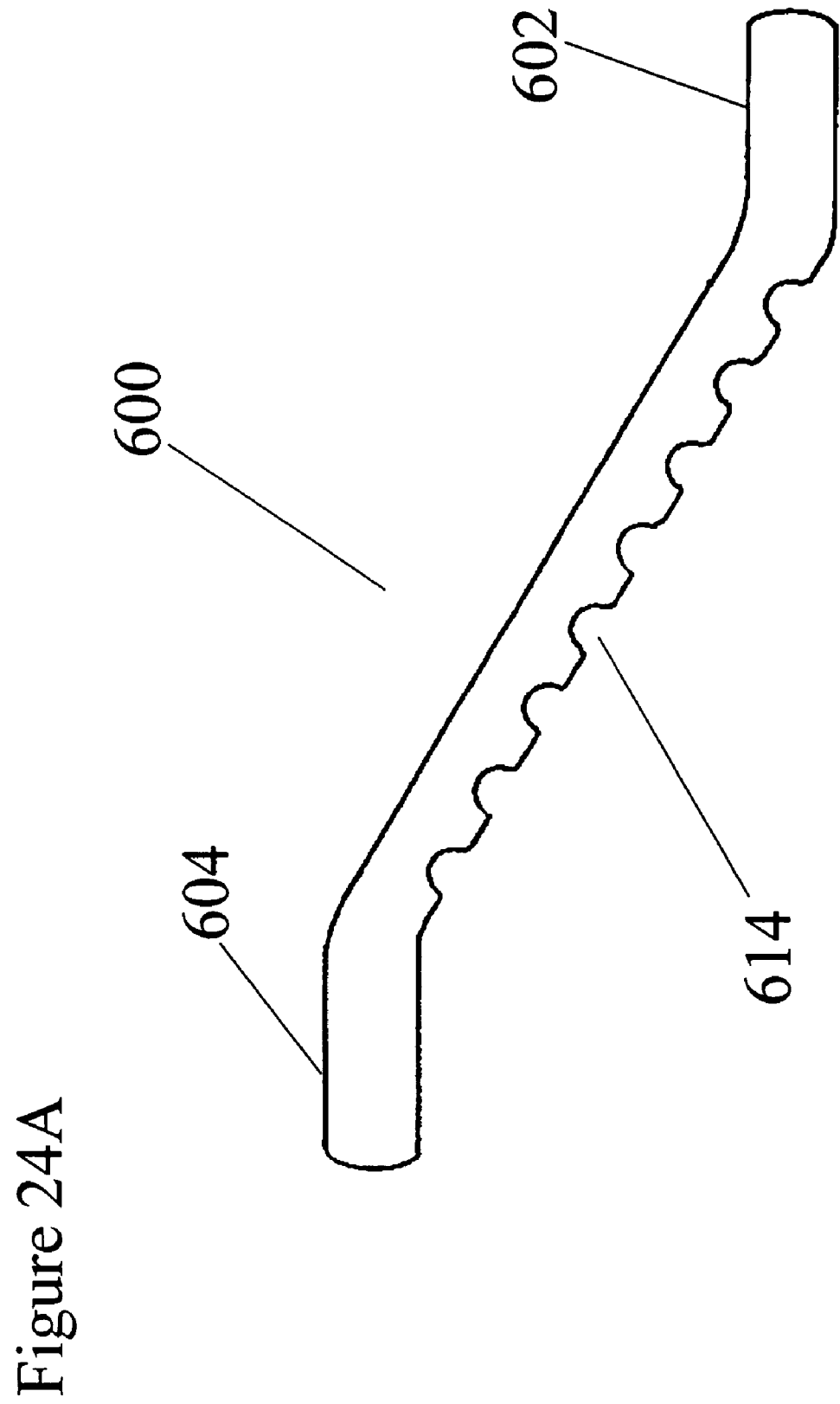
FIGS. 24A and B show embodiments of a template according to the present invention.
Figure 24B:
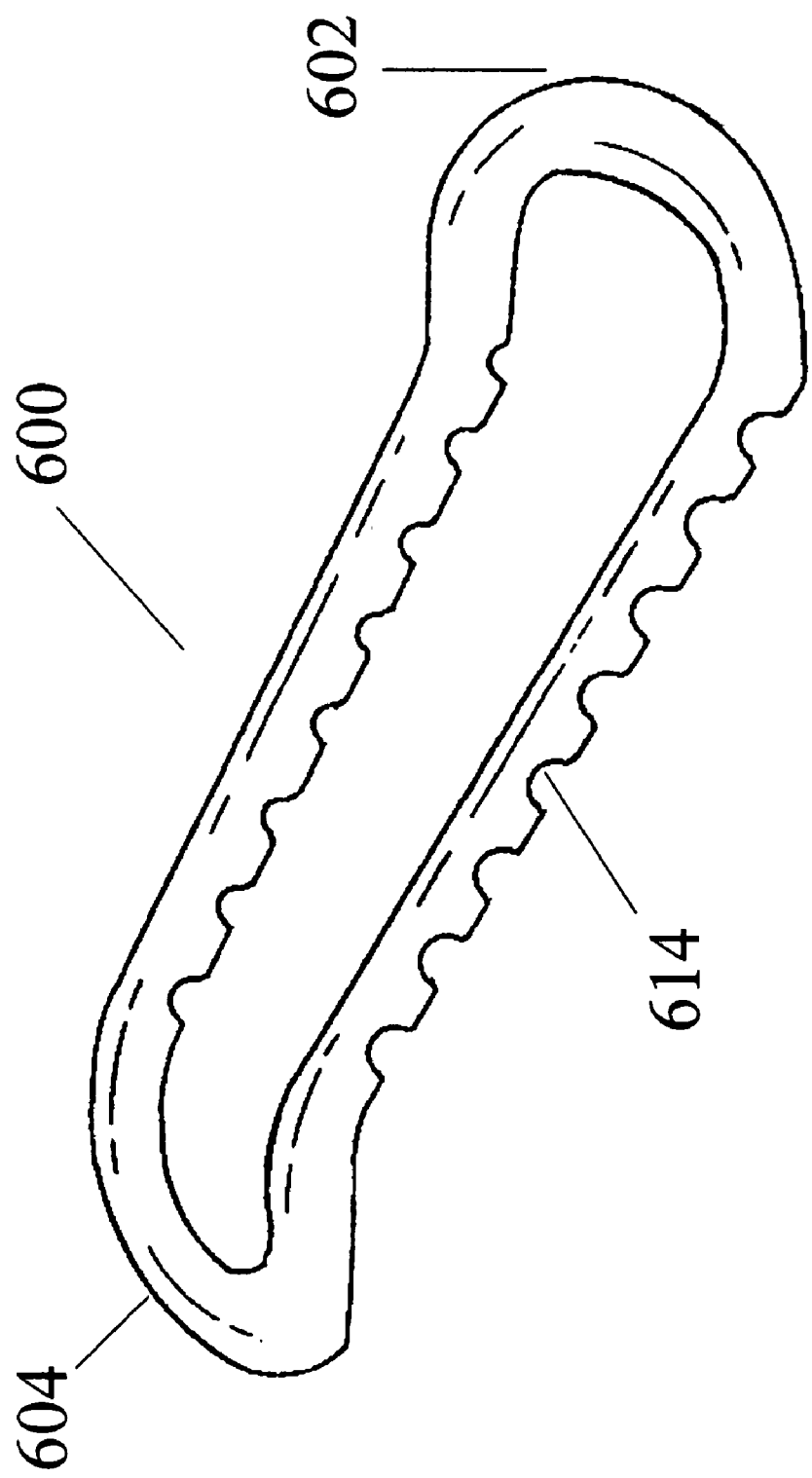
FIG. 24C shows an anatomic cross-sectional diagram of the female pelvis with a template positioned according to the systems and methods of the present invention.
Figure 24C:
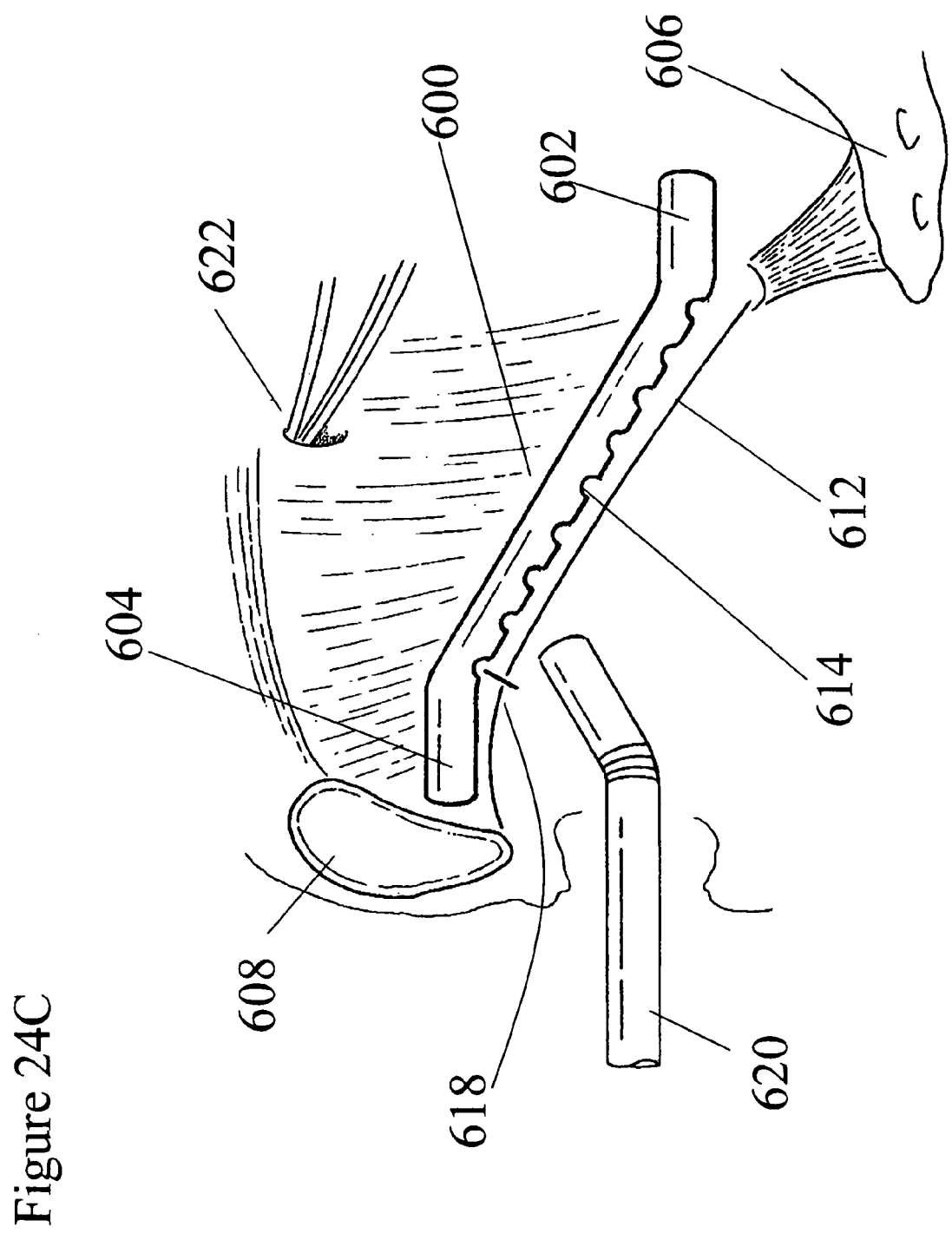

The systems and methods of the present invention may further include a template that facilitates accurate placement of the fixation devices. A template may be designed for each anatomic area to permit accurate placement. The template may be semi-flexible; thus permitting the template to be positioned over the proper area. For example, with vaginal paravaginal repair, the template may be placed between the ischial spine and the posterior pubic ramus, thereby defining the location of the arcus tendineus fascia pelvis, or fascial white line. In one embodiment, a template may be formed as depicted in FIGS. 24A–C. FIG. 24A shows a profile view of a template 600 adapted for insertion into the vagina, shaped with a proximal end 604 and a distal end 602. When inserted, the contour of the template 600 follows the line the arcus tendineus fascia of the pelvis, as shown in FIG. 24C. In FIG. 24C, a template 600 is shown positioned within the vagina with its proximal end 604 situated anteriorly, in proximity to the pubic symphysis 608. The distal end 602 is positioned deep within the vagina and is oriented posteriorly towards the sacrum 606. The template 600 correctly positioned parallels the arcus tendineus 612. The template 600 is equipped with a set of grooves 614 or indentations along its inferior border. The grooves 614 in the template 600 serve to guide the placement of soft tissue fixation devices 618 into the arcus tendineus 612 using an applicator device 620 as illustrated, or any other suitable applicator for the soft tissue fixation devices 618. The advantages of the template 600 include assisting the surgeon to properly insert and imbed the fixation devices 618 and further to avoid inadvertent placement of fixation devices into adjacent structures such as the obturator canal 622. FIG. 24B shows in more detail the configuration of a vaginal template 600 with a proximal end 604 and a distal end 602 and a set of grooves 614 along the inferior border serving to guide positioning of soft tissue fixation devices into the underlying anatomic structures.

Figure 25A:
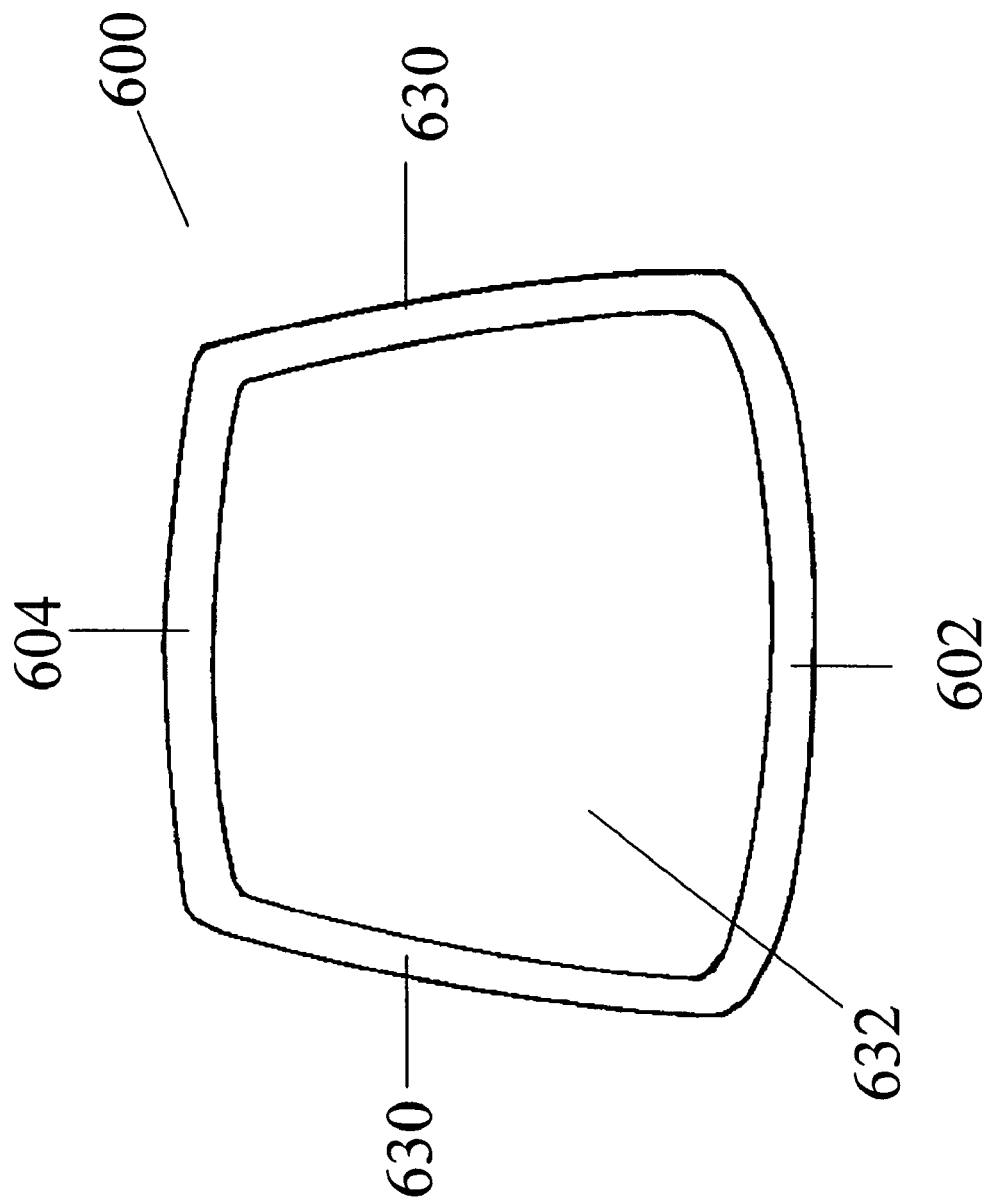
FIGS. 25A–C and FIG. 25E show embodiments of templates according to the present invention.
Figure 25B:
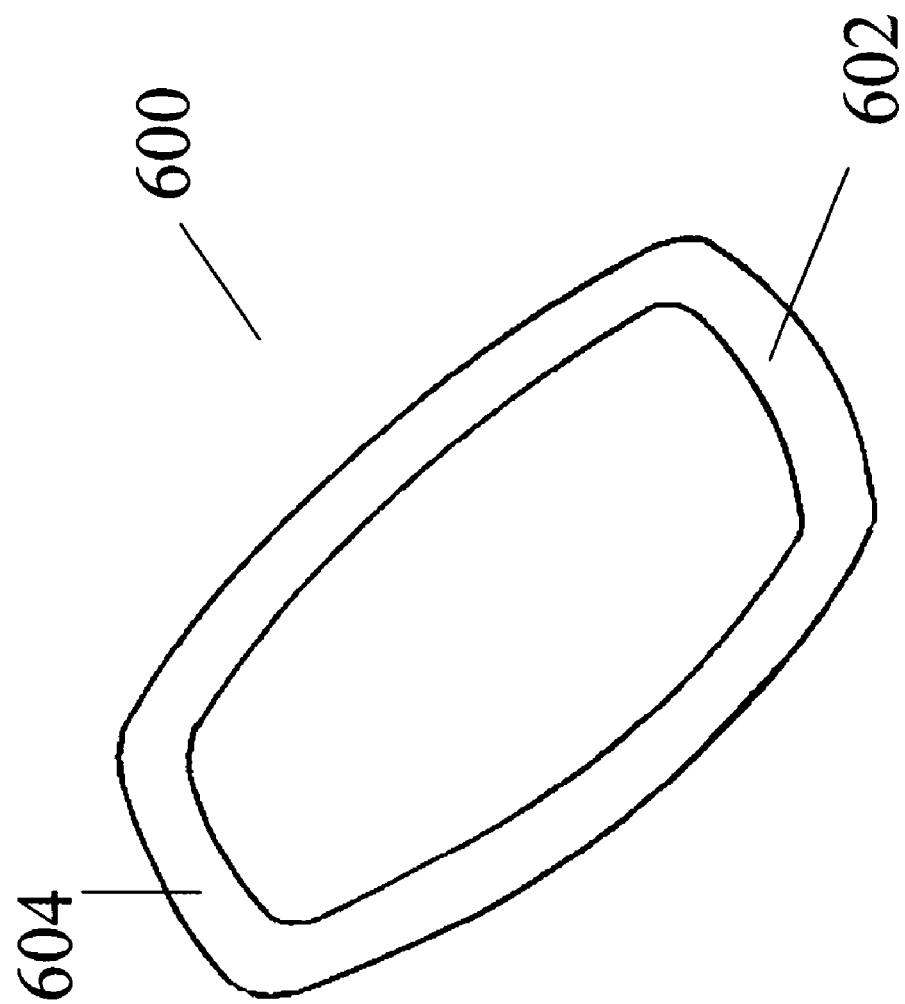
Figure 25C:
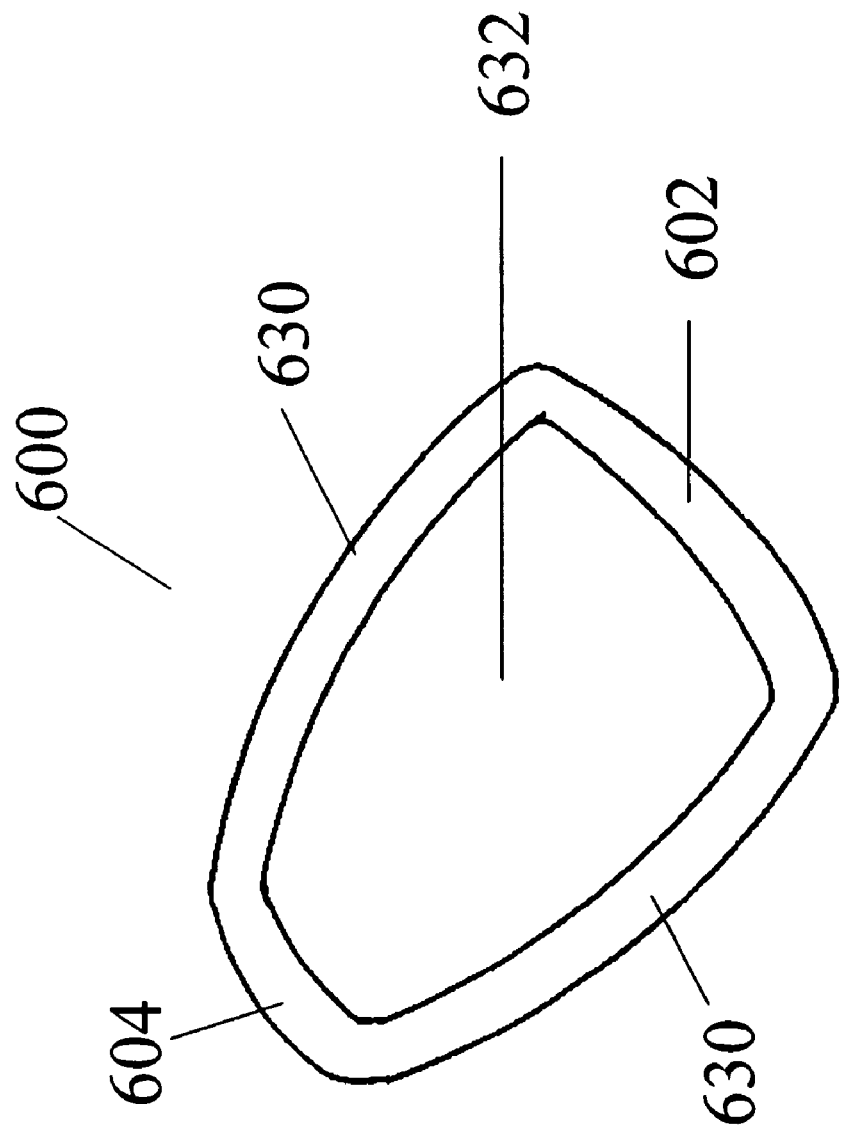
Figure 25D:
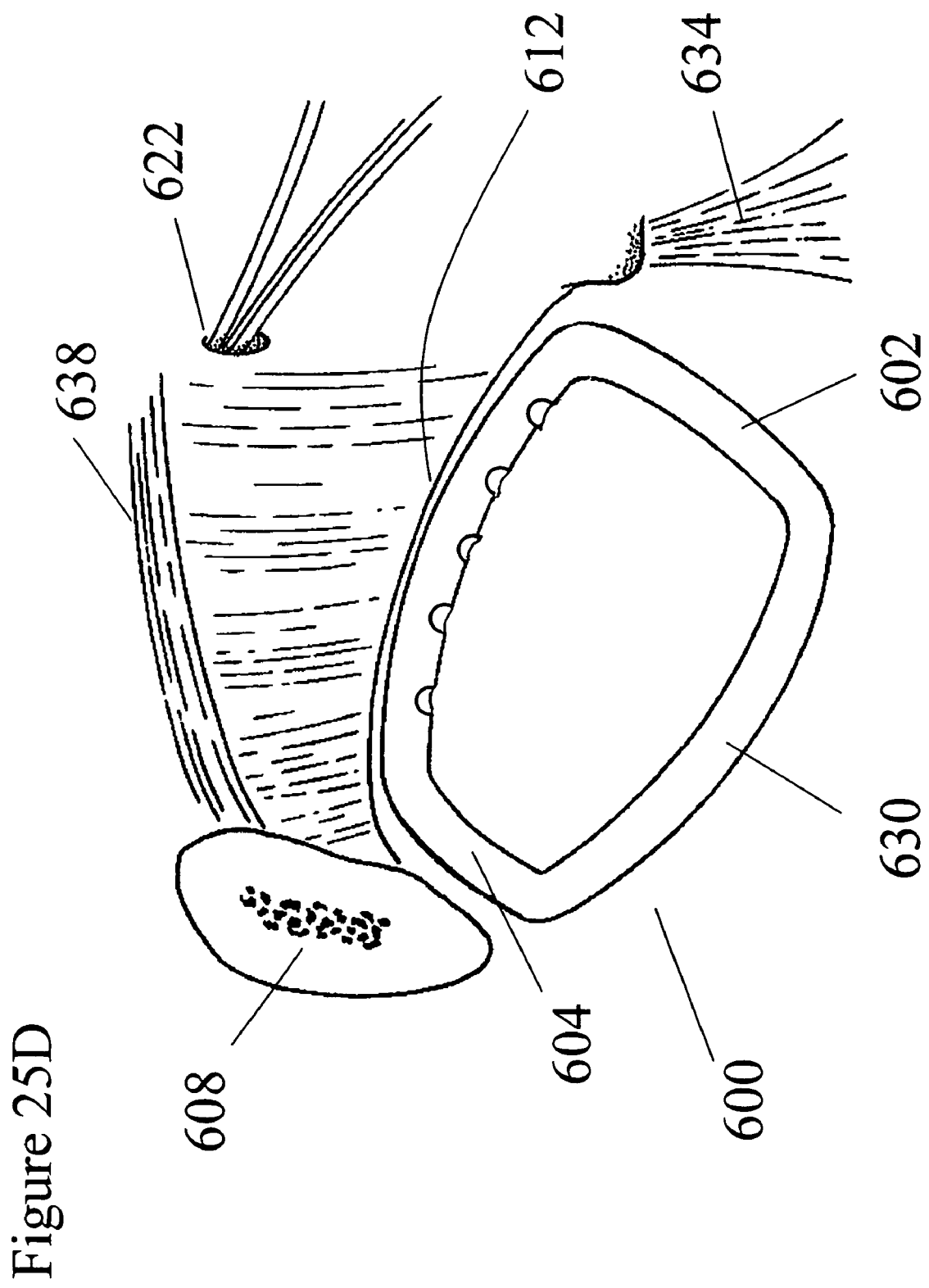
FIG. 25D shows an anatomic partial cross-sectional diagram of the female pelvis with a template positioned according to the systems and methods of the present invention.
Figure 25E:
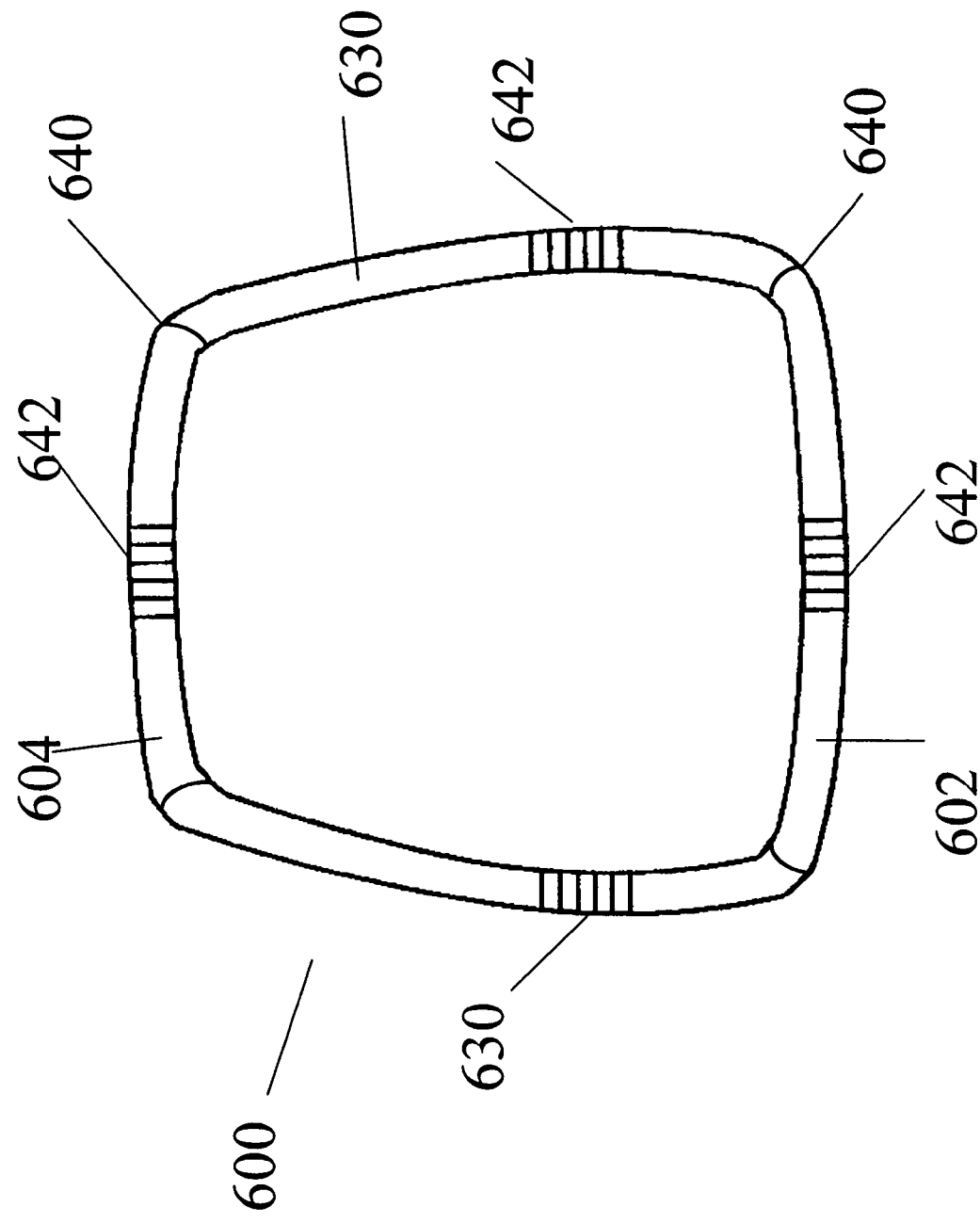

In alternate embodiments, a template for pelvic floor reconstructive surgery according to these systems and methods may be formed in a flatter design, as shown in FIGS. 25A–E. In FIG. 25A, an embodiment of a template 600 is shown with a proximal end 604 and a distal end, adapted for positioning within the vagina. In the depicted embodiment, the lateral members 630 may be slightly convex to coincide with the shape of the ATFP. FIG. 25A shows an anterior projection of a template 600. Optionally, a sheet of material 632 may be positioned to span the distance between the lateral members 630. The sheet of material 632 may be flexible or may be rigid with the capability for bending at a flexion point incorporated in the sheet of material 632. The sheet of material 632 may comprise a plurality of overlapping or interdigitating sheets to permit adjustment of the contour and size of the template 600. FIGS. 25B and C present perspective views of an embodiment of the template 600, illustrating the contouring of its shape to match the contours of the vaginal vault wherein it is to be positioned. FIG. 25D shows schematically a template 600 positioned within the vaginal vault, with the proximal end 604 situated in proximity to the pubic symphysis 608 and the distal end 602 positioned posteriorly, here in proximity to the sacrospinous ligament 634. The depicted embodiment shows grooves placed along the inferior aspect of the lateral members 630 (grooves are shown only on one lateral member for clarity) to guide placement of fixation devices into the ATFP 612. Anatomic structures in proximity further comprise the neurovascular bundle in the obturator canal 622, and Cooper's ligament 638. An alternate embodiment of a template 600 is shown at FIG. 25E, where a proximal end 604, a distal end 602 and two lateral members 630 are depicted. In the illustrated embodiment, flexible joints 640 are placed at intersections of members forming the template. In the illustrated embodiment, four flexible joints 640 are shown, although in other embodiments, fewer flexible joints 640 may be used, in keeping with the anatomic needs of a particular region. In an embodiment of a template 600 shown in FIG. 25E, a telescoping section 642 is shown on each component member to permit adjustment of the length of the member, thereby to adjust the size of the template 600 overall. While the depicted embodiment shows four telescoping sections 642, other embodiments may incorporate fewer telescoping sections 642 as anatomic variations require. Other adjustable features may be provided in other embodiments, as will be readily apparent to those of ordinary skill in the arts. Templates may also be provided in a range of sizes and shapes to meet the individual patient's anatomic needs. Materials for the template may be disposable or reusable. Plastics and metallic materials, or any other suitable material, may be used. A variety of guides may be provided on the template to direct the placement of fixation devices, as can be readily envisioned by practitioners of ordinary skill.

The templates illustrated may be used to guide the positioning of fixation devices according to these systems and methods. The templates, embodiments of which are depicted herein, may further be used to diagnose the anatomic abnormality responsible for a particular pelvic floor defect. When used diagnostically, a template is positioned in the vagina of a patient suffering from a pelvic floor defect such as a cystocele. The template, so positioned, may replicate the supportive forces produced by a soft tissue reconstruction involving affixing the lateral vaginal sulci to the ATFP. If the pelvic floor defect is due to laxity of the paravaginal tissues, the placement of a template as shown in FIGS. 22C and 25D may reduce the cystocele. If the template corrects the defect, the diagnosis of paravaginal laxity is confirmed. A soft tissue reconstruction according to these systems and methods may therefore be indicated.

Figure 26:
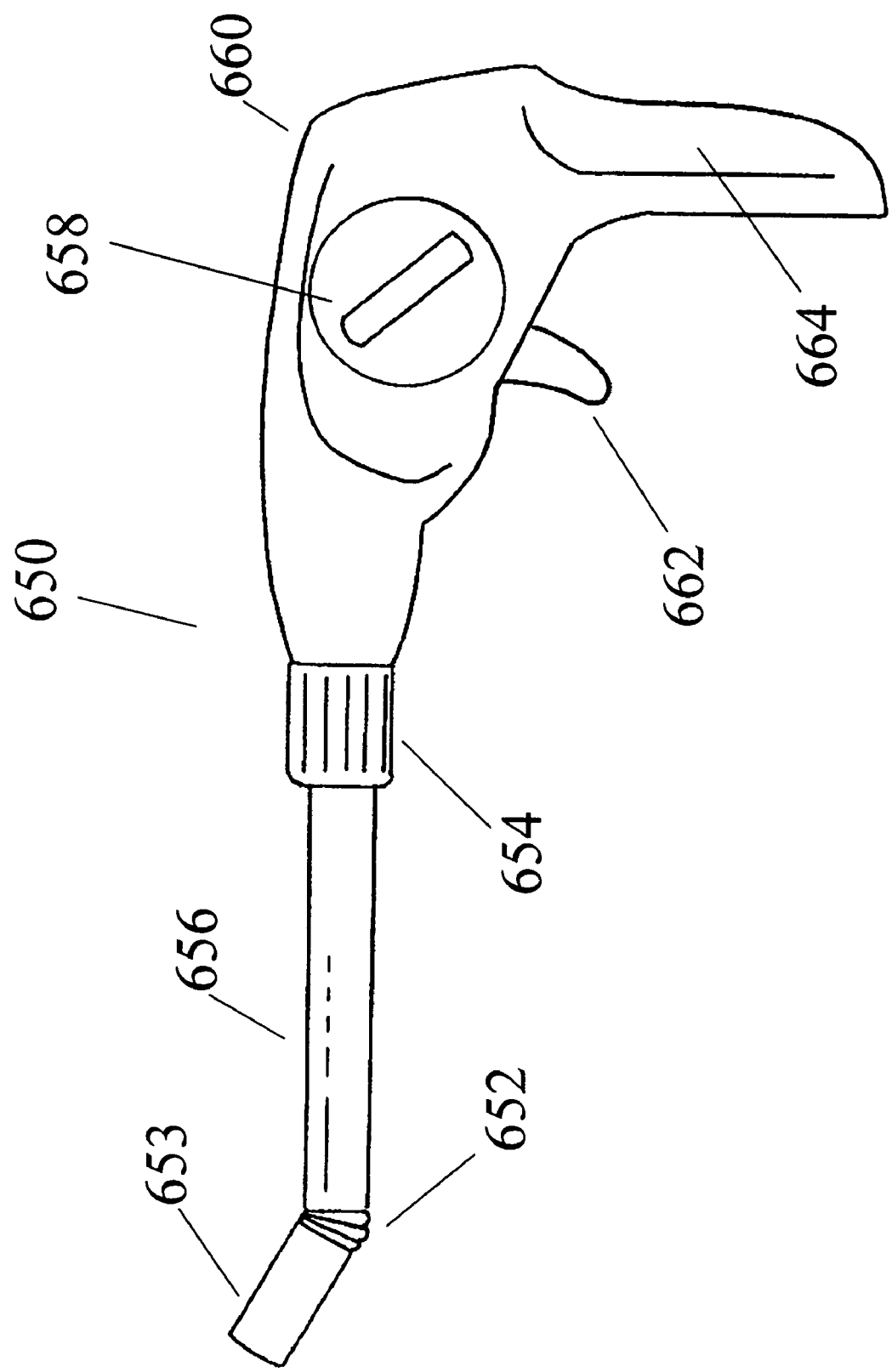
FIG. 26 depicts an embodiment of a fixation device applicator.

An embodiment of an applicator for soft tissue fixation devices is depicted in FIG. 26. The applicator 650 may be either a disposable (multiple fire) or reusable instrument. In certain embodiments, the applicator 650 may be adapted for inserting serially a plurality of fixation devices. The fixation devices may be available in a cartridge or as a prepackaged unit for use with an applicator 650. In one embodiment, the applicator 650 may possess an articulating joint 652 and a rotating knob 654 to facilitate the insertion of the tip 653 of the device into small or angulated spaces. In one embodiment, the articulation joint 652 may permit the tip 653 to be directed at a position perpendicular to the target tissue. The shaft 656 of the instrument may also rotate, directed by the rotating knob 654, providing another method to assure proper placement of the fixation device. In other embodiments, articulation may be performed with a lever or a wheel 658 near the proximal end 660 of the applicator 650. A lock mechanism (not shown) may be included to hold the instrument's articulable parts in their preselected position until altered by the operator. A handle 664 is provided to allow the operator to control the applicator 650, to position it in the anatomic region of interest and to direct the fixation devices into the tissue. After the applicator 650 has been positioned and has been inserted into an appropriate anatomic area to abut one of the tissues being approximated, the trigger 662 may be pulled to deploy an individual soft tissue fixation device. The next fixation device may automatically be brought into position for the subsequent firing. When the final fixation device has been placed, in one embodiment, the trigger 662 may no longer be capable of movement.

Figure 27A:
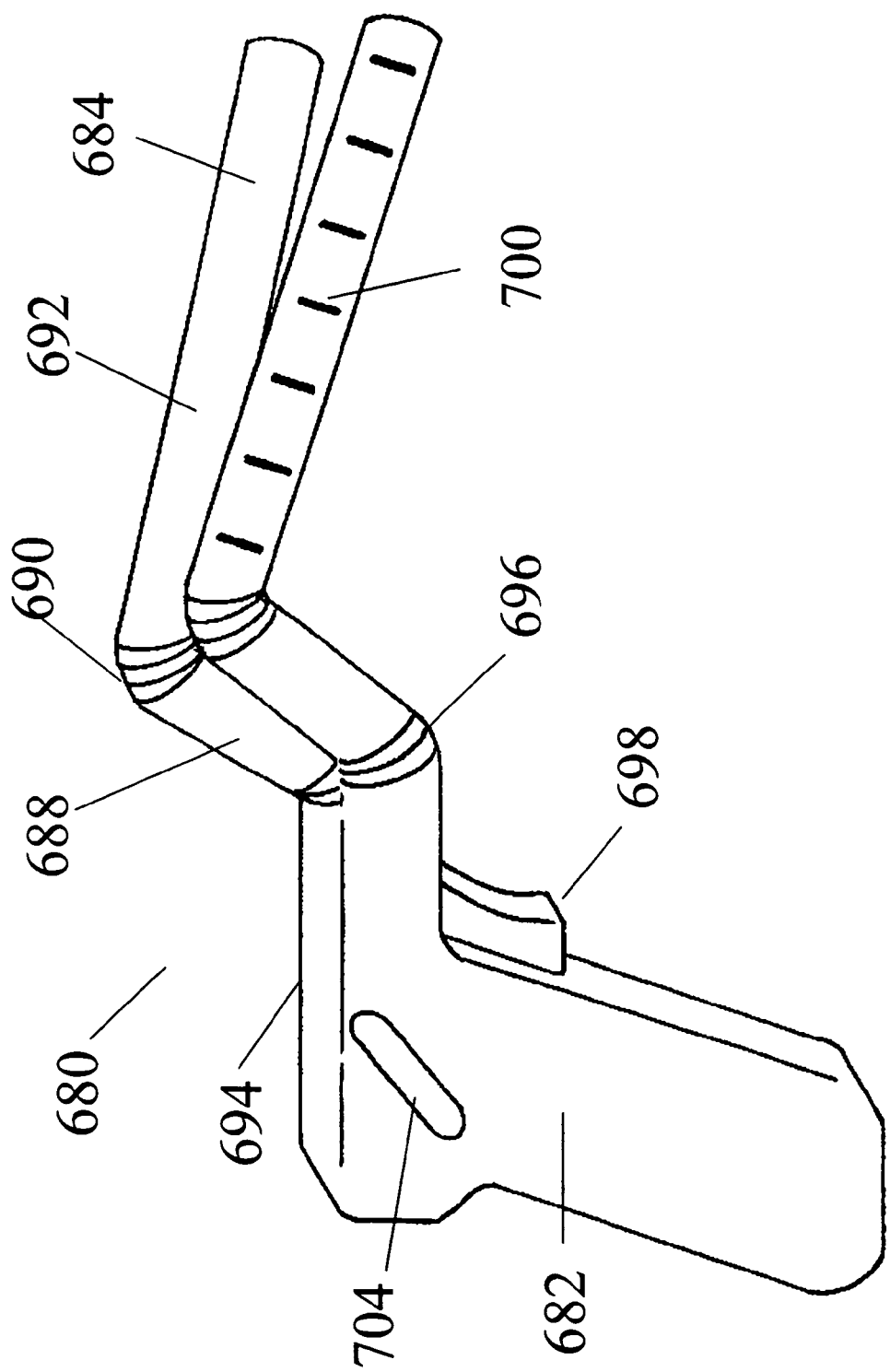
FIGS. 27A–C depict an embodiment of a fixation device applicator.
Figure 27B:
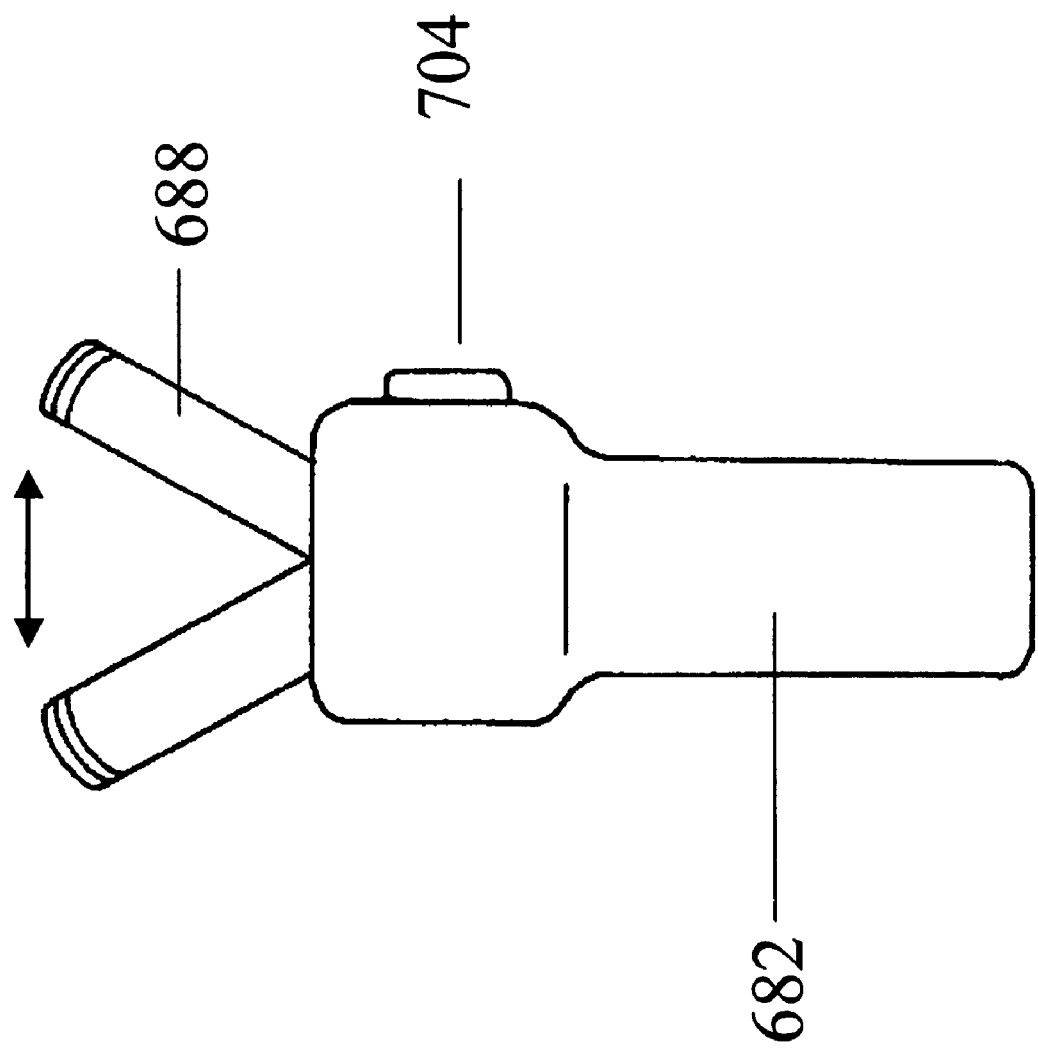
Figure 27C:
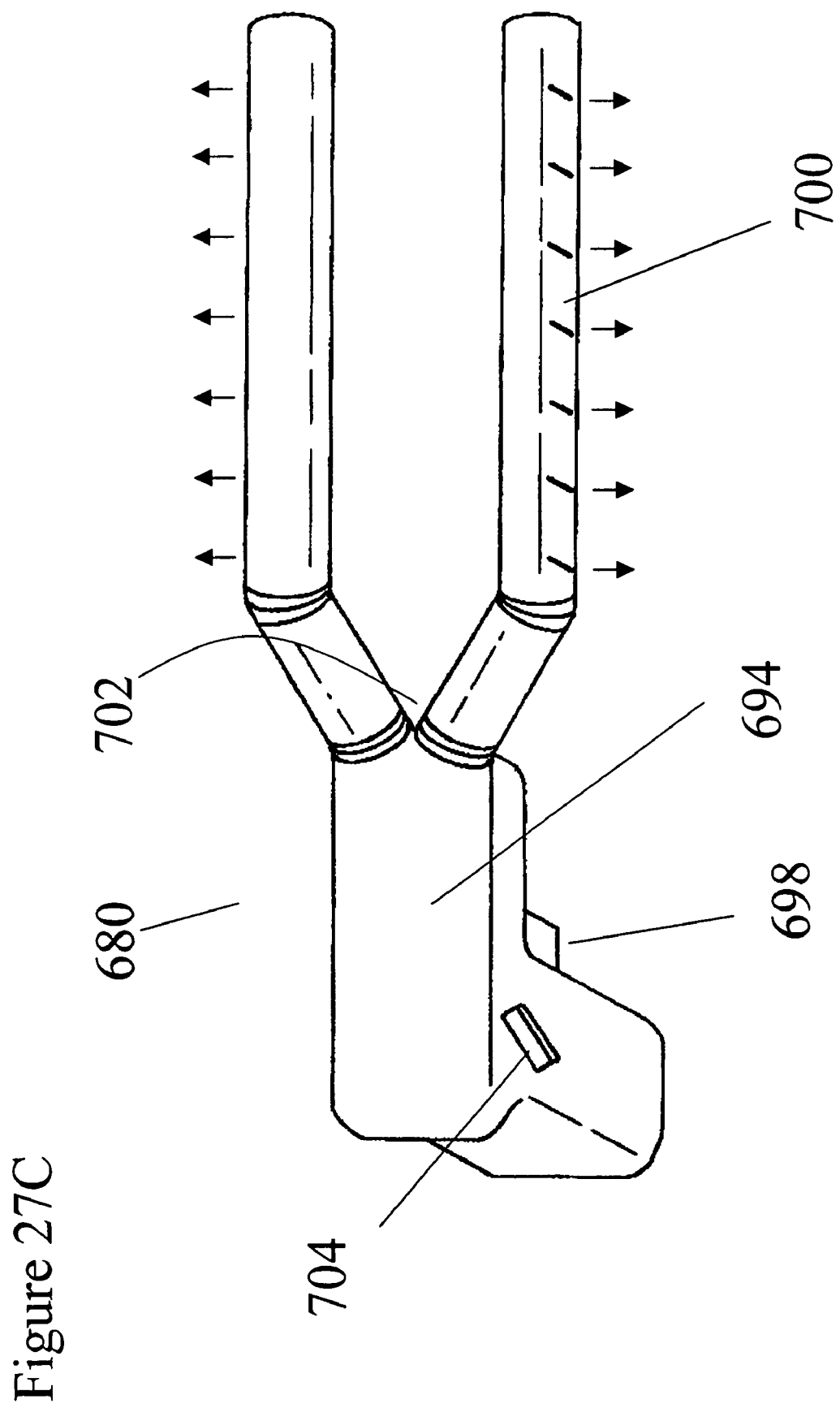

In an alternative embodiment, illustrated in FIGS. 27A–C, an applicator 680 is shown that is capable of inserting multiple soft tissue fixation devices simultaneously. The illustrated embodiment is adapted for use in the vagina. In this embodiment, a set of fixation devices or a cartridge of fixation devices 700 is affixed to the external aspect of a pair of arms 684 that are able to be urged outward, away from the central longitudinal axis of the device. The arms 684 are shaped to conform to the anatomy of the vagina and to parallel the contours of the ATFP. In the illustrated embodiment, best seen in FIG. 27B, the arms 684 articulate with a body 694 at a joint 702 that permits the arms 684 to be pushed outward when the operator advances the lever 704. The lever 704 may have a ratchet mechanism that allows the arms 684 to be gradually moved outward stepwise until they contact the target tissue located laterally to the applicator device. Pushing the lever 704 forward after the arms 684 contact the target tissue may permit the operator to apply an appropriate amount of pressure against the target tissue with the arms 684 before the fixation devices 700 are fired into the target tissue. When the appropriate amount of engagement between the arms 684 and the target tissue has been achieved, the operator may then pull the trigger 698 that delivers the row of fixation devices 700 into the target tissue. In the illustrated embodiment, both rows of fixation devices may be deployed simultaneously. In FIG. 27A, the lateral contour of the arms 684 is shown. Each arm 684 is shown in this figure with a proximal portion 688 articulating with the body 694 at a proximal joint 696, and further articulating with the a distal part 692 through an elbow joint 690. The distal part 692 of the arm bears the fixation device cartridge 692. In the illustrated embodiment, the proximal portion 688 of the arm 684 is angulated so that it will be oriented anteriorly when the applicator 680 is positioned within the vagina. The distal part 692 of the arm 684 is angulated so that it will be directed posteriorly when the applicator 680 is positioned within the vagina. FIG. 27C shows the operator's view of the applicator 680, with a proximal handle 682 and the proximal portion 688 of the arm visible. The angle between the two sets of arms conforms to the anatomic dimensions of the vagina, so that the arms will be urged into proper positions as they are pushed outward. While the illustrated embodiment uses a lever 704 to push the arms 684 outward, it is understood that a variety of mechanisms for effecting this motion may be readily identified by practitioners of ordinary skill in the art. The depicted embodiment is intended to be illustrative only, recognizing that a number of variations may be evident to ordinarily skilled artisans.

Although certain embodiments of these systems and methods are disclosed herein, it should be understood that other embodiments are envisioned as would be understood by one of ordinary skill in the art. Although the invention has been described by reference to specific embodiments thereof, it is not intended that the invention be limited to those illustrative embodiments. Rather, it is intended that all variations and modifications as fall within the spirit of the invention be included within the scope of the following claims. Accordingly, no limitation of the invention is intended by the foregoing description and accompanying drawings, except as is set forth in the appended claims.

What is claimed is:

1. A method of surgical paravaginal repair, comprising:
   placing a soft tissue fixation device vaginally through an insertion device adapted for inserting the soft tissue fixation device; and
   approximating at least one of the superior lateral sulci and inferior lateral sulci to the lateral pelvic sidewall without exposing the lateral pelvic sidewall through a surgical incision in a vaginal wall.

2. The method of claim 1, in which at least one of the superior lateral sulci and inferior lateral sulci is approximated to the lateral pelvic sidewall without making an incision.

3. The method of claim 1 in which a cystocele is repaired paravaginally.

4. The method of claim 1 further comprising penetrating the lateral pelvic sidewall with the soft tissue fixation device without exiting the lateral pelvic sidewall.

5. A method of surgical repair using a soft tissue fixation device and an insertion device, wherein the surgical repair is one of a paravaginal repair and a vaginal repair, the method comprising:
   placing the soft tissue fixation device vaginally through the insertion device; and
   approximating a vaginal epithelium to at least one of a lateral pelvic sidewall and a sacrospinous ligament without exposing at least one of the lateral pelvic sidewall and the sacrospinous ligament through a surgical incision in the vaginal epithelium.

6. The method of claim 5, further comprising:
   positioning a template dimensionally adapted for guiding a placement of the soft tissue fixation device in a vagina; and
   directing the soft tissue fixation device into the vagina in accordance with the template.

7. The method of claim 5, further comprising:
   examining a position of the tissue fixation device within the vaginal epithelium and a tissue approximated thereto; and
   removing the soft tissue fixation device when the soft tissue fixation device is malpositioned.

8. The method of claim 7, further comprising:
   providing a remover to extricate the fixation device from the vaginal epithelium and the tissue approximated thereto; and
   employing the remover to remove the soft tissue fixation device that is malpositioned.

9. The method of claim 7, wherein the soft tissue fixation device that is malpositioned is removed by traction.

10. The method of claim 5, wherein the soft tissue fixation device is selected from a group including sutures, suture/cleat combinations, suture/lock combinations, staples, screws, barbed tacks, and anchors.

11. The method of claim 5, wherein a lateral vaginal sulcus is approximated to at least one of an arcus tendineus fascia of the pelvis and a structure of a levator ani for paravaginal repair of a rectocele.

12. The method of claim 11, wherein the structure of the levator ani includes at least one of a fascia and a muscle.

13. The method of claim 5, wherein the structural repair includes a soft tissue repair selected from a group including a cystocele, urethrocele, vaginal vault prolapse, rectocele, and uterine prolapse.

14. The method of claim 5, further comprising identifying the soft tissue to be repaired by a diagnostic modality selected from a group consisting of MRI, fluoroscopy, CT scan, conventional radiology, ultrasound, laparoscopy and endoscopy.

15. The method of claim 5, further comprising guiding the fixation device into at least one anatomic structure by a modality selected from a group consisting of MRI, fluoroscopy, CT scan, conventional radiology, ultrasound, laparoscopy, endoscopy, direct vision and intraoperative palpation.

16. The method of claim 5, in which the vaginal epithelium is approximated to at least one of a lateral pelvic sidewall and a sacrospinous ligament without making an incision.

17. A method of soft tissue repair, wherein the repair is at least one of a paravaginal repair and a vaginal repair, the method comprising:
   penetrating an intact outer wall of a first soft tissue;
   penetrating a second soft tissue; and
   affixing said first soft tissue to said second soft tissue without exposing one of the first tissue and the second tissue through a surgical incision in the other tissue.

18. The method of claim 17, in which the first tissue is affixed to the second tissue without making an incision.

19. A method of surgical paravaginal repair comprising:
   placing a soft tissue fixation device vaginally through an insertion device adapted for inserting the soft tissue fixation device; and
   performing a paravaginal repair by approximating at least one of the superior lateral sulci and inferior lateral sulci to the lateral pelvic sidewall, without exposing the lateral pelvic sidewall through a surgical incision in a vaginal wall.

20. The method of claim 19 in which a cystocele is repaired paravaginally.

21. The method of claim 19 further comprising penetrating the lateral pelvic sidewall with the soft tissue fixation device without exiting the lateral pelvic sidewall.

* * * * *